United States Patent [19]

Kubota et al.

[11] Patent Number: 5,352,792

[45] Date of Patent: Oct. 4, 1994

[54] THIOALKYLTHIO CEPHALOSPORIN DERIVATIVES

[75] Inventors: Tadatoshi Kubota, Habikino; Masaharu Kume, Amagasaki, both of Japan

[73] Assignee: Shionogi & Co., Ltd., Japan

[21] Appl. No.: 25,628

[22] Filed: Mar. 2, 1993

Related U.S. Application Data

[62] Division of Ser. No. 729,413, Jul. 12, 1991, Pat. No. 5,214,037.

[30] Foreign Application Priority Data

Jul. 19, 1990 [JP] Japan .................. 2-191899
Oct. 25, 1990 [JP] Japan .................. 2-289772
Nov. 21, 1990 [JP] Japan .................. 2-319578
Jun. 19, 1991 [JP] Japan .................. 3-147357

[51] Int. Cl.$^5$ .................. C07D 401/06; C07D 249/04
[52] U.S. Cl. .................. 548/255; 546/276; 548/110
[58] Field of Search .................. 548/255, 110; 546/276

[56] References Cited

U.S. PATENT DOCUMENTS 3,481,946 12/1969 Schmidt et al. .................. 260/302
4,482,565 11/1984 Foglio et al. .................. 424/270

FOREIGN PATENT DOCUMENTS 0210078 1/1987 European Pat. Off. .
329457 8/1989 European Pat. Off. .
2140807 12/1984 United Kingdom .

*Primary Examiner*—Patricia L. Morris
*Attorney, Agent, or Firm*—Wenderoth, Lind & Ponack

[57] ABSTRACT

A novel thioalkylthio cephalosporin antibiotic compound of formula I:

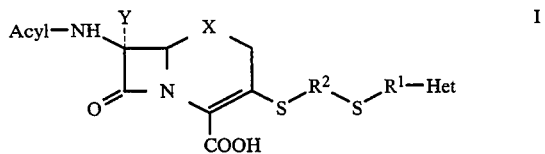

wherein Acyl is $C_1-C_{12}$ acyl; Het is optionally substituted monocyclic heteroaromatic group containing one or more hetero atoms; $R^1$ is a single bond or $C_1-C_4$ alkylene; $R_2$ is a straight or branched $C_1-C_4$ alkylene; X is a sulfur atom or sulfoxide group; and Y is a hydrogen atom or methoxy group, or a pharmaceutically acceptable salt or an amino-, carboxy- and/or hydroxy-protected derivative thereof, a formulation containing the same and a method for treating bacterial infections.

7 Claims, No Drawings

THIOALKYLTHIO CEPHALOSPORIN DERIVATIVES

This is a divisional application of Ser. No. 07/729,413, filed Jul. 12, 1991 now U.S. Pat. No. 5,214,037.

This invention relates to novel cephalosporin derivatives, processes for producing said compounds, antibiotic formulations which contain, as an active ingredient, a compound of the invention, and methods for treating bacterial infections by administering said formulation to subjects.

It has been recognized that cephalosporins are useful antibiotics of a broad antibacterial spectrum and various cephalosporin derivatives have been prepared and provided so far. However, because of the development of low-sensitive or resistant bacteria, improved useful antibiotic agents are continuously needed.

The inventors had made investigations with the aim of developing novel and useful antibiotics and synthesized many cephalosporin derivatives which have at the 3-position of cephem nucleus a thioalkylthio side chain substituted with a heterocyclic group and evaluated their antibacterial activities. Now, the inventors have found that a certain class of such compounds possess a potent bactericidal or antibacterial activity and show a high blood level on oral administration.

Thus, the present invention provides a compound of formula I:

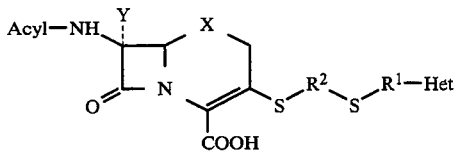

wherein:
Acyl is $C_1-C_{12}$ acyl; Het is optionally substituted monocyclic heteroaromatic group containing one or more hereto atoms; $R^1$ is a single bond or $C_1-C_4$ alkylene; $R_2$ is a straight or branched $C_1-C_4$ alkylene; X is a sulfur atom or sulfoxide group; and Y is a hydrogen atom or methoxy group, or a pharmaceutically acceptable salt or an amino, carboxy- and/or hydroxy-protected derivative thereof.

For the purpose of the present invention, as disclosed and claimed herein, the following terms are defined as below.

In the definition of Het, the term "heteroaromatic group" refers to 5- or 6-membered ring which contains more than one hetero atoms selected from nitrogen, sulfur, and the like. Preferred examples of heteroaromatic groups are 5-membered heterocyclic ring containing 3 or 4 hetero atoms selected from nitrogen and sulfur. Specific examples are pyridyl, triazolyl such as 1,2,3- or 1,2,4-triazolyl, thiadiazolyl such as 1,2,3- or 1,3,4-thiadiazolyl, tetrazolyl, and the like. The heteroaromatic groups may have one or more substituents selected from, for example, lower alkyl such as methyl, ethyl, and the like. Especially preferable heteroaromatic groups are optionally substituted 1,2,3- or 1,2,4-triazolyl and 1,2,3- or 1,3,4-thiadiazolyl, where the substituent is methyl.

In the definition of Acyl, the term "$C_1-C_{12}$ acyl" refers to acyl having 1 to 12 carbon atoms. Examples of $C_1-C_{12}$ acyl are alkanoyl, aroyl or homo- or heterocyclic aralkanoyl. The acyl group may be substituted with appropriate substituent(s), and functional groups may be protected by protecting groups generally used in the field of cephalosporin. Preferred acyl groups are $C_1-C_8$ alkanoyl, $C_7-C_{11}$ aroyl, and 5- or 6-membered homo- or hetero-cyclic aralkanoyl each may have an optional substituent. Examples of optional substituents include $C_1-C_5$ alkyl, $C_2-C_5$ carboxyalkyl, alkenyl, cycloalkenyl, amino, imino, hydroxyimino, $C_1-C_5$ alkyloxyimino, $C_1-C_5$ alkenyloxyimino, $C_3-C_5$ cycloalkyloxyimino, carboxy-$C_1-C_5$ alkylthio, hydroxy, oxo, $C_1-C_5$ alkoxy, halogen, and the like. Preferred substituents are haloalkylthio, alkoxyimino, cyclic alkoxyimino, alkenyloxyimino, amino, protected amino, hydroxy, oxo, hydroxyimino, protected hydroxyimino, carboxyalkoxyimino, carboxyalkenyloxyimino, and the like.

Typical examples of optionally substituted acyl include (Z)-(2-aminothiazol-4-yl)-2-hydroxyiminoacetyl, 2-(2-aminothiazol-4-yl)acetyl, α-phenylglycyl, D-mandeloyl, 2-(2-aminothiazol-4-yl)glyoxylyl, difluoromethylthioacetyl, (Z)-2-(2-aminothiazol-4-yl)-2-pentenoyl, (Z)-2-(2-aminothiazol-4-yl)-2-tetrahydropyranyloxyiminoacetyl, (Z)-2-(-2-aminothiazol-4-yl)-2-trityloxyiminoacetyl, (Z)-2-(2-aminothiazol-4-yl)-2-(2-propenyloxyimino)acetyl, (Z)-2-(2-aminothiazol-4-yl)-2-cyclopentyloxyiminoacetyl, (Z)-2-(2-aminothiazol-4-yl)-2-(carboxymethoxyimino)acetyl, (Z)-2-(2-aminothiazol-4-yl)-2-[(S)-1-carboxyethoxyimino)]acetyl, (Z)-2-(1-carboxy-1-methylethoxyimino)acetyl, (Z)-2-(2-aminothiazol-4-yl)-2-(1-carboxyvinyloxyimino)acetyl, and the like. Especially preferred acyl is (Z)-2-(2-aminothiazol-4-yl)-2-hydroxyiminoacetyl wherein the hydroxyimino group is optionally modified with a conventional hydroxy-protecting group, $C_1-C_5$ alkyl, or $C_2-C_5$ carboxyalkyl.

The term "straight or branched $C_1-C_5$ alkylene" refers to methylene, ethylene, methylmethylene, and the like.

Although all the compounds of formula I as defined above are suited for the purpose of the invention, there are certain preferable compounds. Thus, compounds wherein $R^1$ is a single bond, $R^2$ is methylene, Het is 2-pyridyl, 1,2,3- or 1,2,4-triazolyl, 1,2,3- or 1,3,4-thiadiazolyl each optionally substituted with methyl; X is sulfur; Y is hydrogen; and Acyl is (Z)-2-(2-aminothiazol-4-yl)-2-hydroxyiminoacetyl are especially preferable.

For the purpose of the invention, functional groups such as carboxyl, amino and hydroxyl groups may be conventionally protected by appropriate protecting groups commonly used in the field of cephalosporin antibiotics.

The carboxy protecting groups are selected from those used in the art and serve the function of blocking the carboxyl group while reactions are carried out at other sites of the molecule. Such groups generally contain less than about 19 carbon atoms and bind to carboxyl group reversibly without affecting the other parts of the molecule. Typical examples include optionally substituted $C_1-C_8$ alkyl, for example, methyl, methoxymethyl, ethyl, ethoxymethyl, iodomethyl, propyl, isopropyl butyl, isobutyl, ethoxyethyl, methylthioethyl, methanesulfonylethyl, trichloroethyl, t-butyl, and the like; optionally substituted $C_3-C_8$ alkenyl, for example, propenyl, allyl, isoprenyl, hexenyl, phenylpropenyl, dimethylhexenyl, and the like; optionally substituted $C_7-C_{19}$ aralkyl, for example, benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl, and the like; optionally substituted $C_6-C_{12}$ aryl, for example, phenyl, toluyl diisopropylphenyl, xylyl, trichlorophenyl, pentachlorophenyl, indanyl, and the like; optionally substituted $C_1-C_{12}$ amino which is, e.g., an ester with acetone oxime, acetophenone oxime, acetoaldoxime, N-hydroxysuccineimide, N-hydroxyphthalimide, or the like; optionally substituted $C_3-C_{12}$ hydrocarbonated silyl, for example, trimethylsilyl, dimethylmethoxysilyl, t-butyldimethylsilyl, and the like; optionally substituted $C_3-C_{12}$ hydrocarbonated stannyl, for example, trimethylstannyl, and the like. Another carboxy protecting groups are pharmaceutically active ester forming groups. Examples of such groups include 1-(oxygen-substituted)-$C_2$ to $C_{15}$ alkyl groups, for example, a straight, branched, ringed, or partially ringed alkanoyloxyalkyl, such as acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl, and the like; $C_3-C_{15}$ alkoxycarbonyloxyalkyl such as ethoxycarbonyloxyethyl, isopropoxycarbonyloxypropyl, isopropoxycarbonyloxyethyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl, and the like; $C_2-C_8$ alkoxyalkyl, such as methoxymethyl, methoxyethyl, and the like; $C_4-C_8$ 2-oxacycloalkyls, such as tetrahydropyranyl, tetrahydrofuranyl, and the like; substituted $C_8-C_{12}$ aralkyls, for example, phenacyl, phthalidyl, and the like; $C_6-C_{12}$ aryl, for example, phenyl, xylyl, indanyl, and the like; $C_2-C_{12}$ alkenyl, for example, allyl, isoprenyl, 2-oxo-1,3-dioxolyl-4-yl-methyl, and the like. Among the above, a protecting group used to block the carboxyl group during reactions is usually removed at the final step of the reaction, and therefore its structure is not essential. Thus, as one of skill in the art can easily appreciate, protecting groups can be selected from various equivalent groups including amides, acid anhydrides formed with carbonic acid or carboxylic acids, and the like, as long as an aimed carboxyl group is protected properly.

The hydroxy protecting group is $C_1-C_{10}$ protecting group conventional in the field of cephalosporin and introduceable and removable without adverse effect on other part of the molecule. Typical examples of the groups include easily removable ester forming group, for example, $C_1-C_{10}$ carboxylic acyl (alkanoyl such as formyl, acetyl, propionyl, pivaloyl and $C_7-C_{10}$ aroyl such as benzoyl, toluoyl, xyloyl), $C_1-C_{10}$ carbonic acyl (alkoxycarbonyl, trichloroalkoxycarbonyl, benzyloxycarbonyl, p-nitrobenzyloxycarbonyl, p-methoxybenzyloxy-carbonyl, o-nitrobenzyloxycarbonyl, allyloxycarbonyl); easily removable $C_2-C_4$ ether forming group (tetrahydropyranyl, tetrahydrofuranyl, methoxymethyl, methoxyethoxymethyl, etc. ), $C_3-C_{18}$ hydrocarbylsilyl (trimethylsilyl, triethylsilyl, dimethylphenylsilyl, diphenyl-t-butylsilyl, dimethyl-t-pentylsilyl, etc. ), and $C_7-C_{19}$ reactive aralkyl (triphenylmethyl, etc.).

The amino-protecting group is a $C_1-C_{20}$ protecting group conventional in the field of cephalosporin and introduceable and removable without adverse effect on other part of the molecule. Typical examples of the group include $C_1-C_8$ alkyl (t-butyl, methoxymethyl, methoxyethoxymethyl, trichloroethyl, tetrahydropyranyl, etc. ), $C_7-C_{19}$ aralkyl (benzyl, methylbenzyl, benzhydryl, trityl, methoxybenzyl, nitrobenzyl, etc.), $C_1-C_8$ alkylthio, $C_6-C_{12}$ arylthio (nitrophenylthio, etc.), $C_5-C_8$ cycloalkylidene, $C_1-C_8$ acyl [for example, $C_1-C_8$ alkanoyl (formyl, acetyl, chloroacetyl, trifluoroacetyl, etc.), $C_2-C_{12}$ alkoxycarbonyl (having methyl, ethyl, propyl, cyclopropylmethyl, cyclopropylethyl, isproyl, butyl, isobutyl, pentyl, hexyl, trichloroethyl, pyridylmethyl, cyclopentyl, cyclohexyl, etc. as the alkyl part), $C_8-C_{19}$ aralkoxycarbonyl (having benzyl, benzhydryl, nitrobenzyl, etc. as the aralkyl part), $C_7-C_{15}$ aroyl (benzoyl, nitrobenzoyl, etc. ), $C_3-C_{10}$ acyl of a dibasic acid (succinyl phthaloyl, etc. ), chlorosulfonyl, $C_0-C_{10}$ phosphoric acyl (dialkoxyphosphoryl, dichlorophosphoryl, etc.)], $C_3-C_9$ trialkylsilyl, $C_3-C_9$ alkoxydialkylsilyl, or the like, and $C_1$ to $C_8$ alkylidene or $C_7-C_{14}$ aralkylidene (benzylidene, methylbenzylidene, nitrobenzylidene, etc.). An acid addition salt is also an amino protected compound. One or two of the above protecting groups may bound to the amino.

The cephalosporin derivative I of the invention can be produced using any of conventional methods used in the art which generally comprise the preparation of side chain acid, 3-substituent, cephem nucleus, introduction of 7-acyl side chain and 3-substituent, deprotection, and the like. However, the compound I can be conveniently produced according to either of the following methods 1, 2 and 3 the invention.

Method 1

In the first method, a cephalosporin derivative of formula I can be prepared by introducing an acyl group into an amine of formula III:

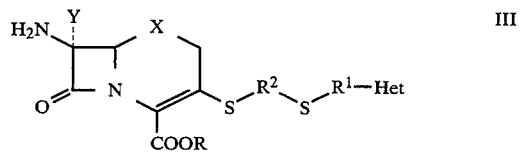

wherein Het, X, Y, $R^1$ and $R^2$ are as defined above and R is hydrogen or a carboxy-protecting group, which comprises reacting the compound of formula III or its reactive derivative with an acid of formula:

Acyl—OH wherein Acyl is optionally protected acyl, or a reactive derivative thereof to give a compound of formula II:

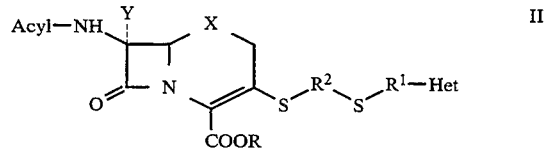

wherein Acyl, Het, X, Y, R, $R^1$ and $R^2$ are as defined above, and deprotecting the compound II. Sulfoxide of formula II are preferably reduced before deprotection.

Method 2

In the second method, a cephalosporin derivative of formula I can be prepared by reacting a compound of formula IV:

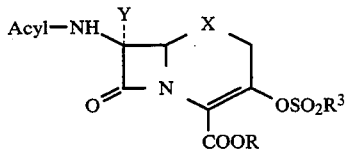

IV wherein Acyl is optionally protected acyl, $R^3$ is alkyl or aryl, and R, X and Y are as defined above, or its reactive derivative with a compound of formula:

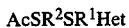

AcSR²SR¹Het wherein Ac is acyl, and Het, $R^1$ and $R^2$ are as defined above to obtain a compound of formula II, and deprotecting the compound II. As mentioned above, sulfoxide compounds of formula II are preferably reduced before deprotection.

Method 3

In the third method, a cephalosporin derivative of formula I can be prepared by reacting a compound of formula V:

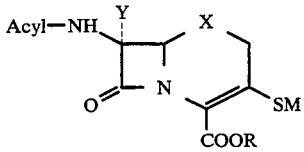

V wherein Acyl is optionally protected acyl, R, X and Y are as defined above and M is hydrogen or a heavy metal, or its reactive derivative with a compound of formula:

Hal—R²SR¹Het wherein Hal is halogen atom, Het, $R^1$ and $R^2$ are as defined above or its reactive derivative to obtain a compound of formula II, and deprotecting the compound II. Sulfoxide compounds of formula II are reduced before deprotection.

All the required starting materials for the above methods, that is, cephem nucleus, 7-side chain acid and 3-substituent, are prepared, for example, according to the processes described in the Preparations. However, the present invention does not intend to restrict use of starting compounds to those prepared by the procedures herein disclosed but any equivalent compounds prepared by known methods can be used to obtain the compound I.

The outline of each method is described below.

The starting material of the method 1, an 7-amine III and an acid, can be prepared, for example, according to the procedures described in Preparation 6, and Preparations 1 and 2, respectively.

The amidation by which an acyl group is introduced at the 7-position of cephem nucleus, can be carried out by making a carboxylic acid or reactive derivative thereof to react with a 7-amine or reactive derivative thereof. The amidation reaction can be carried out under reaction conditions well-known to the art. Thus, the amine is reacted with a slightly excess of the acid in an appropriate solvent in the presence of condensing agent at a temperature ranging from about −30° to 50° C., preferably from about −10° to 30° C. for about 10 min to 10 hr, preferably about 30 min to 2 hr.

Examples of condensing agents include carbodiimide such as N,N′-diethylcarbodiimide, N,N′-dicyclohexylcarbodiimide, and the like; carbonyl compound such as carbonyldiimidazole, and the like; isoxazolinium salt; acylamino compound such as 2-ethoxy-1-ethoxycarbonyl-1,2-dihydroquinoline; halogenated phosphoric acid; sulfonyl halide; or amidated enzyme, and the like.

Preferably, the amine is reacted with 1-2 mol of carboxylic acid in the presence of 1-2 mol of condensing agent in a solvent which does not contain an active hydrogen such as dichloromethane, chloroform, ethyl acetate, acetonitrile, or the like.

The reactive derivatives of 7-amine are cephem compound whose 7-amino group is activated with the aid of various groups, for example, silyl group such as trimethyl silyl, methoxydimethyl silyl, t-butyldimethylsilyl, and the like; stannyl group such as trimethylstannyl, and the like; alkylene group through which the amino group bind to alkanal, acetone, acetylacetone, acetoacetate ester, acetoacetoanilide, acetacetonitrile, cyclopentanedione, acetylbutylolactone, and the like to form enamine; alkylidene group such as 1-haloalkylidene, 1-haloaralkylidene, 1-alkoxyalkylidene, 1-alkoxyaralkylidene, 1-alkoxy-1-phenoxyalkylidene, alkylidene, aralkylidene, and the like; acid such as mineral acid, carboxylic acid, sulfonic acid, and the like, with which the amino group forms a salt; acyl which is easy to remove such as alkanoyl, and the like; or other $C_1$-$C_{10}$ groups useful for such purpose. Reactive derivatives of an amine also include compounds wherein functional groups other than 7-amino group have been protected.

Examples of the reactive derivatives of carboxylic acid (Acyl—OH) include symmetric or mixed anhydride [mixed acid anhydride with mineral acid (phosphoric acid, sulfuric acid, half ester of carbonic acid, and the like), organic acid (alkanoic acid, aralkanoic acid, sulfonic acid, and the like), and the like]; intramolecular anhydride (ketene, isocyanate, and the like); acid halide (mixed acid anhydride with hydrogen halide); acid halide; active ester, for example, enol ester (vinyl ester, isopropenyl ester, and the like), aryl ester (phenyl ester, halophenyl ester, nitrophenyl ester, and the like), heterocyclic ester (pyridyl ester, benzotriazolyl ester, and the like), ester of N-hydroxy compound, ester of diacylhydroxylamine (N-hydroxysuccinimidoyl ester, N-hydroxyphthalimidoyl ester, and the like), thiol ester (aralkylthiol ester, heterocyclic thiol ester, and the like); active amide (aromatic amide formed with imidazole, triazole, 2-ethoxy-1,2-dihydroquinoline, or the like, or diacylanilide), and the like.

The above-mentioned reactive derivatives of amine and/or carboxylic acid are allowed to react in the presence of acid capturing reagents, for example, inorganic bases such as oxides, hydroxides, carbonates, hydrocarbonates alkali metals or alkaline earth metals; organic bases such as tertiary amine, aromatic amine, and the like; oxiranes such as alkylene oxide, aralkylene oxide, and the like; pyridinium salts such as tripyridiniumtriazine trichloride, and the like; adsorbents such as Celite, and the like. Preferably, the amine is reacted with 1-2 mol of a reactive derivative of carboxylic acid (Acyl—OH) and 0-2 mol of an acid capturing agent in an inert solvent lacking an active hydrogen. The reaction between an enzymatic ester and an acid halide proceeds even in an aqueous solvent.

After the reaction completes, the reaction mixture is neutralized with acid, extracted with a solvent, and concentrated. The residue, when purified by, for example, recrystallization from a solvent or a column chromatography, gives a protected product II, which is then deprotected conventionally to yield the final product, the cephalosporin derivative of formula I.

The starting material of the method 2, the compound IV, can be, for example, prepared by the amidation of a corresponding compound having amino group at the 7β-position using known methods generally used for amidation, as described in the Preparation 7.

The other starting material, the acylthioalkylthio compound (Ac—$SR^2SR^1$Het) can be prepared by treating a corresponding heterocyclic thiol with sodium hydride at temperature ranging from about −30° to 30° C. in a solvent such as dimethylformamide, and the like, to give alkalimetal mercaptide, which is then reacted with halomethyl thiolcarboxylate to give the acylthioalkylthio compound.

Alternatively, alkali metal heterocyclic mercaptide is treated with, e.g., bromochloromethane, to give $ClR^2SR^1$Het which is treated with thiolcarboxylate salt to give the acylthiomethyl compound $AcSR^2SR^1$Het.

The reaction between compound IV and acylthioalkylthio compound is carried out by, preferably, reacting the compound VI with equal to excess amount, preferably 1–10 equivalent, more preferably 1–3 equivalent amount of acetyl- or benzoyl-thiomethylthio derivative in an appropriate solvent in the presence of a base such as sodium methoxide, at temperature ranging from about −90° to 50° C., Preferably from about −80° to −10° C. for about 5 min to about 20 hr, preferably about 18 min to about 7 hr.

Any organic solvents can be used with a proviso that they, are not acidic. Examples of especially preferred solvents are tetrahydrofuran, dimethylformamide, acetonitrile, dimethylacetoamide, hexamethylphosphoramide, dimethylsulfoxide, methanol, ethanol, propanol, and the like.

The method 2 is also effectively conducted by using an alkali metal thioalkylthio derivative prepared by reacting the acylthioalkylthio compound with an alkali metal alkoxide.

After the reaction completes, the reaction mixture is neutralized with acid, diluted with water, and extracted with an appropriate solvent. Examples of appropriate solvents include ethyl acetate, dichloromethane, and the like. The extract is then dried, concentrated under reduced pressure, if desired, and the residue is purified appropriately by, for example, extraction, washing, recrystallization, or a column chromatography on silica gel. Solvents for the recrystallization are toluene, ethyl acetate, acetonitrile, dichloromethane, methanol, and the like. Suitable eluents for the chromatography is a mixture of toluene and ethyl acetate. The deprotection gives the desired cephalosporin derivative of formula I.

Although the starting material of the method 3, the compound V, may be a salt of metal or organic base such as pyridine, it is preferably a salt of silver. The halogen atom of the methylthiomethyl halide may be chlorine, bromine or iodine, with a preference in iodine.

The compound V can be prepared from an appropriate starting material, for example, above compound IV, as described below. The compound IV, after sulfoxidation, if necessary, is converted into a 3-thiol, which is then reacted with a base to obtain a salt, preferable a silver salt.

The sulfoxidation is carried out by reacting the protected compound IV in an appropriate solvent with 1 to 2 mol of an oxidizing reagent, e.g., hydrogen peroxide, peracetic acid, m-chloroperbenzoic acid, and the like at a temperature ranging from about −40° to 10° C. for about 10 min to 5 hr. The reaction mixture is then treated with an aqueous solution of sodium thiosulfate, diluted with a solvent, dried, and concentrated to obtain a crude product. The crude product is purified by, for example, column chromatography on silica gel eluting with dichloromethane, chloroform, and the like, if necessary.

A 3-thiol is prepared from the 3-sulfonyloxy compound by dissolving the latter into an appropriate solvent, adding sodium hydrosulfide thereto, and allowing to react at a temperature ranging from about −40° to 0° C. for about 30 to 60 min. The mixture is neutralized with acid such as hydrochloric acid, extracted with an appropriate organic solvent such as ethyl acetate. The extract is dried and concentrated to yield the thiol. Examples of appropriate solvents are dimethylformamide, acetonitrile, and the like.

A silver salt of 3-thiol is prepared by contacting said thiol with a slightly excess silver nitrate in an appropriate solvent at a temperature from about −30° to 20° C. for about 10 to 30 min. Examples of solvents are tetrahydrofuran, dichloromethane, and the like. The silver salt is separated by, for example, diluting the reaction mixture with water, extracting the diluted solution with dichloromethane, and concentrating the extract.

The halogenated alkylthio derivative of formula: Hal—$R^2SR^1$Het can be prepared by the chloromethylation of a heterocyclic thiol with bromochloromethane in a solvent such as dimethylformamide in the presence of a base, e.g., sodium hydride. The resulting chloromethylated product is then, if necessary, subjected to an iodine replacement reaction with sodium iodide.

The reaction between the compound V and the 2-halogenated methylthio derivative is carried out in an appropriate solvent at a temperature ranging from about 0° to 30° C. for about 2 to 20 hr. Examples of appropriate solvents are hexamethylphosphoramide, dimethylformamide, and the like. The product is extracted with an organic solvent such as ethyl acetate, and the like, and the extract is concentrated. The residue is then purified by, for example, a column chromatography on silica gel.

The reduction of sulfoxide II is carried out using any reducing agents commonly used in the field of cephalosporin such as phosphorus trichloride, stannous chloride, and the like.

As the final step, the product II is deprotected to yield the cephalosporin derivative I of the invention. The deprotection is carried out according to the conventional procedures.

Deprotection of the carboxy-protecting groups can be carried out in an inert solvent using conventional method. For example, when the carboxy-protecting Group is an reactive ester-forming group, it can be removed by treating the protected product in an inert solvent with acid, base, buffer solution, ion-exchanging resin, and the like. When the carboxy-protecting group is an insufficiently reactive ester-forming group, it can be activated by known methods before deprotection. The activation is effected depending on the kind of ester as follows: trichloroethyl esters are treated with metal and acid; p-nitrobenzyl esters are treated by hydrogenation; with salts of dithionic acid; or with metal and acid;

phenacyl esters are treated by the radiation of light. Carboxy-protecting groups which are aralkyl can be removed by catalytic hydrogenation on palladium, platinum, nickel, and the like. Carboxy-protecting groups which are tertiary alkyl, cyclopropylmethyl, 2-alkenyl, aralkyl, sulfonylethyl can be removed by treating the product with acid in the presence of a cation-scavenger such as anisole, benzenethiol, and the like, if necessary. Examples of acids include mineral acids; Lewis acids such as aluminum chloride, stannic chloride, titanium tetrachloride, and the like; sulfonic acids such as benzenesulfonic acid, methanesulfonic acid, trifluoromethanesulfonic acid, and the like; strong carboxylic acids such as trifluoroacetic acid, and the like. When the carboxy-protecting group is 2-alkenyl, it can be removed by treating the product with triarylphosphine-palladium chelate compounds. When the carboxy-protecting group is phenacyl, 2-alkenyl, hydroxyaralkyl, or the like, it can be removed by treating the product with an alkali or a nucleophilic reagent. As can be understood by one of skill in the art, other equivalent methods are as well employed for the deprotection.

The protected hydroxy can conventionally be deprotected, for example, by the action of a strong carboxylic acid, Lewis acid (e.g., aluminum chloride, bis(alkylstannyl) oxide), etc., if required in the presence of a cation scavenger to cleave ether bond, by the action of acid or base to hydrolyze an ester group, etc. This reaction is usually carried out in a solvent at $-10°$ C. to $50°$ C. for 30 min to 10 hr to give the objective hydroxy compound.

The protected amino can conventionally be deprotected, for example, as follows:

a) Alkoxycarbonyl (t-butoxycarbonyl, etc.), or the like amino protecting group: by the action of a strong acid (trifluoroacetic acid, trifluoromethanesulfonic acid, etc.), Lewis acid (aluminum chloride, stannic chloride, titanium chloride, zinc chloride, etc.), and other acids, if required in the presence of a cathion scavenger (anisole, benzenethiol, etc.).

b) Aralkoxycarbonyl (carbobenzoxy, methylcarbobenzoxy, diphenylmethoxycarbonyl, etc.) or the like amino-protecting group: by the action of the said Lewis acid and cathion scavenger or by hydrogen (catalytic hydrogenation using palladium or nickel catalyst, etc.).

c) Lower alkanoyl (formyl, acetyl, chloroacetyl, etc.), Schiff base forming group (a divalent carbon group, e.g., ethylidene, propylidene, benzylidene, substituted benzylidene, etc.), aralkyl (trityl, substituted trityl, etc.), arylthio (phenylsulfenyl, etc.), tetrahydropyranyl, silyl or stannyl (trimethylstannyl, trimethylsilyl, etc.), or the like: by the action of an acid (hydrochloric acid, sulfuric acid, methanesulfonic acid, etc.), or the like.

d) Others: methods specific for each protecting group (for example, thiourea for haloacetyl or N-alkyldithiocarbamate: hydrazine for dibasic acid acyl; phosphorus pentachloride and alkanol for amide; etc.).

Above and similar deprotections are described, for example, in J. F. W. McOmie Ed., "*Protective Groups in Organic Chemistry*" p.183 (1973) PLEUM Press, New York; S. Patai, Ed., "*The Chemistry of Functional Groups*" (1969), Interscience Publ., John Wiley & Sons Ltd. London; Flynn Ed., "*Cephalosporins and Penicillins*" Academic Press, New York (1972), etc.

Thus, the present invention also provides a process for producing the compound claimed in claim 1 which comprises an introduction of 3-substituent, 4-carboxylate ester, 4-carboxylate salt or 7-acyl, reduction of sulfoxide, or deprotection. Structural varients can be obtained by the modification of cephem nuclei at, for example, 7-position, if desired.

The resulting free acid I is then converted into pharmaceutically acceptable salts, if desired, by conventional methods as described below. Such salts can be formed with the corresponding base used for medical purpose in the field of cephalosporin antibiotics, for example, light metal salts such as lithium, sodium, potassium, magnesium, calcium, or aluminium salt, which render physiologically acceptable ions. Another preferred salts are those formed with $C_1$–$C_{12}$ alkylammonium such as trimethylammonium, triethylammonium, methylmorpholinium, and the like; or $C_4$–$C_9$ aromatic bases such as pyridinium, collidinium, picolinium, quinolinium, dimethylanilinium, and the like. Furthermore, the cephalosporin derivative formula I may be protected with any of afore-mentioned $C_2$–$C_{15}$ pharmaceutically active ester-forming groups to obtain esters which show bactericidal activities on oral and parenteral administration, especially on oral administration.

Carboxylate salts of free acid I can be obtained conventionally by reacting the acid I with a base or a weak carboxylic acid salt of the base. For example, an acid I is neutralized with a base (hydroxide, carbonate or bicarbonate of a light metal), or subjected to an exchange decomposition with a salt of lower carboxylic acid (sodium acetate, sodium lactate, sodium 2-ethylhexanoate, and the like). The resulting salt can be isolated by separating out by diluting the reaction mixture with an appropriate solvent in which the salt hardly or slightly dissolves, or lyophilization.

The reaction generally completes within about 1 to 10 min at a temperature lower than about 50° C. When no side reactions are observed, the reaction may be allowed to continue for additional period.

The carboxylate salts of the compound I, when treated with acid, gives the compound of formula I. Accordingly, the present invention further provides a process for producing a compound I by treating a salt of compound I with acid.

When compound I has a basic group such as amino, it may be reacted with acid, e.g., hydrochloric acid, acetic acid, to give an acid addition salt as stated above in a manner conventional in the field of cephalosporin, e.g., by treating the compound I with about 1 to 2 moles of an acid at about 0° to 50° C. for about 10 to 90 min.

Although the above-mentioned methods 1, 2 and 3 are preferable for the production of the compound I, the present invention is not limited to compounds prepared by these methods, but all the compounds I prepared by any other methods well known to those skilled in the art fall within the scope of the present invention.

The reactions as mentioned above are carried out at temperature ranging from about $-80°$ to $100°$ C., preferably from about $-40°$ to $50°$ C. for about 10 min–20 hr, in general. When the product is stable, the reaction time can be prolonged. In the above-mentioned reactions, any of conventional techniques such as reaction solvent, anhydrous condition, inert gas introduction, stirring, and so on, are optionally included.

Examples of reaction solvents for above-mentioned methods are hydrocarbons such as pentane, hexane, octane, benzene, toluene, xylene, and the like; halogenated hydrocarbons such as dichloromethane, chloroform, carbon tetrachloride, dichloroethane, trichloroethane, chlorobenzene, and the like; ethers such as diethyl ether, methylisobutyl ether, dioxane, tetrahydrofuran, and the like; ketones such as acetone, methyl ethyl ketone, cyclohexanone, and the like; esters such as ethyl acetate, isobutyl acetate, methyl benzoate, and the like; nitro hydrocarbons such as nitromethane, nitrobenzene, and the like; nitriles such as acetonitrile, benzonitrile, and the like; amides such as formamide, acetamide, dimethylformamide, dimethylacetamide, hexamethylphosphoramide, and the like; sulfoxides such as dimethylsulfoxide, and the like; carboxylic acids such as formic acid, acetic acid, propionic acid, and the like; organic bases such as diethylamine, triethylamine, pyridine, picoline, collidine, quinoline, and the like; alcohols such as methanol, ethanol, propanol, hexanol, octanol, benzylalcohol, and the like; water; and other series of industrial solvents, or a mixture thereof.

The desired product is isolated from the reaction mixture by removing contaminants such as unreacted starting materials, by-products or solvents using conventional methods such as extraction, evaporation, washing, concentration, precipitation, filtration, drying, and the like. The isolated product is subjected to conventional work-up such as adsorption, elution, distillation, precipitation, recrystallization, chromatography, and the like, or any combinations thereof.

Although the above-mentioned methods 1, 2 and 3 are preferable for the production of the compound I, the present invention is not limited to compounds prepared by these methods, but all the compounds I prepared by any other methods well known to those skilled in the art fall within the scope of the present invention.

The compound of the invention was subjected to in vitro and in vivo experiments to determine the potency as an antibiotic. By the in vitro test, the compound I proved to be highly effective against gram-positive bacteria, for example, *Staphylococcus aureus* and *Streptococcus pyogenes*, as well as on gram-negative bacteria, for example, *Escherichia coli, Enterobacter cloacar, Pseudomonas aeruginosa, Proteus vulgaris, Proteus mirabilis, Serratia marcescens, Haemophilus influenzae, Klebsiella pneumoniae* and *Morgania morganii*.

Therefore, the present invention provides a method for combating bacteria by bringing the bacteria into contact with an effective amount of the compound I.

The in vivo absorption rate of the compound I after oral administration was determined by administering a compound of the invention to mouse and measuring the blood level. The result showed that the compound I gives a high blood level on oral administration demonstrating an excellent absorption rate.

Accordingly, the compound of formula I is an effective antibiotic by oral and parenteral administration and useful in the treatment of infections caused by a wide variety of bacteria which are sensitive to the compound I.

In a further aspect of the invention, there is provided a method for the treatment or control of bacterial infections in man, animals, perishable materials, or as disinfectant, which comprises applying an effective amount of a compound I.

The present invention also provides a pharmaceutical formulations containing, as an active ingredient, an effective amount of a compound i of formula I, a pharmaceutically acceptable salt thereof, or a hydroxy- and/or amino protected derivative thereof.

For the oral administration, the compound I can be formulated in standard formulations such as capsules, tablets, granules, powders, and suspensions together with pharmaceutically acceptable carriers, diluents or excipients. For the parenteral administration, a compound I is formulated in, for example, subcutaneously, intramuscularly, intravenouly, or intraperitoneally injectable solutions or suspensions. Furthermore, the compound of the invention can be formulated into ointment, suppository, liniment, and the like. Suitable daily dose for the compound of formula I can be between about 10 mg and about 4000 mg, preferably about 100 mg and about 2000 mg on oral administration, and about 10 mg and about 4000 mg, preferably about 50 mg and about 2000 mg on parenteral administration.

The following Examples are provided to further illustrate the present invention and are not to be construded as limiting thereof.

Abbreviations used in the Examples are explained below:
Ac=acetyl;
At=2-aminothiazol-4-yl;
Bh=diphenylmethyl;
Boc=t-butoxycarbonyl;
Et=ethyl;
Me=methyl;
Ph=phenyl;
PMB=p-methoxybenzyl;
Tr=trityl.

Preparation 1 acylthiomethyl

1) Het=1,2,3-triazole (1P1)

To a suspension of 1,2,3-triazole-4-thiol sodium salt (38 g: 309 mMol.) in dimethylformamide (150 ml) at −20° C. is added dropwise chloromethyl thiolacetate (37.4 g: 300 mMol.) over 10 minutes, and the mixture is stirred at the same temperature for 30 minutes and at room temperature for 2 hours, diluted with water and extracted with ethyl acetate. The extract is washed with water, aqueous sodium hydrogen carbonate, and water, dried over sodium sulfate, and concentrated under reduced pressure. The crystalline residue is washed with hexane, dried, and recrystallized from ether to give 4-acetylthiomethylthio-1,2,3-triazole (38.9 g). Yield: 69%. mp. 88° to 89° C.

NMR δ(CDCl$_3$) ppm: 2.36(s, 3H), 4.37(s, 2H), 6.3(brs, 1H), 7.73(s, 1H). IR ν(CHCl$_3$) cm$^{-1}$: 3430, 3152, 1693, 1131.

2) Het=1,2,4-triazole (1P4)

To a solution of 1,2,4-triazole-3-thiol (2.23 g: 22.1 mMol.) in dimethylformamide (30 ml) is added sodium hydride (60% in oil: 840 mg: 21 mMol.), and the mixture is stirred at room temperature for 10 minutes. To this solution at −50° to −60° C. is added a solution of chloromethyl thiolacerate (2.50 g: 20.1 mMol.) in dimethylformamide (5 ml), and the mixture is stirred at the same temperature for 20 minutes, mixed with another trityl chloride (6.70 g: 24 mMol.) and pyridine (1.94 ml: 24.0 mMol.), stirred under ice cooling for 28 hours, diluted with water, and extracted with ethyl acetate. The extract is washed with brine, dried over sodium sulfate, and concentrated under reduced pressure. The residue is purified by silica gel chromatography (toluene: ethyl acetate=20:1) and crystallized from ether to give 3-acetylthiomethylthio-1-trityl-1,2,4-triazole (3.37 g). Yield: 39%. Colorless crystals. mp. 124° to 125° C.

NMR δ(CDCl₃) ppm: 2.32(s, 3H), 4.50(s, 2H), 7.1–7.2(m, 6H), 7.3–7.4(m, 9H), 7.90(s, 1H). IR ν(CHCl₃) cm⁻¹: 1690, 1490, 1472, 1444, 1383, 1352, 1271, 1228, 1131.

3) Het=5-tetrazolyl (3PA3)

To a solution of tetrazole-5-thiol (3.00 g: 29.41 mMol.) in dimethylformamide (50 ml) under ice cooling is added sodium hydride (60% suspension in oil: 2.59 g: 64.75 mMol.), and the mixture is stirred under ice cooling for 5 to 6 minutes. To the mixture is added a solution of chloromethyl thiolacerate (4.39 g: 35.26 mMol.) in dimethyl-formamide (10 ml), and the mixture is stirred at room temperature for 2 hours. The reaction mixture is diluted with 10% hydrochloric acid (11 ml) and water and extracted with ethyl acetate. The extract is washed with brine, dried over sodium sulfate, filtered, and concentrated. The residue is purified by silica gel column chromatography (toluene: ethyl acetate=1:1) and the resulting residue is washed with a mixture of n-hexane and ether to give 5-acetylthiomethylthiotetrazole (2.49 g) as colorless crystals. Yield: 45%. m.p. 90° C.

NMR δ(CDCl₃) ppm: 2.42(s, 3H), 4.68(s, 2H), 8–9(brs, 1H). IR ν(CHCl₃) cm⁻¹: 3072br, 1692, 1500, 1356, 1131.

4) Het=2-pyridyl (2PA3)

To a solution of 2-mercaptopyridine (1.11 g: 9.98 mMol.) in dimethylformamide (10 ml) is added sodium hydride (400 mg: 60% dispersion in oil), and the mixture is stirred at room temperature for 2 to 3 minutes. To this reaction mixture at −30° C. is added a solution of chloromethyl thiolacerate (1.12 g: 9.00 mMol.) in dimethylformamide (2 ml), and the mixture is stirred at −20° to −30° C. for 1 hour. The reaction mixture is diluted with ethyl acetate, washed with water and brine, dried over sodium sulfate, and concentrated. The residue is purified by silica gel chromatography (toluene: ethyl acetate=20:1) to give 2-acetylthiomethylthiopyridine (1.43 g) as yellow oil. Yield: 72%.

NMR δ(CDCl₃) ppm: 2.35(s, 3H), 4.65(s, 2H), 7.03(ddd, J=7.4 Hz, J=4.9 Hz, J=1.0 Hz, 1H), 7.18(ddd, J=8.0 Hz, J=1.0 Hz, J=1.0 Hz, 1H), 7.51(ddd, J=8.0 Hz, J=7.4 Hz, J=1.8 Hz, 1H), 8.47(ddd, J=4.9 Hz, J=1.8 Hz, J=1.0 Hz, 1H). IR ν(CHCl₃) cm⁻¹: 1686, 1576, 1556, 1452, 1414, 1353, 1123, 956.

5) Het=1,2,3-triazol-4-yl: using benzoyl derivative (4P7).

1. To a suspension of 1,2,3-triazol-4-ylthiol Sodium salt (10.0 g: 81.3 mMol.) in dimethylformamide (100 ml) under ice cooling is added bromochloromethane (100 ml), and the mixture is stirred for 1 hour at the same temperature. The reaction mixture is diluted with water and extracted with ethyl acetate. The extract is washed with brine, dried over sodium sulfate, and concentrated to give 4-chloromethylthio-1,2,3-triazole (10.21 g) as colorless crystals. Yield: 84%. mp. 79° to 80° C.

NMR δ(CDCl₃) ppm: 4.93(s, 2H), 7.91(s, 1H), 9.6–10.2(brs, 1H). IR ν(Nujol) cm⁻¹: 3140, 1499, 1393, 1246, 1230, 1117, 1002.

2. To a solution of thiobenzoic acid (470 mg: 3.4 mMol.) in dimethylformamide (1 ml) under ice cooling are added sodium hydride (136 mg: 3.4 mMol.: 60% dispersion in oil) and then after 10 minutes, 4-chloromethyl-thio-1,2,3-triazole (449 mg: 3 mMol.), and the mixture is stirred under ice cooling for 10 minutes and at room temperature for 4 hours. The reaction mixture is diluted with water and extracted with ethyl acetate. The extract is washed with aqueous 5% sodium hydrogen carbonate, dried over sodium sulfate, and concentrated. The residue is purified by silica gel chromatography (toluene: ethyl acetate=5:1) to give 4-benzoylthiomethylthio-1,2,3-triazole (417 mg). Yield: 55%. Recrystallization of this product from a hexane-ether mixture gives colorless needles of mp. 72.5° to 73.5° C.

NMR δ(CDCl₃) ppm: 4.57(s, 2H), 7.4–7.65(m, 3H), 7.75(s, 1H), 7.9–7.96(m, 1H). IR ν(CHCl₃) cm⁻¹: 3425, 3146, 1667, 1206, 1175, 911.

Preparation 2 chloromethyl

1) Het=trityl-1,2,4-triazol-3-yl (4P6)

To a solution of 1,2,4-triazol-3-ylthiol (10.0 g: 99 mMol.) in dimethylformamide (100 ml) under ice cooling is added sodium hydride (60% dispersion in oil: 3.96 g: 99 mMol.), and the mixture is stirred at the same temperature for 10 minutes to give sodium 1,2,4-triazol-3-yl-mercaptide, mixed with bromochloromethane (100 ml), and stirred at the same temperature for 14 hours. The reaction mixture is diluted with ethyl acetate, washed with brine, dried over sodium sulfate, and concentrated. To a solution of the residue, 3-chloromethylthio-1,2,4-triazole, in dimethylformamide (100 ml) are added under ice cooling trityl chloride (27.6 g: 99 mMol.) and triethylamine (13.8 ml), and the mixture is stirred for 30 minutes under ice cooling. The reaction mixture is diluted with water and extracted with ethyl acetate. The extract is washed with brine, dried over sodium sulfate, and concentrated. The residue is crystallized from ether to give trityl-3-chloromethylthio-1,2,4-triazole (20.2 g) as white crystals. Yield: 52%. mp. 121° to 122° C.

NMR δ(CDCl₃) ppm: 5.18(s, 2H), 7.1–7.2(m, 6H), 7.3–7.4(m, 9H), 7.95 (s, 1H). IR ν(CHCl₃) cm⁻¹: 1599, 1492, 1472, 1445, 1389, 1365, 1353, 1325.

2) Het=1-methyl-1,2,4-triazol-3-yl & 2-methyl-1,2,4-triazol-3-yl (4P4)

1. To a mixture of 1,2,4-triazol-3-ylthiol (10.1 g: 0.10 Mol.) and p-methoxybenzyl chloride (17.2 g: 0.11 Mol.) in dichloromethane (50 ml) is added a mixture of aqueous 1N-sodium hydroxide (105 ml) and tetra-butylammonium bromide (750 mg: 2.3 mMol.), and the mixture is stirred at room temperature for 16 hours. The reaction mixture is extracted with ethyl acetate. The extract is washed with brine, dried over sodium sulfate, and concentrated. The residue is crystallized from toluene to give 3-p-methoxybenzylthio-1,2,4-triazole (16.71 g) as colorless crystals. Yield: 76%. mp. 100° to 101° C.

NMR δ(CDCl₃) ppm: 3.77(s, 3H), 4.32(s, 2H), 6.79–6.83, 7.23–7.27 (A2B2, 4H), 7.0–7.8(brs, 1H), 8.13(s, 1H). IR ν(CHCl₃) cm⁻¹: 3400, 3120br, 1611, 1512, 1485, 1465, 1441, 1302.

2. To a solution of 3-p-methoxybenzylthio-1,2,4-triazole (10.0 g: 45.2 mMol.) in methanol (100 ml) is added under ice cooling a solution of diazomethane in ether (prepared from 15 g of N-nitrosomethylurea), and the mixture is stirred for 1 hour. The reaction mixture is concentrated and purified by Lobar column chromatography (toluene: ethyl acetate=1:2 to 1:3) to give 3-p-methoxybenzylthio-2-methyl-1,2,4-triazole [5.17 g: NMR δ(CDCl₃) ppm: 3.63(s, 3H), 3.79(s, 3H), 4.34(s, 2H), 6.80–6.84, 7.19–7.24(A2B2, 4H), 7.88(s, 1H). IR ν(CHCl₃) cm⁻¹: 1611, 1511, 1476, 1464, 1440, 1360, 1302. Yield: 49%] and 3-p-methoxybenzylthio-1-methyl-1,2,4-triazole [3.60 g: NMR δ(CDCl₃) ppm: 3.78(s, 3H), 3.87(s, 3H), 4.31(s, 2H), 6.80–6.85, 7.30–7.34(A2B2, 4H), 7.99(s, 1H). IR ν(CHCl₃) cm⁻¹: 1612, 1512, 1465, 1440, 1421, 1356, 1302. Yield: 34%].

3. To a solution of 3-P-methoxybenzylthio-2-methyl-1,2,4-triazole (5.09 g: 21.7 mMol.) in a mixture of dichloromethane (40 ml) and methanol (40 ml) is added silver perchlorate (5.90 g: 25.9 mMol.), and the mixture is stirred at room temperature for 1.5 hours. The reaction mixture is diluted with methanol (100 ml) and resulting crystals of 3- argentiothio-2-methyl-1,2,4-triazole is collected by filtration, washed with methanol, and dried. To a suspension of this product in dimethylformamide (40 ml) are added bromochloromethane (40 ml) and lithium chloride (2.82 g: 65.2 mMol.), and the mixture is stirred for 22 hours at room temperature. The reaction mixture is mixed with saturated brine and ethyl acetate and filtered to remove insoluble material. The organic layer is taken, washed with brine, dried over sodium sulfate, and concentrated. The residue is purified by silica gel chromatography (toluene: ethyl acetate=4:1) to give 3-chloromethylthio-2-methyl-1,2,4-triazole (1.62 g) as colorless oil. Yield: 46%.

NMR δ(CDCl₃) ppm: 3.87(s, 3H), 5.19(s, 2H), 7.96(s, 1H). IR ν(CHCl₃) cm⁻¹: 1479, 1395, 1360.

4. To a solution of 3-p-methoxybenzylthio-1-methyl-1,2,4-triazole (3.55 g: 15.1 mMol.) in a mixture of dichloromethane (30 ml) and methanol (30 ml) is added silver perchlorate (4.11 g: 18.1 mMol.), and the mixture is stirred at room temperature for 1.5 hours. The reaction mixture is diluted with methanol (100 ml) and resulting crystals of 3- argentiothio-1-methyl-1,2,4-triazole are collected by filtration, washed with methanol, and dried. To a solution of this product in dimethylformamide (30 ml) are added bromochloromethane (30 ml) and lithium chloride (1.96 g: 45.3 mMol.), and the mixture is stirred at room temperature for 21 hours. To the reaction mixture are added brine and ethyl acetate and filtered to remove insoluble material. The organic layer is taken, washed with brine, dried over sodium sulfate, and concentrated. The residue is purified by silica gel chromatography (toluene: ethyl acetate=2:1) to give 3-chloromethylthio-1-methyl-1,2,4-triazole (1.05 g) as colorless oil. Yield: 43%.

NMR δ(CDCl₃) ppm: 3.93(s, 3H), 5.21(s, 2H), 8.06(s, 1H). IR ν(CHCl₃) cm⁻¹: 1509, 1471, 1424, 1392, 1359.

3) Het=1,2,3-thiadiazolyl (3PA1-1)

To a solution of 1,2,3-thiadiazole-5-thiol sodium salt dihydrate (Purity: 70.9%: 2.50 g: 10.07 mMol.) in dimethylformamide (20 ml) is added under ice cooling bromochloromethane (20 ml) in one portion, and the mixture is stirred under ice cooling for 1.5 hours. The reaction mixture is diluted with water and extracted with ethyl acetate. The extract is washed with brine, dried over sodium sulfate, filtered, and concentrated. The residue is purified by silica gel column chromatography (toluene: ethyl acetate=20:1) to give 5-chloromethylthio-1,2,3-thiadiazole (1.60 g) as colorless oil. Yield: 95%.

NMR δ(CDCl₃) ppm: 4.93(s, 2H), 8.69(s, 1H). IR ν(CHCl₃) cm⁻¹: 1419, 1395, 1256, 1102.

4) Het=1,3,4-thiadiazol-2-yl (2PA1-1)

To a solution of 1,3,4-thiadiazole-2-thiol (4.72 g: 40 mMol.) in dimethylformamide (80 ml) is added under ice cooling sodium hydride (60% dispersion in oil: 1.76 g: 1.1 equivalents: 44 mMol.) in portions, and the mixture is stirred for 15 minutes. To the resulting solution is added bromochloromethane (80 ml), and the mixture is stirred at the same temperature for another 2 hours. The reaction mixture is diluted with water and extracted with ethyl acetate. The extract is washed with brine, dried over sodium sulfate, and concentrated. The residue is purified by silica gel chromatography (toluene: ethyl acetate=20:1) to give 2-chloromethylthio-1,3,4-thiadiazole (6.05 g) as colorless oil. Yield: 91%.

NMR δ(CDCl₃) ppm: 5.32(s, 2H), 9.16(s, 1H). IR ν(CHCl₃) cm⁻¹: 1389, 1373, 1232, 1061.

5) Het=2-methyl-1,3,4-thiadiazol-5-yl (2PA1-2)

To a solution of 2-methyl-1,3,4-thiadiazole-5-thiol (2.64 g: 20 mMol.) in dimethylformamide (40 ml) is added under ice cooling sodium hydride (880 mg: 60% dispersion in oil: 1.1 equivalents: 22 mMol.) in portions, and the mixture is stirred for 10 minutes. To the resulting solution is added bromochloromethane (40 ml), and the mixture is stirred at the same temperature for another 1 hour and 30 minutes. The reaction mixture is diluted with water and extracted with ethyl acetate. The extract is washed with brine, dried over sodium sulfate, and purified by silica gel chromatography (toluene: ethyl acetate=10:1) to give 5-chloromethylthio-2-methyl-1,3,4-thiadiazole (3.3 g) as colorless oil. Yield: 91%.

NMR δ(CDCl₃) ppm: 2.79(s, 3H), 5.24(s, 2H). IR ν(CHCl₃) cm⁻¹: 1430, 1392, 1380, 1232, 1189.

6) Het=1-methyl-5-tetrazolyl (3PA1-2)

To a solution of 1-methyltetrazole-5-thiol sodium salt (2.00 g: 14.5 mMol.) in dimethylformamide (20 ml) under ice cooling is added bromochloromethane (20 ml) in one portion, and the mixture is stirred for 1.5 hour. The reaction mixture is diluted with water and extracted with ethyl acetate. The extract is washed with brine, dried over sodium sulfate, filtered, and concentrated. The residue is purified by silica gel column chromatography (toluene: ethyl acetate=20:1–10:1) to give 5-chloromethylthio-1-methyltetrazole as colorless crystals (1.73 g). Yield: 72%. m.p. 55° to 56° C.

NMR δ(CDCl₃) ppm: 4.03(s, 3H), 5.29(s, 2H). IR ν(CHCl₃) cm⁻¹: 1467, 1408, 1384, 1278, 1235, 1171.

7) Het=2-methyltetrazol-5-yl (4P5)

1. To a solution of 5-p-methoxybenzylthiotetrazole (7.00 g: 31.5 mMol.) in methanol (150 ml) is added under ice cooling a solution of diazomethane in ether (produced from 14 g of N-nitrosomethylurea), and the mixture is stirred for 1 hour and then concentrated. The residue is purified by Lobar column chromatography (toluene: ethyl acetate=5:1) to give 5-p-methoxybenzylthio-2-methyltetrazole [4.86 g: NMR δ(CDCl₃) ppm: 3.78(s, 3H), 4.29(s, 3H), 4.38(s; 2H), 6.81–6.85, 7.30–7.34 (A2B2, 4H). IR ν(CHCl₃) cm⁻¹: 1611, 1512, 1390, 1324, 1303. colorless oil. Yield: 65%] and 5-p-methoxybenzylthio-1-methyltetrazole [2.71 g: NMR δ(CDCl₃) ppm: 3.79(s, 3H), 3.80(s, 3H), 4.49(s, 2H), 6.82–6.86, 7.27–7.31(A2B2, 4H). IR ν(CHCl₃) cm⁻¹: 1613, 1513, 1465, 1305. colorless crystals. Yield: 36%].

2. To a solution of 5-p-methoxybenzylthio-2-methyltetrazole (4.86 g: 20.59 mMol.) in a mixture of dichloromethane (40 ml) and methanol (40 ml) is added Silver perchlorate (6.17 g: 26.78 mMol.), and the mixture is stirred at room temperature for 2 hours. The reaction mixture is diluted with methanol (100 ml) and resulting crystals of 5-argentiothio- 2-methyltetrazole are collected by filtration, washed with methanol, and dried. To a solution of this product in dimethylformamide (40 ml) are added bromochloromethane (40 ml) and lithium chloride (2.67 g: 61.7 mMol.), and the mixture is stirred at room temperature for 20 hours. The reaction mixture is mixed with saturated brine and ethyl acetate and filtered to remove insoluble material. The organic layer is taken, washed with brine, dried over sodium sulfate, and concentrated. The residue is purified by silica gel chromatography (toluene: ethyl acetate=20:1) to give 5-chloromethylthio-2-methyltetrazole (1.91 g) as colorless oil. Yield: 56%.

NMR δ(CDCl$_3$) ppm: 4.37(s, 3H), 5.23(s, 2H). IR ν(CHCl$_3$) cm$^{-1}$: 1440, 1422, 1410, 1395, 1325.

Preparation 3 Substitution with iodine

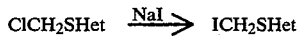

1) Het=1-methyl-1,2,4-triazol-3-yl (4P4)

To a solution of 3-chloromethylthio-1-methyl-1,2,4-triazole (981 mg: 6.0 mMol.) in acetone (10 ml) is added sodium iodide (1.78 g: 12 mMol.), and the mixture is stirred at 50° C. for 3 hours. The reaction mixture is diluted with water and extracted with ethyl acetate. The extract is washed with water, dried over sodium sulfate, and concentrated to give 3-iodomethylthio-1-methyl-1,2,4-triazole (1.50 g) as yellow oil.

NMR δ(CDCl$_3$) ppm: 3.94(s, 3H), 4.75(s, 2H), 8.07(s, 1H).

2) Het=2-methyl-1,2,4-triazol-3-yl (4P4)

To a solution of 3-chloromethylthio-2-methyl-1,2,4-triazole (981 mg: 6.0 mMol.) in acetone (10 ml) is added sodium iodide (1.78 g: 12.0 mMol.), and the mixture is stirred at 50° C. for 3 hours. The reaction mixture is diluted with water and extracted with ethyl acetate. The extract is washed with water, dried over sodium sulfate, and concentrated to give 3-iodomethylthio-2-methyl-1,2,4-triazole (1.47 g) as yellow oil.

NMR δ(CDCl$_3$) ppm: 3.84(s, 3H), 4.71(s, 2H), 7.98(s, 1H).

3) Het=1,2,3-thiadiazol-5-yl (3PA2-1)

To a solution of 5-chloromethylthio-1,2,3-thiadiazol (999 mg: 6.00 mMol.) in acetone (10 ml) is added sodium iodide (1.78 g: 12.00 mMol.), and the mixture is stirred at 50° C. for 2 hours. After cooling, the reaction mixture is diluted with water and extracted with ethyl acetate. The extract is washed once with water, dried over sodium sulfate, filtered, and concentrated to give 5-iodomethylthio-1,2,3-thiadiazole as brown oil (1.55 g).

NMR δ(CDCl$_3$) ppm: 4.53(s, 2H), 8.62(s, 1H).

4) Het=1,3,4-thiadiazol-2-yl (2PA2-1)

To a solution of 2-chloromethylthio-1,3,4-thiadiazole (849 mg: 5.1 mMol.) in acetone (10 ml) is added sodium iodide (1.5 g: 2.0 equivalents: 10 mMol.), and the mixture is stirred at 50° C. for 3 hours. After cooling, the reaction mixture is diluted with water and extracted with ethyl acetate. The extract is washed with water, dried over sodium sulfate, and concentrated to give 2-iodomethylthio-1,3,4-thiadiazole (1.2 g, containing ca. 10% of the starting chloromethyl compound) as yellow oil.

NMR δ(CDCl$_3$) ppm: 4.85(s, 2H), 9.14(s, 1H).

5) Het=2-methyl-1,3,4-thiadiazol-5-yl (2PA2-2)

To a solution of 5-chloromethylthio-2-methyl-1,3,4-thiadiazole (730 mg: 4 mMol.) in acetone (6 ml) is added sodium iodide (1.2 g: 2.0 equivalents: 8 mMol.), and the mixture is stirred at 55° C. for 2 hours. The reaction mixture is diluted with water and extracted with ethyl acetate. The extract is washed with water, dried over sodium sulfate and concentrated to give 5-iodomethylthio-2-methyl-1,3,4-thiadiazole (1.05 g) as yellow oil.

NMR δ(CDCl$_3$) ppm: 2.79(s, 3H), 4.78(s, 2H).

6) Het=1-methyltetrazol-5-yl (3PA2-2)

To a solution of 5-chloromethylthio-1-methyltetrazole (987 mg: 6.0 mMol.) in acetone (10 ml) is added sodium iodide (1.78 g: 12.0 mMol.), and the mixture is stirred at 50° C. for 3 hours. After cooling, the reaction mixture is diluted with water and extracted with ethyl acetate. The extract is washed with water, dried over sodium sulfate, filtered, and concentrated to give 5-iodomethylthio-1-methyltetrazole as yellow oil (1.33 g: containing about 20 Mol. % of the chloride).

NMR δ(CDCl$_3$) ppm: 3.98(s, 3H), 4.76(s, 2H).

7) Het=2-methyltetrazol-5-yl (4P5 part 3)

To a solution of 5-chloromethylthio-2-methyltetrazole (987 mg: 6.0 mMol.) in acetone (10 ml) is added sodium iodide (1.78 g: 12.00 mMol.), and the mixture is stirred at 50° C. for 3 hours. The reaction mixture is diluted with water and extracted with ethyl acetate. The extract is washed with water, dried over sodium sulfate, and concentrated to give 5-iodomethylthio-2-methyltetrazole (1.43 g) as yellow oil.

NMR δ(CDCl$_3$) ppm: 4.38(s, 3H), 4.74(s, 2H).

Preparation 4 Modification at Het

1) Introduction of trityl giving trityl-1,2,3-triazol-4-yl (1P2)

To a suspension of 1,2,3-triazol-4-thiol sodium salt (109 g: 870 mMol.) in dimethylformamide (300 ml) is added dropwise at −20° to −30° C. chloromethyl thiolacerate (109 g: 870 mMol.), and the mixture is stirred at room temperature for 2 hours. To the reaction mixture are added under ice cooling trityl chloride (292 g; 1.05 Mol.) and pyridine (84.6 ml: 1.05 Mol.), and the mixture is stirred at room temperature for 18 hours, diluted with dichloromethane, washed with brine, dried over sodium sulfate, and concentrated under reduced pressure. The residue is crystallized from ether to give 4-acetylthiomethylthio-1-trityl-1,2,3-triazole (183 g). Yield: 49%. mp: 115° to 116° C. Colorless crystals.

NMR δ(CDCl$_3$) ppm: 2.29(s, 3H), 4.34(s, 2H), 7.05–7.15(m, 6H), 7.3–7.4(m, 9H), 7.47 (s, 1H). IR ν(CHCl$_3$) cm$^{-1}$: 1688, 1488, 1442, 1199, 1128, 1072, 1033, 954.

2) Introduction of methyl giving ($\frac{1}{2}$)-methyl-1,2,3-triazol-4-yl (1P3)

To a solution of 4-acetylthiomethylthio-1,2,3-triazole (6 g: 31.75 mMol.) in tetrahydrofuran (30 ml) is added dropwise at −78° C. a solution of 1M lithium bis(trimethylsilyl)amide in tetrahydrofuran (35 ml: 35 mMol.), and the mixture is stirred at the same temperature for 5 minutes and added methyl trifluoromethanesulfonate (4.0 ml: 35 mMol.). After stirring at the same temperature for 2 hours, the reaction mixture is diluted with 10% hydrochloric acid (26 ml) and water, and extracted with ethyl acetate. The extract is washed with aqueous sodium hydrogen carbonate and brine, dried over sodium sulfate, and concentrated. The residue is purified by silica gel chromatography (n-hexane: ethyl acetate=1:2) to give 4-acetylthiomethylthio-3-methyl-1,2,3-triazole [2.22 g; NMR δ(CDCl$_3$) ppm: 2.32(s, 3H), 4.13(s, 5H), 7.77(s, 1H). IR ν(CHCl$_3$) cm$^{-1}$: 1698, 1429, 1355, 1263, 1226, 1205, 1127, 1100, 957. mp. 37°–38° C. Yield: 34%], 4-acetylthiomethylthio-1-methyl-1,2,3-triazole [884 mg; NMR δ(CDCl$_3$) ppm: 2.35(s, 3H), 4.11(s, 3H), 4.33(s, 2H), 7.59(s, 1H). IR ν(CHCl13) cm−1: 1691, 1434, 1354, 1285, 1131, 1106, 1048, 1031, 956. mp. 71°–72° C. Yield: 14%], and 4-acetylthiomethylthio-2-methyl-1,2,3-triazole [175 mg; NMR δ(CDCl13) ppm: 2.35 (s, 3H), 4.20(s, 3H), 4.30(s, 2H), 7.56(s, 1H). IR ν(CHCl3) cm⁻¹: 1691, 1446, 1369, 1130, 1006, 990, 956. Oil. Yield: 3%].

Preparation 5 Introduction of 7-acyl

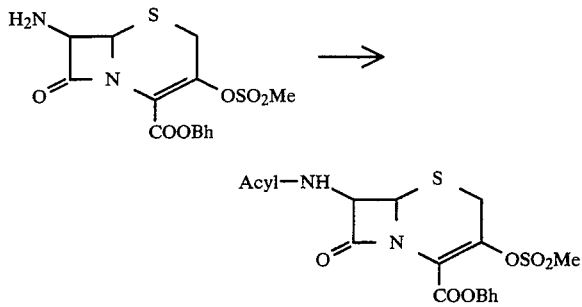

1) Acyl=(Z)-2-(2-t-butoxycarbonylaminothiazol-4-yl)-2-pentenoyl (4P10-1)

To a suspension of 7β-amino-3-methanesulfonyloxy-3-cephem-4-carboxylic acid diphenylmethyl ester hydrochloride (1.49 g: 3 mMol.) and (Z)-2-(2-t-butoxycarbonylaminothiazol-4-yl)-2-pentenoic acid (1.03 g: 3.45 mMol.) in dichloromethane (30 ml) is added at −30° C. N-methylmorpholine (1.1 ml : 10 mMol.) and, after 2 minutes, phenyl dichlorophosphate (0.49 ml: 3.27 mMol.), and the mixture is stirred at the same temperature for 1 hour and 20 minutes. The reaction mixture is mixed with 1N-hydrochloric acid (6 ml) and extracted with ethyl acetate. The extract is washed with water, aqueous 5% sodium hydrogen carbonate, and brine, dried over sodium sulfate, and concentrated. The residue (2.6 g) is dissolved in hot isopropanol (100 ml), cooled, and the separating pale yellow powder is collected by filtration to give 7β-[(Z)-2-(2-t-butoxycarbonylaminothiazol-4-yl)-2-pentenoylamino]-3-methanesulfonyloxy-3-cephem-4-carboxylic acid diphenylmethyl ester (2.01 g). Yield: 91%.

NMR δ(CDCl3) ppm: 1.12(t, J=7.6 Hz, 3H), 1.54(s, 9H), 2.5–2.7(m, 2H), 2.85(s, 3H), 3.55, 3.80(ABq, J=18 Hz, 2H), 5.09(d, J=5 Hz, 1H), 5.95(dd, J=5 Hz, J=8 Hz, 1H), 6.45(t, J=7.4 Hz, 1H), 6.74(s, 1H), 6.86(s, 1H), 7.2–7.5(m, 10H), 7.80(d, J=8 Hz, 1H). IR ν(CHCl3) cm⁻¹: 3400, 1786, 1725, 1669, 1545, 1367, 1287, 1220, 1156.

2) Acyl=(Z)-2-(2-t-butoxycarbonylaminothiazol-4-yl)-2-trityloxyimino-acetyl (1P5)

To a suspension of (Z)-2-(2-t-butoxycarbonylaminothiazol-4-yl)-2-trityloxyiminoacetic acid (41.7 g: 78.8 mMol.) in dichloromethane (600 ml) is added at −30° C. N-methylmorpholine (7.575 g: 75 mMol.), and the mixture is stirred for 10 minutes, mixed with 7β-amino-3-methanesulfonyloxy-3-cephem-4-carboxylic acid diphenylmethyl ester hydrochloride (37.27 g: 75 mMol.), is stirred at the same temperature for 50 minutes, mixed with 1-ethyl-3-(3-dimethylaminopropyl)carbodiimide hydrochloride (14.38 g: 75 mMol.), stirred under ice cooling for 3 hours, diluted with water, and extracted with ethyl acetate. The extract is washed with water, dried, and concentrated under reduced pressure. The residue is purified by silica gel chromatography (toluene containing 0.5% acetic acid: ethyl acetate=10:1) and the eluate is treated with etherhexane to give 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (57.42 g). Colorless powder. Yield: 79%. This product contains ca. 5% of the 2-cephem isomer.

NMR δ(CDCl3) ppm: 1.48(s, 9H), 2.78(s, 3H), 3.45, 3.76(ABq, J=18.6 Hz, 2H), 5.13(d, J=5 Hz, 1H), 6.06(dd, J=5 Hz, J=8.8 Hz, 1H), 6.96(s, 1H), 7.02(s, 1H), 7.2–7.5(m, 26H). IR ν(CHCl3) cm⁻¹: 3400, 1793, 1724, 1690, 1543, 1513, 1493, 1445, 1368, 1285, 1222, 1157.

3) Acyl=(Z)-2-(2-t-butoxycarbonylaminothiazol-4yl)-2-trityloxyiminoacetyl (1P6)

To a suspension of 7β-amino-3-methanesulfonyloxy-3-cephem-4-carboxylic acid diphenylmethyl ester hydrochloride (37.27 g: 75 mMol.) and (Z)-2-(2-t-butoxycarbonylaminothiazol-4-yl)-2-trityloxyiminoacetic acid (45.63 g; 86 mMol.) in dichloromethane (600 ml) is added at −30° C. N-methylmorpholine (27.2 ml: 0.25 Mol.) over 3 minutes. After 4 minutes, phenyl dichlorophosphate (12.3 ml: 82 mMol.) is added to the mixture. After stirring over 3 hours, the mixture is diluted with 10% hydrochloric acid (40 ml) and water and extracted with ethyl acetate. The extract is washed with water, aqueous sodium hydrogen carbonate, dilute hydrochloric acid, and water, dried over sodium sulfate, and concentrated under reduced pressure. The residue is dissolved in isopropanol (2 liters) by warming and cooled to give 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (67 g). Colorless powder. Yield: 92%.

4) Acyl=(Z)-2-(2-t-butoxycarbonylaminothiazol-4-yl)-2-methoxyimino-acetyl (3PB-1)

To a suspension of 7β-amino-3-methanesulfonyloxy-3-cephem-4-carboxylic acid diphenylmethyl ester hydrochloride (994 mg: 2 mMol.) and (Z)-2-(2-t-butoxycarbonylaminothiazol-4-yl)-2-methoxyiminoacetic acid (662 mg: 2.2 mMol.) in dichloromethane (16 ml) is added at −30° C. N-methylmorpholine (0.72 ml: 6.6 mMol.) and phenyl dichlorophosphate (0.33 ml: 2.2 mMol.), and the mixture is stirred at the same temperature for 2.5 hours. The reaction mixture is quenched by adding 10% hydrochloric acid (5 ml) and extracted with ethyl acetate. The extract is washed with water, 5% aqueous sodium hydrogen carbonate, and water, dried over sodium sulfate, and concentrated. The residue is purified by silica gel chromatography (toluene: ethyl acetate=2:1 containing 0.5% of acetic acid) to give 7β-[(Z)-2-(2-t-butoxycarbonylaminothiazol-4-yl)-2-methoxyiminoacetyl]amino-3-methanesulfonyloxy-3-cephem-4-carboxylic acid diphenylmethyl ester (1.07 g). Yield: 72%.

NMR δ(CDCl3) ppm: 1.53(s, 9H), 2.83(s, 3H), 3.63, 3.88(ABq, J=19 Hz, 2H), 4.09(s, 3H), 5.18(d, J=5 Hz, 1H), 6.04 (dd, J=5 Hz, J=9 Hz, 1H), 6.95 (s, 1H), 7.2–7.5(m, 13H).

5) Acyl=(Z)-2-(2-t-butoxycarbonylaminothiazol-4-yl)-2-cyclopentyl-oxyiminoacetyl (4P10-3)

To a suspension of 7β-amino-3-methanesulfonyloxy-3-cephem-4-carboxylic acid diphenylmethyl ester hydrochloride (1.49 g: 3 mMol.) and (Z)-2-(2-t-butoxycarbonylaminothiazol-4-yl)-2-cyclopentyloxyimino-acetic acid (1.23 g: 3.5 mMol.) in dichloromethane (30 ml) at −30° C. are added N-methylmorpholine (1.1 ml: 10 mMol.) and, after 1 minute, phenyl dichlorophosphate (0.49 ml: 3.3 mMol.), and the mixture is stirred at the same temperature for 2 hours. The reaction mixture is mixed with 1N-hydrochloric acid (6 ml) and water (50 ml) and extracted with ethyl acetate. The extract is washed with water, 5% aqueous sodium hydrogen carbonate, and water, dried over sodium sulfate, and purified by silica gel chromatography (toluene: ethyl acetate=5:1, containing 0.5% acetic acid) to give 7β-[(Z)-2-(2-t-butoxycarbonylaminothiazol-4-yl)-2-cyclopentyloxyiminoacetamido]-3-methanesulfonyloxy-3-cephem-4-carboxylic acid diphenylmethyl ester ( 1.86 g) as white foam. Yield: 78%.

NMR δ(CDCl₃) ppm: 1.53(s, 9H), 1.3–2.0(m, 8H), 2.80(s, 3H), 3.61, 3.88(ABq, J=19 Hz, 2H), 4.9–5.0(m, 1H), 5.17(d, J=5 Hz, 1H), 6.04(dd, J=5 Hz, J=9 Hz, 1H), 6.96(s, 1H), 7.3–7.5(m, 12H), 8.6(brs, 1H). IR ν(CHCl₃) cm⁻¹: 3400, 1792, 1724, 1685, 1543, 1367, 1226, 1220, 1158.

6) Acyl=(Z)-2-(2-t-butoxycarbonylaminothiazol-4-yl)-2-(2-propenyloxyimino) acetyl (4P10-2)

To a suspension of 7β-amino-3-methanesulfonyloxy-3-cephem-4-carboxylic acid diphenylmethyl ester hydrochloride (1.49 g: 3 mMol.) and (Z)-2-(2-t-butoxycarbonylaminothiazol-4-yl)-2-(2-propenyloxyimino)-acetic acid (1.13 g: 3.46 mMol.) in dichloromethane (30 ml) at −30° C. are added N-methylmorpholine (1.1 ml: 10 mMol.), and after 1 minute, phenyl dichlorophosphate (0.49 ml: 3.27 mMol.), and the mixture is stirred at the same temperature for 2 hours. The reaction mixture is mixed with 3N-hydrochloric acid (6 ml) and water (30 ml) and extracted with ethyl acetate. The extract is washed with water, 5% aqueous sodium hydrogen carbonate, and water, dried over sodium sulfate, and purified by silica gel chromatography (toluene: ethyl acetate=5:1, containing 0.5% of acetic acid) to give 7β-[(Z)-2-(2-t-butoxycarbonylaminothiazol-4-yl)-2-(2-propenyloxyimino)acetamido]-3-methanesulfonyl-oxy-3-cephem-4-carboxylic acid diphenylmethyl ester (1.83 g) as pale yellow foam. Yield: 79%.

NMR δ(CDCl₃) ppm: 1.53(s, 9H), 2.82(s, 3H), 3.61, 3.86(ABq, J=20 Hz, 2H), 4.80(d, J=6 Hz, 2H), 5.17(d, J=5 Hz, 1H), 5.23–5.40(m, 2H), 5.94–6.13(m, 2H), 6.95(s, 1H), 7.2–7.5(m, 12H), 8.6(brs, 1H). IR ν(CHCl₃) cm⁻¹: 3400, 1792, 1725, 1686, 1544, 1367, 1286, 1223, 1219, 1160.

Preparation 6 7-Side chain acid 1) (Z)-2-(2-t-butoxycarbonylaminothiazol-4-yl)-2-trityloxyiminoacetic acid (4P1: BocATtr)

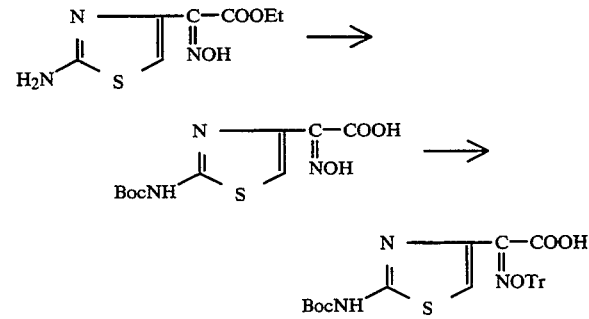

1. To a suspension of (Z)-2-(2-aminothiazol-4-yl)-2-hydroxyiminoacetic acid ethyl ester (86 g: 0.4 Mol.) in dichloromethane (1200 ml) are added 4-dimethylaminopyridine (9.6 g: 79 mMol.) and then di-t-butyl dicarbonate (240 ml: 1.04 Mol.) dropwise at room temperature, and the mixture is stirred for 19 hours. The reaction mixture is mixed with 0.5N-hydrochloric acid (500 ml) and the dichloromethane layer is taken. The organic layer is washed with brine, dried over sodium sulfate, and concentrated. The residue is diluted with ethanol (200 ml) and concentrated again. To a solution of the residue in ethanol (300 ml) under ice cooling is added dropwise a solution of sodium hydroxide (64 g: 1.6 Mol.) in water (300 ml), and the mixture is stirred under ice cooling for 30 minutes and at room temperature for 19 hours. The reaction mixture is mixed with concentrated hydrochloric acid (140 ml) and ice water (1000 ml) and extracted with ethyl acetate. The extract is washed with water, dried over sodium sulfate, and concentrated. The resulting crystalline residue is washed with water, dried, and washed with ether to give (Z)-2-(2-t-butoxycarbonylaminothiazol-4-yl)-2-hydroxyiminoacetic acid (86.3 g) as colorless crystals, mp. 170° to 173° C. (decomposition).

NMR δ(CDCl₃-CD₃SOCD₃) ppm: 1.55(s, 9H), 7.38(s, 1H). IR ν(Nujol) cm−1: 3640, 3510, 3125, 2520br, 1730, 1635, 1600, 1530, 1295, 1165, 1000.

2. To a solution of (Z)-2-(2-t-butoxycarbonylaminothiazol-4-yl)-2-hydroxyiminoacetic acid (86.3 g: 0.30 Mol.) in dimethylformamide (600 ml) are added potassium carbonate (92 g: 0.67 Mol.) and triphenylmethyl chloride (100 g: 0.36 Mol.), and the mixture is stirred at room temperature for 3 days. The reaction mixture is poured into a mixture of concentrated hydrochloric acid (111 ml) and ice water (1500 ml) and extracted with ethyl acetate. The extract is washed with water, aqueous 5% sodium hydrogen carbonate, 2% hydrochloric acid and brine, dried over sodium sulfate, and concentrated. The residue is crystallized from dichloromethane to give (Z)-2-(2-t-butoxycarbonylaminothiazol-4-yl)-2-trityloxyiminoacetic acid (144 g) as colorless crystals. Yield: 91%. mp. 157° to 158° C.

NMR δ(CDCl₃-CD₃SOCD₃) ppm: 1.50(s, 9H), 7.04(s, 1H), 7.2–7.4(m, 15H). IR ν(Nujol) cm−1: 3200, 1726, 1697, 1563, 1281, 1243, 1155.

2) (Z)-2-(2-t-butoxycarbonylaminothiazol-4-yl)-2-pentenoic acid (S1108)

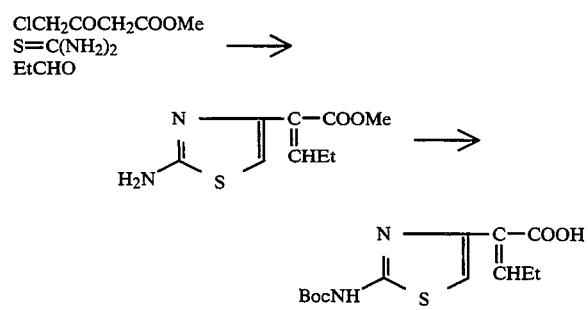

1. To a solution of 4-chloroacetoacetic acid methyl ester (700 mg: 4.65 mMol.) and propionaldehyde (405 mg: 6.97 mMol.) and acetic acid (28 mg: 0.47 mMol.) in dichloromethane (3 ml) is added a solution of piperidine (24 mg: 0.28 mMol.) in dichloromethane (0.5 ml), and the mixture is stirred at −27° C. for 120 minutes. The reaction mixture is washed with dilute hydrochloric acid and water and concentrated under reduced pressure at lower than 15° C. to give 4-chloro-2-propylideneacetoacetic acid methyl ester (818 mg). Yield: 92%.

NMR δ(CDCl₃) ppm: 1.08(t, J=7.5 Hz, 3H), 1.55(t, J=7.5 Hz, 3H), 2.2–2.8(m, 2H), 3.78(s, 3H), 3.82(s, 3H), 4.35(s, 2H), 4.40(s, 2H), 7.0–7.4(m, 1H).

2. To a solution of 4-chloro-2-propylideneacetoacetic acid methyl ester (818 mg: 4.29 mMol.) in dimethylformamide (2.1 ml) is added sodium bromide (957 mg: 9.3 mMol.), and the mixture is stirred at 22° C. for 2 hours to give a solution of 4-bromo-2-propylideneacetoacetic acid methyl ester [NMR δ(CDCl$_3$) ppm: 1.15(t, J=7.5 Hz, 3H), 2.50(q, J=7.5 Hz, 3H), 2.53(q, J=7.5 Hz, 2H), 3.82(s, 3H), 3.90(s, 3H), 4.15(s, 2H), 4.22 (s, 2H), 7.10(t, J=7.5 Hz, 1H), 7.12(t, J=7.5 Hz, 1H).]. This solution is diluted with dichloromethane (0.7 ml), mixed with a solution of thiourea (354 mg: 4.65 mMol.) in dimethylformamide (1.4 ml), and stirred at −15° C. to 30° C. for 25 minutes. The reaction mixture is washed with aqueous sodium hydroxide and brine, concentrated at less than 15° C. under reduced pressure, mixed with acetone (1.8 ml), and neutralized with 35% hydrochloric acid. The separating crystals are washed with acetone and dried over to give (Z)-2-(2-aminothiazol-4-yl)-2-pentenoic acid methyl ester hydrochloride (452 mg).

Yield: 43%. mp. 79° to 80° C. (decomposition). Elemental analysis gives values corresponding to C$_9$H$_{12}$N$_2$O$_2$S.HCl.H$_2$O.

NMR δ(CD$_3$OD) ppm: 1.14(t, J=8 Hz, 3H), 2.61(qd, J=7.6 Hz, 2H), 3.84(s, 3H), 6.71(t, J=7.6 Hz, 1H), 6.83(s, 1H). IR ν(CHCl$_3$) cm$^{-1}$: 3360, 3095, 1721, 1635, 1592, 1235.

3. A solution of (Z)-2-(2-aminothiazol-4-yl)-2-pentenoic acid methyl ester hydrochloride (550 mg: 2.2 mMol.) in dichloromethane (3 ml) is shaken with 7% aqueous sodium hydrogen carbonate (3.8 ml). The organic layer is taken and concentrated to 1.7 ml. The resulting solution is mixed with a solution of di-t-butyl dicarbonate (0.53 ml: 2.3 mMol.=1.05 equivalents) and pyridine (57 μl: 0.72 mMol.) or dimethylaminopyridine (27 mg: 0.22 mMol.) in dichloromethane (0.8 ml) and stirred at 25° C. for 6 hours. The reaction mixture is mixed with 1.6% hydrochloric acid (1.72 ml) and stirred. The organic layer is taken, washed with aqueous sodium hydrogen carbonate, dried, and concentrated under reduced pressure. The residue is purified by silica gel column chromatography to give (Z)-2-(2-t-butoxycarbonylaminothiazol-4-yl)-2-pentenoic acid methyl ester (528 mg) as oil. Yield: 71%.

NMR δ(CDCl$_3$) ppm: 1.10(t, J=7.6 Hz, 3H), 1.52(s, 9H) 2.42(qd, J=7.6 Hz, 2H), 3.85(s, 3H), 6.76(t, J=7.6 Hz, 1H), 6.89(s, 1H). IR ν(CHCl$_3$) cm$^{-1}$: 3680, 1723, 1522, 1218.

4. To a solution of (Z)-2-(2-t-butoxycarbonylaminothiazol-4-yl)-2-pentenoic acid methyl ester (425 mg: 1.4 mMol.) in isopropanol (1.3 ml) and water (3.7 ml) is added sodium hydroxide (163 mg: 4.1 mMol.), and the mixture is stirred at 65° C. for 90 minutes. The reaction mixture is adjusted to pH 4.7 with 35% hydrochloric acid and kept at 20° C. for 1 hour. The separating crystals are collected by filtration, washed with isopropanol, and dried to give (Z)-2-(2-t-butoxycarbonylaminothiazol-4-yl)-2-pentenoic acid (325 mg). Yield: 86%. mp. 187° C. (decomposition). NMR δ(CDCl$_3$) ppm: 1.09(t, J=7.6 Hz, 3H), 1.55(s, 9H) 2.64(qd, J=7.6 Hz, 2H), 6.69(t, J=7.6 Hz, 1H), 6.96(s, 1H). IR ν(CHCl$_3$) cm$^{-1}$: 3160, 2548br, 1721, 1685, 1556, 1252, 1156.

Preparation 7 other modifications at cephem ring 1) 7β-amine production : Het=1,2,3-triazol-4-yl (1P7)

To a solution of 7β-phenylacetamido-3-(1,2,3-triazol-4-yl)thiomethylthio-3-cephem-4-carboxylic acid diphenylmethyl ester (629 mg: 1 mMol.) in dichloromethane (7 ml) under ice cooling are added pyridine (162 μl: 2 mMol.) and phosphorus pentachloride (380 mg: 1.8 mMol.), and the mixture is stirred at room temperature for 40 minutes. The solution is dropwise added into a solution of 1,3-butanediol (0.46 ml) in dichloromethane (2 ml) at −30° C. After stirring under ice cooling for 30 minutes, the reaction mixture is diluted with water and extracted with dichloromethane. The extract is dried over sodium sulfate and concentrated under reduced pressure. The residue gives powder (518 mg) containing 7β-amino-3-(1,2,3-triazol-4-yl)thiomethylthio-3-cephem-4-carboxylic acid diphenylmethyl ester hydrochloride from ethyl acetate—dichloromethane. This powder (100 mg) is suspended in dichloromethane, shaken with 5% aqueous sodium hydrogen carbonate, dried over sodium sulfate, and concentrated under reduced pressure. The residue is purified by silica gel chromatography to give 7β-amino-3-(1,2,3-triazol-4-yl)thiomethylthio-3-cephem-4-carboxylic acid diphenylmethyl ester (10 mg). Yield: 10%.

NMR δ(CDCl$_3$-CD$_3$OD) ppm: 3.61, 3.73(ABq, J=17 Hz, 2H), 4.07, 4.14 (ABq, J=14 Hz, 2H), 4.74(d, J=5 Hz, 1H), 4.95(d, J=5 Hz, 1H), 6.96 (s, 1H), 7.2–7.5(m, 10H), 7.56(s, 1H). IR ν(CHCl$_3$) cm$^{-1}$: 1776, 1726.

2) 7β-amine production : Het=trityl-1,2,3-triazol-4-yl (4P9)

1) To a solution of 7β-phenylacetamido-3-(1,2,3-triazol-4-ylthiomethylthio)-3-cephem-4-carboxylic acid diphenylmethyl ester (10.0 g: 15.9 mMol.) in dichloromethane (100 ml) under ice cooling are added pyridine (1.54 ml: 19.1 mMol.) and trityl chloride (5.32 g: 19.1 mMol.), and the mixture is stirred at room temperature for 1 hour. The reaction mixture is mixed with 10% hydrochloric acid (2 ml), diluted with water, and extracted with ethyl acetate. The extract is washed with water, dried over sodium sulfate, and concentrated. To a solution of the residue in dichloromethane (50 ml) under ice cooling are added pyridine (2.57 ml: 31.8 mMol.) and phosphorus pentachloride (5.96 g: 28.6 mMol.), and the mixture is stirred for 30 minutes. The reaction mixture is added dropwise to a solution of 1.3-butanediol (8.6 ml: 95.9 mMol.) in dichloromethane (25 ml) at −30° C., and the mixture is stirred at −20° to −30° C. for 10 minutes and under ice cooling for 40 minutes. The reaction mixture is mixed with water, diluted with dichloromethane, washed with brine, dried over sodium sulfate, and concentrated. The residue is pulverized with ether, washed with ether, dissolved in dichloromethane, washed with 5% aqueous sodium hydrogen carbonate, dried over sodium sulfate, and concentrated. The residue is purified by silica gel chromatography (toluene: ethyl acetate=2:1) to give 7β-amino-3-(trityl-1,2,3-triazol-4-ylthiomethylthio)-3-cephem-4-carboxylic acid diphenylmethyl ester (6.70 g: pale yellow foam, Yield: 56%, NMR δ( CDCl$_3$) ppm: 3.62, 3.82(ABq, J=17.6 Hz, 2H), 4.05, 4.16(ABq, J=13.4 Hz, 2H), 4.66(d, J=5.0 Hz, 1H), 4.87(d, J=5.0 Hz, 1H), 6.90(s, 1H), 7.05–7.5(m, 25H), 7.45(s, 1H). IR ν(CHCl$_3$) cm$^{-1}$: 3410, 1782, 1731, 1605, 1496, 1450, 1390, 1368) and 7β-amino-3-(1,2,3-triazol-4-ylthiomethylthio)-3-cephem-4-carboxylic acid diphenylmethyl ester (2.72 g: pale yellow crystalline powder, Yield: 33%.

NMR δ(CDCl$_3$) ppm: 3.58, 3.73(ABq, J=17.5 Hz, 2H), 4.05, 4.14(ABq, J=13.7 Hz, 2H), 4.73(d, J=5.0 Hz, 1H), 4.94(d, J=5.0 Hz, 1H), 6.97(s, 1H), 7.25–7.5(m, 10H), 7.56(s, 1H). IR ν(CHCl$_3$) cm$^{-1}$: 3430, 1780, 1730, 1602, 1495, 1451, 1388, 1362. m.p. 112° to 115° C.).

3) oxidation to sulfoxide (2PB1)

To a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (30.0 g: 30.9 mMol.) in dichloromethane (300 ml) at −30° C. is added m-chloroperbenzoic acid (7.33 g: purity 80%: 1.1 equivalents: 34.0 mMol.), and the mixture is stirred at −20° to −30° C. for 20 minutes. After 20 minutes, the reaction mixture is mixed with aqueous 5% sodium thiosulfate (15 ml), diluted with dichloromethane, washed with aqueous 5% sodium hydrogen carbonate and brine, dried over sodium sulfate, and concentrated. The residue purified by silica gel column chromatography (toluene: ethyl acetate=5:1 to 3:1) to give 7β-[(Z)-2-(2-t-butoxycarbonylaminothiazol-4-yl)-2-trityloxyiminoacetylamino]-3-methanesulfonyloxy-3-cephem-4-carboxylic acid diphenyl-methyl ester 1β-oxide (28.9 g) as pale brown foam. Yield: 95%.

NMR δ(CDCl$_3$) ppm: 1.50(s, 9H), 2.74(s, 3H), 3.35, 3.89(ABq, J=18.6 Hz, 2H), 4.55(d, J=5.0 Hz, 1H) 6.31(dd, J=5.0 Hz, J=10.1 Hz, 1H), 7.00(s, 2H), 7.15–7.50(m, 25H), 7.88(d, J=10.1 Hz, 1H), 8.33(bs, 1H). IR ν(CHCl$_3$) cm$^{-1}$: 3400, 1806, 1725, 1687, 1543, 1510, 1493, 1368, 1282, 1227, 1188, 1154.

4) substitution to give thiol (2PB2)

To a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester 1β-oxide (25.0 g: 25.3 mMol.) in dimethylformamide (200 ml) at −30° C. is added sodium hydrosulfide hydrate (70%: 5.07 g: 2.5 equivalents: 63.4 mMol.), and the mixture is stirred at −20° to −30° C. for 1 hour. The reaction mixture is mixed with 10% hydrochloric acid (20 ml), diluted with water, and extracted with ethyl acetate. The extract is washed with saline, dried over sodium sulfate, and concentrated. The residue is dissolved in toluene and concentrated to dryness to give 7β-[(Z)-2-(2-t-butoxycarbonylaminothiazol-4-yl)-2-trityloxyiminoacetamide]-3-mercapto-3-cephem-4-carboxylic acid diphenylmethyl ester 1β-oxide (23.3 g: containing 8 W/W % toluene) as yellow foam. Yield: 91%.

NMR δ(CDCl$_3$) ppm: 1.49(s, 9H), 3.27, 3.67(ABq, J=18.4 Hz, 2H), 4.50 (d, J=4.8 Hz, 1H), 5.12(bs, 1H), 6.25(dd, J=4.8 Hz, J=10.0 Hz, 1H), 6.90(s, 1H), 7.01(s, 1H), 7.15–7.61 (m, 25H), 7.84(d, J=10.0 Hz, 1H), 8.41(bs, 1H). IR ν(CHCl$_3$) cm$^{-1}$: 3396, 1799, 1715, 1686, 1543, 1509, 1493, 1445, 1383, 1369, 1277, 1155.

Example 1 3-substitution with thiolacylate

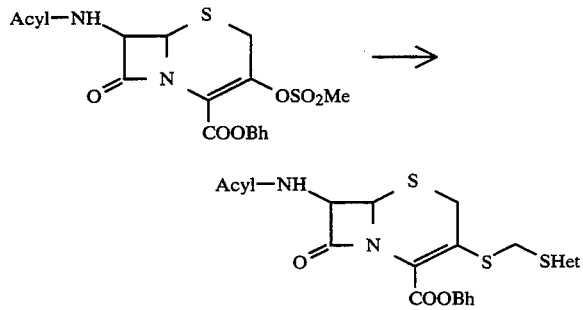

1) Acyl=phenylacetyl Het=1,2,3-triazol-4-yl (1P8)

To a solution of 4-acetylthiomethylthio-1,2,3-triazole (920 mg: 4.87 mMol.) in dimethylformamide (24 ml) at −60° C. is dropwise added a solution of sodium methoxide in methanol (1.28N: 7.5 ml). After stirring at the same temperature for 30 minutes, a solution of 7β-phenylacetamido-3-methanesulfonyloxy-3-cephem-4-carboxylic acid diphenylmethyl ester (2.32 g; 4 mMol.) in dimethylformamide (8 ml) is dropwise added. After 30 minutes, the reaction mixture is neutralized with 10% hydrochloric acid, diluted with water, and extracted with ethyl acetate. The extract is washed with water, dried over sodium sulfate, and purified by silica gel chromatography. The fraction is crystallized from ethyl acetate to give 7β-phenylacetamido-3-(1,2,3-triazol-4-yl)thiomethylthio-3-cephem-4-carboxylic acid diphenylmethyl ester (1.14 g). Yield: 45%. mp. 169° to 171° C. (decomposition).

NMR δ(CDCl$_3$-CD$_3$OD) ppm: 3.52, 362(ABq, J=17 Hz, 2H), 3.64(s, 2H), 4.07, 4.11(ABq, J=14 Hz, 2H), 4.95(d, J=5 Hz, 1H), 5.74(d, J=5 Hz, 1H), 6.92(s, 1H), 7.2–7.5(m, 15H), 7.57 (s, 1H). IR ν(KBr) cm$^{-1}$: 3400, 3300, 1784, 1700, 1650, 1520, 1375, 1220, 1770.

2) Acyl=(Z)-2-(2-t-butoxycarbonylaminothiazol-4-yl)-2-pentenoyl Het=1,2,3-triazol-4-yl (4E2-1)

To a solution of 4-acetylthiomethylthio-1,2,3-triazole (230 mg: 1.22 mMol.) in dimethylformamide (6 ml) is dropwise added a 1.26N-sodium methoxide in methanol (1.9 ml) at −60° C., and the mixture is stirred for 20 minutes, mixed with a solution of 7β-[(Z)-2-(2-t-butoxycarbonylaminothiazol-4-yl)-2-pentenoylamino]-3-methanesulfonyloxy-3-cephem-4-carboxylic acid diphenylmethyl ester (740 mg: 1 mMol.) in dimethylformamide (3 ml), and stirred at the same temperature for 40 minutes. The reaction mixture is diluted with 10% hydrochloric acid (2 ml) and water (30 ml) and extracted with ethyl acetate. The extract is washed with water, dried over sodium sulfate, and purified by silica gel chromatography (toluene: ethyl acetate=2:1) to give 7β-[(Z)-2-(2-t-butoxycarbonylaminothiazol-4-yl)-2-pentenoylamino]-3-(1,2,3-triazol-4-ylthiomethylthio)-3-cephem-4-carboxylic acid diphenylmethyl ester (553 mg) as colorless foam. Yield: 70%.

NMR δ(CDCl$_3$) ppm: 1.14(t, J=7.6 Hz, 3H), 1.54(s, 9H), 2.55–2.75(m, 2H), 2.9–3.3(broad, 2H), 3.91, 4.07(ABq, J=12 Hz, 2H), 4.98(d, J=4.4 Hz, 1H), 5.5–5.6 (broad, 1H), 6.44(t, J=7.4 Hz, 1H), 6.82(s, 1H), 6.83(s, 1H), 7.2–7.5(m, 10H), 7.62(s, 1H), 8.11(d, J=8 Hz, 1H). IR ν(CHCl$_3$) cm$^{-1}$: 3420, 3330, 3150, 1758, 1772, 1665, 1551, 1218, 1155.

3) Acyl=(Z)-2-(2-t-butoxycarbonylaminothiazol-4-yl)-2-cyclopentyloxyiminoacetyl Het=1,2,3-triazol-4-yl (4E2-3)

To a solution of 4-acetylthiomethylthio-1,2,3-triazole (374 mg: 1.98 mMol.) in dimethylformamide (9 ml) is dropwise added a 1.26N-sodium methoxide in methanol (3.1 ml), and the mixture is stirred at −60° C. for 25 minutes. To this mixture is dropwise added a solution of 7β-[(Z)-2-(2-t-butoxycarbonylaminothiazol-4-yl)-2-cyclopentyloxyiminoacetamido]-3-methanesulfonyloxy-3-cephem-4-carboxylic acid diphenylmethyl ester (1.20 g: 1.5 mMol.) in dimethylformamide (4.5 ml), and the mixture is stirred at the same temperature for 40 minutes, mixed with acetic acid (0.3 ml), diluted with water, and extracted with ethyl acetate. The extract is washed with water, 5% aqueous sodium hydrogen carbonate and water, dried over sodium sulfate, and purified by silica gel chromatography (toluene: ethyl acetate=3:1–2:1). The eluting material is crystallized from toluene and recrystallized from ethyl acetate to give 7β-[(Z)-2-(2-t-butoxycarbonylaminothiazol-4-yl)-2-cyclopentyloxy-iminoacetamido]-3-(1,2,3-triazol-4- ylthiomethylthio)-3-cephem-4-carboxylic acid diphenylmethyl ester (274 mg). Yield: 22%. mp. 198° C. (decomposition).

NMR δ(CDCl₃-CD₃OD) ppm: 1.55(s, 9H), 1.3–2.0(m, 8H), 3.56, 3.72(ABq, J=17 Hz, 2H), 4.15(s, 2H), 4.9–5.0(m, 1H), 5.06(d, J=4.8 Hz, 1H), 5.86(d, J=4.8 Hz, 1H), 6.97(s, 1H), 7.3–7.5(m, 11H), 7.60(s, 1H). IR ν(KBr) cm⁻¹: 3330, 3200, 1785, 1725, 1698, 1660, 1570, 1525, 1370, 1241, 1220, 1160.

4) Acyl=(Z)-2-(2-t-butoxycarbonylaminothiazol-4-yl)-2-(2-propenyloxyimino)acetyl Het=1,2,3-triazol-4-yl (4E2-2)

To a solution of 4-acetylthiomethylthio-1,2,3-triazole (230 mg: 1.22 mMol.) in dimethylformamide (6 ml) is dropwise added a 1.26N-sodium methoxide in methanol (1.9 ml) at −60° C., and the mixture is stirred at the same temperature for 25 minutes, and cooled to −78° C. To the reaction mixture is dropwise added a solution of 7β-[(Z)-2-(2-t-butoxycarbonylaminothiazol-4-yl)-2-(2-propenyloxyimino)acetamido]-3-methanesulfonyloxy-3-cephem-4-carboxylic acid diphenylmethyl ester (770 mg: 1 mMol.) in dimethylformamide (3 ml), and the mixture is stirred at the same temperature for 40 minutes. The reaction mixture is diluted with 1N-hydrochloric acid (2 ml) and water (50 ml), and extracted with ethyl acetate. The extract is washed with water, dried over sodium sulfate, and purified by silica gel chromatography (toluene: ethyl acetate=2:1). The eluted material is crystallized from toluene to give 7β-[(Z)-2-(2-t-butoxycarbonylaminothiazol-4-yl)-2-(2-propentyloxyimino)acetamido]-3-(1,2,3-triazol-4-ylthiomethylthio)-3-cephem-4-carboxylic acid diphenylmethyl ester (415 mg) as colorless crystals. Yield: 51%. mp. 167° to 170° C. (decomposition).

NMR δ(CDCl₃-CD₃OD) ppm: 1.55(s, 9H), 3.54, 3.69(ABq, J=17 Hz, 2H), 4.16 (s, 2H), 4.82(d, J=5.8 Hz, 2H), 5.07(d, J=4.6 Hz, 1H), 5.26(dd, J=1.4 Hz, J=10.6 Hz, 1H), 5.37(dd, J=1.4 Hz, J=17.4 Hz, 1H), 5.86(d, J=4.6 Hz, 1H), 6.04(ddt, J=5.8 Hz, J=10.6 Hz, J=17.4 Hz, 1H), 6.97(s, 1H), 7.3–7.5(m, 11H), 7.60(s, 1H). IR ν(CHCl₃) cm⁻¹: 3400, 3300, 3200, 1782, 1717, 1696, 1658, 1534, 1370, 1281, 1240, 1221, 1154.

5) Acyl=(Z)-2-(2-t-butoxycarbonylaminothiazol-4-yl)-2-trityloxyiminoacetyl Het=1,2,3-triazol-4-yl (1E02)

To a solution of 4-acetylthiomethylthio-1,2,3-triazole (11.50 g: 61 mMol.) in dimethylformamide (300 ml) is added dropwise a solution of sodium methoxide (1.28N: 94 ml) in methanol at −60° to −50° C. After stirring for 20 minutes, a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (48.55 g: 50 mMol.) in dimethylformamide (190 ml) is added dropwise to the mixture over 7 minutes at the same temperature. After 50 minutes, the reaction mixture is diluted with acetic acid (10 ml) and water (2 liters) and extracted with ethyl acetate. The extract is washed with brine, dried over sodium sulfate, and concentrated under reduced pressure. The residue is crystallized from toluene and recrystallized from ethyl acetate-toluene mixture to give 7β-[(Z)-2-(2-t-butoxycarbonylamino-4-thiazolyl)-2-trityloxyiminoacetamido]-3-(1,2,3-triazol-4-yl)thiomethylthio-3-cephem-4-carboxylic acid diphenylmethyl ester as colorless crystals (29.14 g). Yield: 57%. 190°–200° C. (decomp.).

NMR δ(CDCl₃-CD₃OD) ppm: 1.53(s, 9H), 3.45, 3.63(ABq, J=17.2 Hz, 2H), 4.12, 4.15 (ABq, J=14.2 Hz, 2H), 5.08(d, J=5 Hz, 1H), 5.88(d, J=5 Hz, 1H), 6.98(s, 1H), 7.08(s, 1H), 7.2–7.5(m, 25H), 7.60(s, 1H). IR ν(KBr) cm⁻¹: 3390, 3210, 1800, 1725, 1688, 1555, 1495, 1449, 1375, 1275, 1245, 1225, 1155.

6) Acyl=(Z)-2-(2-t-butoxycarbonylaminothiazol-4-yl)-2-trityloxyiminoacetyl Het=1,2,3-triazol-4-yl (with thiolbenzoate) (4E2-4)

To a solution of 4-benzoylthiomethylthio-1,2,3-triazole (150 mg: 0.60 mMol.) in dimethylformamide (3 ml) at −60° C. is added a solution of sodium methoxide in methanol (1.26N: 0.95 ml), and the mixture is stirred for 80 minutes at −50° to −60° C. To the mixture at −70° C. is added a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (485 mg: 0.5 mMol.) in dimethylformamide (2 ml) and the mixture is stirred at −70° C. for 20 minutes. The reaction mixture is mixed with acetic acid (0.1 ml), diluted with water, and extracted with ethyl acetate. The extract is washed with brine, dried over sodium sulfate, and concentrated. The residue is crystallized from toluene to give 7β-[(Z)-2-(2-t-butoxycarbonylaminothiazol-4-yl)-2-trityloxyiminoacetamido]-3-(1,2,3-triazol-4-ylthiomethylthio)-3-cephem-4-carboxylic acid diphenylmethyl ester (227 mg) as colorless crystals. Yield: 44%.

NMR δ(CDCl₃-CD₃OD) ppm: 1.53(s, 9H), 3.45, 3.63(ABq, J=17.2 Hz, 2H), 4.12, 4.15 (ABq, J=14.2 Hz, 2H), 5.08(d, J=5 Hz, 1H), 5.88(d, J=5 Hz, 1H), 6.98(s, 1H), 7.08(s, 1H), 7.2–7.5(m, 25H), 7.60(s, 1H). IR ν(KBr) cm⁻¹: 3390, 3210, 1800, 1725, 1688, 1555, 1495, 1449, 1375, 1275, 1245, 1225, 1155.

7) Acyl=(Z)-2-(2-t-butoxycarbonylaminothiazol-4-yl)-2-trityloxyiminoacetyl Het=1-trityl-1,2,3-triazol-4-yl (1E3)

To a solution of 4-acetylthiomethylthio-1-trityl-1,2,3-triazole (25.0 g: 58 mMol. ) in a mixture of dimethylformamide (300 ml) and tetrahydrofuran (100 ml) at −78° C. is added dropwise a solution of sodium methoxide in methanol (1.35N: 37.8 ml: 51 mMol.). After stirring for 15 minutes, a solution 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (45.0 g: 46.3 mMol.) in a mixture of dimethylformamide (120 ml) and tetrahydrofuran (45 ml) is added to the mixture at −78° C. over 5 minutes. After stirring for 1 hour at −78° C., the reaction mixture is diluted with 10% hydrochloric acid (19 ml) and water (1.5 L) and extracted with ethyl acetate. The extract is washed with brine, dried over sodium sulfate, and concentrated under reduced pressure. The residue is purified by silica gel chromatography (toluene: ethyl acetate=15 to 10:1) and triturated in hexane-ether to give 7β-[(Z)-2-(2-t-butoxycarbonylaminothiazol-4-yl)-2-trityloxy-iminoacetamido]-3-(1-trityl-1,2,3-triazol-4-yl)-thiomethylthio-3-cephem-4-carboxylic acid diphenylmethyl ester as white powder (49.1 g). Yield: 84%.

NMR δ(CDCl₃) ppm: 1.50(s, 9H), 3.31, 3.56 (ABq, J=17 Hz, 2H), 4.05 (s, 2H), 4.97(d, J=4.8 Hz, 1H), 5.84(dd, J=4.8 Hz, J=8.7 Hz, 1H), 6.86(s, 1H), 7.02(s, 1H), 7.05–7.4(m, 41H), 7.45(s, 1H), 8.4–8.7(brs, 1H). IR ν(CHCl₃) cm⁻¹: 3400, 1783, 1718, 1685, 1541, 1490, 1443, 1368, 1154.

8) Acyl=(Z)-2-(2-t-butoxycarbonylaminothiazol-4-yl)-2-methoxyiminoacetyl Het=1-trityl-1,2,3-triazol-4-yl (3E1-2-2)

To a solution of 4-acetylthiomethylthio-1-trityl-1,2,3-triazole (414 mg: 0.96 mMol.) in a mixture of dimethylformamide (5 ml) and tetrahydrofuran (2.5 ml) is added 1.28N-sodium methoxide (0.69 ml: 0.88 mMol.) at −78° C., and the mixture is stirred for 12 minutes. To this mixture is added dropwise a solution of 7β-[(Z)-2-(2-t-butoxycarbonylaminothiazol-4-yl)-2-methoxyiminoacetyl]amino-3-methanesulfonyloxy-3-cephem-4-carboxylic acid diphenylmethyl ester (594 mg: 0.8 mMol.) in dimethylformamide (2.5 ml) over 2 minutes and the mixture is stirred at the same temperature for 1 hour. To the mixture is added 10% hydrochloric acid (1 ml) to quench the reaction and extracted with ethyl acetate. The extract is washed with water, dried over sodium sulfate and concentrated. The residue is purified by silica gel chromatography (toluene: ethyl acetate=2:1) to give 7β-[(Z)-2-(2-t-butoxycarbonylaminothiazol-4-yl)-2-methoxyiminoacetyl]amino-3-(1-trityl-1,2,3-triazol-4-yl)thiomethylthio-3-cephem-4-carboxylic acid diphenylmethyl ester as white foam (579 mg). Yield: 70%.

NMR δ(CDCl₃) ppm: 1.52(s, 9H), 3.65, 3.81(ABq, J=18 Hz, 2H), 4.10, 4.19(ABq, J=12 Hz, 2H), 5.02(d, J=4.8 Hz, 1H), 5.90(dd, J=4.8 Hz, J=8.8 Hz, 1H), 6.87(s, 1H), 7.0–7.5(m, 27H), 8.8(brs, 1H). IR ν(CHCl₃) cm⁻¹: 3400, 1780, 1720, 1680, 1540, 1370.

9) Acyl=(Z)-2-(2-t-butoxycarbonylaminothiazol-4-yl)-2-trityloxyiminoacetyl Het=1-methyl-1,2,3-triazol-4-yl (1E4-1)

To a solution of 4-acetylthiomethylthio-1-methyl-1,2,3-triazole (392 mg: 1.93 mMol.) in a mixture of dimethylformamide (6 ml) and tetrahydrofuran (2 ml) at −78° C. is added dropwise a solution of 1.28N sodium methoxide (1.33 ml: 1.70 mMol.) in methanol. After stirring for 15 minutes, a solution of 7β-[(Z)-2-(2-t-butoxycarbonyl-aminothiazol-4-yl)-2-trityloxyiminoacetamido]-3-methanesulfonyloxy-3-cephem-4-carboxylic acid diphenylmethyl ester (1.50 g: 1.54 mMol.) in dimethylformamide (5 ml) is added to the mixture. After stirring for 1 hour at the same temperature, the reaction mixture is neutralized with 10% hydrochloric acid, diluted with water, and extracted with ethyl acetate. The extract is washed with brine, dried over sodium sulfate, and concentrated under reduced pressure. The residue is purified by silica gel chromatography (toluene: ethyl acetate=3:2) to give 7β-[(Z)-2-(2-t-butoxycarbonylaminothiazol-4-yl)-2-trityloxyimino-acetamido]-3-(1-methyl-1,2,3-triazol-4-yl)thiomethylthio-3-cephem-4-carboxylic acid diphenylmethyl ester (1.43 g). Yield: 90%. Colorless foam.

NMR δ(CDCl₃) ppm: 1.49(s, 9H), 3.35, 3.51(ABq, J=16.8 Hz, 2H), 3.92 (s, 3H), 4.08(s, 2H), 5.06(d, J=4.7 Hz, 1H), 5.91(dd, J=8.6 Hz, J=4.7 Hz, 1H), 6.93 (s, 1H), 6.99(s, 1H), 7.15–7.50(m, 26H), 7.66(d, J=8.6 Hz, 1H), 8.83(brs, 1H). IR ν(CHCl₃) cm⁻¹: 3390, 1781, 1714, 1684, 1540, 1490, 1443, 1366, 1281, 1218, 1153, 970.

10) Acyl=(Z)-2-(2-t-butoxycarbonylaminothiazol-4-yl)-2-trityloxyiminoacetyl Het=2-methyl-1,2,3-triazol-4-yl (1E4-2)

To a solution of 4-acetylthiomethylthio-2-methyl-1,2,3-triazole (392 mg: 1.93 mMol.) in a mixture dimethylformamide (8 ml) and tetrahydrofuran (4 ml) is added dropwise a solution of 1.28N sodium methoxide (1.33 ml: 1.70 mMol.) in methanol at −78° C., and the mixture is stirred for 15 minutes. To the mixture is added a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (1.50 g: 1.54 mMol.) in dimethylformamide (5 ml). After stirring for 1 hour at the same temperature, the reaction mixture is neutralized with 10% hydrochloric acid, diluted with water, and extracted with ethyl acetate. The extract is washed with brine, dried over sodium sulfate, and concentrated under reduced pressure. The residue is purified by silica gel chromatography (n-hexane: ethyl acetate=1:1) to give 7β-[(Z)-2-(2-t-butoxycarbonylaminothiazol-4-yl)-2-trityloxyiminoacetylamino]-3-(2-methyl-1,2,3-triazol-4-yl)thiomethylthio-3-cephem-4-carboxylic acid diphenylmethyl ester (1.45 g) as colorless foam. Yield: 91%.

NMR δ(CDCl₃) ppm: 1.50(s, 9H), 3.32, 3.43(ABq, J=16.8 Hz, 2H), 3.98 (s, 2H), 4.10(s, 3H), 5.07(d, J=4.9 Hz, 1H), 5.86(dd, J=8.3 Hz, J=4.9 Hz, 1H), 6.90(s, 1H), 6.99(s, 1H), 7.15–7.45(m, 25H), 7.49(s, 1H), 7.61(d, J=8.3 Hz, 1H), 8.85(brs, 1H). IR ν(CHCl₃) cm⁻¹: 3402, 1785, 1717, 1686, 1543, 1493, 1445, 1369, 1280, 1155, 1115, 1079, 972, 910.

11) Acyl=(Z)-2-(2-t-butoxycarbonylaminothiazol-4-yl)-2-trityloxyiminoacetyl Het=1-trityl-1,2,4-triazol-3-yl (1E5)

To a solution of 3-acetylthiomethylthio-1-trityl-1,2,4-triazole (1.17 g: 2.71 mMol.) in a mixture of dimethylformamide (10 ml) and tetrahydrofuran (5 ml) is added dropwise a solution of sodium methoxide in methanol (1.28N: 2.0 ml: 2.56 mMol.) at −78° C., and the mixture is stirred for 15 minutes. To this mixture is added dropwise a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (2.40 g: 2.47 mMol.) in dimethylformamide (5 ml). After stirring for 50 minutes at the same temperature, the reaction was quenched with 10% hydrochloric acid (0.95 ml), diluted with water, and extracted with ethyl acetate. The extract is washed with brine, dried over sodium sulfate, and concentrated under reduced pressure. The residue is purified by silica gel chromatography (toluene: ethyl acetate=3:1) to give 7β-[(Z)-2-(2-t-butoxycarbonylaminothiazol-4-yl)-2-trityloxyiminoacetamido]-3-(1-trityl-1,2,4-triazol-3-yl)thiomethylthio-3-cephem-4-carboxylic acid diphenylmethyl ester as colorless foam (1.93 g).

NMR δ(CDCl₃) ppm: 1.50(s, 9H), 3.30, 3.41 (ABq, J=17.4 Hz, 2H), 4.17 (s, 2H), 4.95(d, J=4.9 Hz, 1H), 5.90(dd, J=4.9 Hz, J=8.5 Hz, 1H), 6.94(s, 1H), 7.02(s, 1H), 7.05–7.55(m, 41H), 7.89(s, 1H), 8.4–8.6(brs, 1H). IR ν(CHCl₃) cm⁻¹: 3398, 1781, 1715, 1683, 1540, 1490, 1442, 1367, 1270, 1154.

12) Acyl=(Z)-2-(2-t-butoxycarbonylaminothiazol-4-yl)-2-trityloxyiminoacetyl Het=5-tetrazolyl (3E1-2-1)

To a solution of 5-acetylthiomethylthiotetrazole (478 mg: 2.52 mMol.) in dimethylformamide (30 ml) cooling at −70° C. is dropwise added a solution of 1.26N sodium methoxide in methanol (3.9 ml), and the mixture is stirred at −60° to −65° C. for 25 minutes. To the reaction mixture cooling at −70° C. is dropwise added a solution of 7β-[(Z)-2-(2-t-butoxycarbonylaminothiazol-4-yl)-2-trityloxyiminoacetyl]amino-3-methanesulfonyloxy-3-cephem-4-carboxylic acid diphenylmethyl ester (2.00 g: 2.06 mMol.) in dimethylformamide (7 ml), and the mixture is stirred at −65° to −70° C. for 40 minutes. The reaction mixture is mixed with 10% hydrochloric acid (0.5 ml), diluted with water, and extracted with ethyl acetate. The extract is washed with brine, dried over sodium sulfate, filtered, and concentrated. The residue is purified by silica gel column chromatography (toluene: ethyl acetate=1:1-ethyl acetate-ethyl acetate containing 0.5% acetic acid) to give 7β-

[(Z)-2-(2-t-butoxycarbonylaminothiazol-4-yl)-2-trityloxyiminoacetyl]amino-3-(tetrazol-5-yl)thiomethylthio-3-cephem-4-carboxylic acid diphenylmethyl ester as pale yellow foam (968 mg) containing unidentified byproduct (ca. 10%).

NMR δ(CDCl₃-CD₃OD) ppm: 1.52(s, 9H), 3.58, 3.71(ABq, J=17.6 Hz, 2H), 4.46(s, 2H), 5.10(d, J=4.8 Hz, 1H), 5.99(d, J=4.8 Hz, 1H), 6.95(s, 1H), 7.06(s, 1H), 7.15–7.50(m, 25H). IR ν(CHCl₃) cm⁻¹: 3402, 3200br, 1786, 1717, 1672, 1544, 1492, 1446, 1369, 1280, 1154.

13) Acyl=2-(2-t-butoxycarbonylaminothiazol-4-yl)-2-trityloxyiminoacetyl Het=2-pyridyl (2E1-3)

To a solution of 2-acetylthiomethylthiopyridine (249 mg: 1.25 mMol.) in a mixture of dimethylformamide (4 ml) and tetrahydrofuran (2 ml) cooling at −78° C. is added dropwise 1.26N-sodium methoxide-methanol solution (0.87 ml: 1.10 mMol.), and the mixture is stirred at −78° C. for 15 minutes. To this reaction mixture is added a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (971 mg: 1.00 mMol.) in dimethylformamide (2 ml) and the mixture is stirred at −78° C. for 1 hour. The reaction mixture is mixed with 10% hydrochloric acid to stop the reaction, diluted with water, and extracted with ethyl acetate. The extract is washed with dilute aqueous sodium hydrogen carbonate and brine, dried over sodium sulfate, and concentrated. The residue is purified by silica gel chromatography (toluene: ethyl acetate=4:1) and silica gel rechromatography (toluene: ethyl acetate=7:1) to give 7β-[(Z)-2-(2-t-butoxycarbonylaminothiazol-4-yl)-2-trityloxyiminoacetamido]-3-(pyrid-2-ylthiomethylthio)-3-cephem-4-carboxylic acid diphenylmethyl ester as colorless foam (753 mg). Yield: 73%.

NMR δ(CDCl₃) ppm: 1.51(s, 9H), 3.42, 3.56(ABq, J=17.2 Hz, 2H), 4.45 (s, 2H), 5.04 (d, J=4.9 Hz, 1H), 5.87(dd, J=4.9 Hz, J=8.6 Hz, 1H), 6.90(s, 1H), 7.01(ddd, J=7.4 Hz, J=4.9 Hz, J=1.0 Hz, 1H), 7.03(s, 1H), 7.11–7.53 (m, 28H), 8.41(ddd, J=4.9 Hz, J=1.8 Hz, J=1.0 Hz, 1H), 8.55(brs, 1H). IR ν(CHCl₃) cm⁻¹: 3402, 1784, 1717, 1686, 1574, 1543, 1514, 1493, 1450, 1369, 1282, 1154.

Example 2 3-substitution with iodide

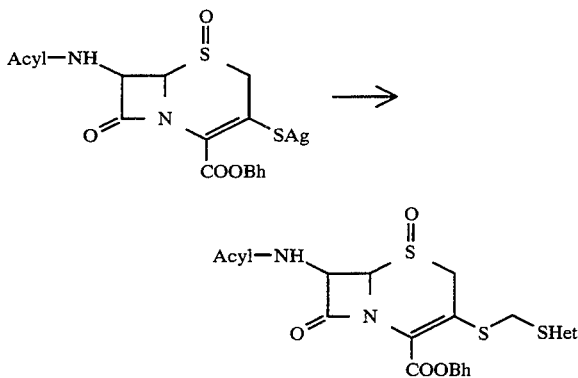

1) Acyl=(Z)-2-(2-t-butoxycarbonylaminothiazol-4-yl)-2-trityloxyiminoacetyl Het=trityl-1,2,4-triazol-3-yl (4E3-4)

To a suspension of trityl-3-chloromethylthio-1,2,4-triazole (11.75 g: 30.0 mMol.) in acetone (150 ml) is added sodium iodide (9.00 g: 60.0 mMol.), and the mixture is stirred at 50° C. for 3 hours. The reaction mixture is diluted with water and extracted with ethyl acetate. The extract is washed with brine, dried over sodium sulfate, and concentrated to give trityl-3-iodomethylthio-1,2,4-triazole as yellow crystals [NMR δ(CDCl3) ppm: 4.70(s, 2H), 7.1 to 7.2(m, 6H), 7.3 to 7.4(m, 9H), 7.96(s, 1H): 13 g]. To a solution of 7β-[(Z)-2-(2-t-butoxycarbonylaminothiazol-4-yl)-2-trityloxyiminoacetylamino]-3-argentiothio-3-cephem-4-carboxylic acid diphenylmethyl ester 1-oxide (16.8 g: 15 mMol.) in hexamethylphosphoramide (90 ml) is added trityl-3-iodomethylthio-1,2,4-triazole (13 g), and the mixture is stirred at room temperature for 3 hours. The reaction mixture is diluted with ethyl acetate, mixed with saturated brine, and filtered through Celite. The organic layer is taken, washed with brine, dried over sodium sulfate, and concentrated. The residue is purified by silica gel chromatography (toluene: ethyl acetate=5:1–3:1) to give 7β-[(Z)-2-(2-t-butoxycarbonylaminothiazol-4-yl)-2-trityloxyiminoacetylamino]-3-(trityl-1,2,4-triazol-3-ylthiomethylthio)-3-cephem-4-carboxylic acid diphenylmethyl ester 1-oxide (11.29 g) as pale brown foam. Yield: 59%.

NMR δ(CDCl₃) ppm: 1.49(s, 9H), 3.19, 3.82(ABq, J=18.5 Hz, 2H), 4.19(d, J=4.6 Hz, 1H), 4.16, 4.22(ABq, J=13.7 Hz, 2H), 6.19(dd, J=4.6 Hz, J=10.1 Hz, 1H), 6.97(s, 1H), 7.05–7.5(m, 41H), 7.90(s, 1H), 8.04(d, J=10.1 Hz, 1H), 8.30(brs, 1H). IR ν(CHCl₃) cm⁻¹: 3400, 1804, 1725, 1689, 1543, 1496, 1449, 1371, 1040.

2) Acyl=(Z)-2-(2-t-butoxycarbonylaminothiazol-4-yl)-2-trityloxyiminoacetyl Het=1-methyl-1,2,4-triazol-3-yl (4E3-2)

To a solution of 7β-[(Z)-2-(2-t-butoxycarbonylaminothiazol-4-yl)-2-trityloxyiminoacetylamino]-3-argentiothio-3-cephem-4-carboxylic acid diphenylmethyl ester 1-oxide (3.37 g: 3 mMol.) in hexamethylphosphoramide (20 ml) is added 3-iodomethylthio-1-methyl-1,2,4-triazole (1.50 g), and the mixture is stirred at room temperature for 3 hours. The reaction mixture is diluted with saturated brine and ethyl acetate and filtered to remove insoluble material. The organic layer is taken, washed with brine, dried over sodium sulfate, and concentrated. The residue is purified by silica gel chromatography (toluene: ethyl acetate=1:1) to give 7β-[(Z)-2-(2-t-butoxycarbonylaminothiazol-4-yl)-2-trityloxyiminoacetylamino]-3-(1-methyl-1,2,4-triazol-3-ylthio-methylthio)-3-cephem-4-carboxylic acid diphenylmethyl ester 1-oxide (1.82 g) as yellow brown foam. Yield: 58%.

NMR δ(CDCl₃) ppm: 1.46(s, 9H), 3.76(s, 3H), 3.49, 4.12(ABq, J=18.4 Hz, 2H), 4.28(s, 2H), 4.46(d, J=4.8 Hz, 1H), 6.24(dd, J=4.8 Hz, J=9.8 Hz, 1H), 6.93(s, 1H), 6.98(s, 1H), 7.2–7.55(m, 25H), 7.91(s, 1H), 8.02(d, J=9.8 Hz, 1H), 8.66(brs, 1H). IR ν(CHCl₃) cm⁻¹: 3410, 1803, 1724, 1689, 1545, 1510, 1497, 1450, 1372, 1042.

3) Acyl=(Z)-2-(2-t-butoxycarbonylaminothiazol-4-yl)-2-trityloxyiminoacetyl Het=2-methyl-1,2,4-triazol-3-yl (4E3-1)

To a solution of 7β-[(Z)-2-(2-t-butoxycarbonylaminothiazol-4-yl)-2-trityloxyiminoacetylamino]-3-argentiothio3-cephem-4-carboxylic acid diphenylmethyl ester 1-oxide (3.37 g: 3 mMol.) in hexamethylphosphoramide (20 ml) is added a solution of 3-iodomethylthio-2-methyl-1,2,4-triazole (1.47 g) in hexamethylphosphoramide (3 ml), and the mixture is stirred at room temperature for 3 hours. The reaction mixture is diluted with saturated brine and ethyl acetate and filtered to remove insoluble material. The organic layer is taken, washed with brine, dried over sodium sulfate, and concentrated. The residue is purified by silica gel chromatography (toluene: ethyl acetate=1:1) to give 7β-[(Z)-2-(2-t-butoxycarbonylaminothiazol-4-yl)-2-trityloxyiminoacetylamino]-3-(2-methyl-1,2,4-triazol-3-ylthiomethylthio)-3-cephem-4-carboxylic acid diphenylmethyl ester 1-oxide (1.76 g) as brown foam. Yield: 56%.

NMR δ(CDCl$_3$) ppm: 1.47(s, 9H), 3.66(s, 3H), 3.47, 3.97(ABq, J=18.8 Hz, 2H), 4.38(d, J=4.8 Hz, 1H), 4.22, 4.48(ABq, J=13.7 Hz, 2H), 6.25(dd, J=4.8 Hz, J=10.0 Hz, 1H), 6.96(s, 1H), 6.97(s, 1H), 7.2–7.5(m, 25H), 7.79(s, 1H), 8.02(d, J=10.0 Hz, 1H), 8.59(brs, 1H). IR ν(CHCl$_3$) cm$^{-1}$: 3400, 1805, 1722, 1688, 1542, 1509, 1496, 1449, 1371, 1041.

4) Acyl=(Z)-2-(2-t-butoxycarbonylaminothiazol-4-yl)-2-trityloxyiminoacetyl Het=1,2,3-thiadiazol-5-yl (3E1-1-1)

To a solution of 7β-[(Z)-2-(2-t-butoxycarbonylaminothiazol-4-yl)-2-trityloxyiminoacetyl]amino-3-mercapto-3-cephem-4-carboxylic acid diphenylmethyl ester 1β-oxide (purity 92%: 3.0 g: 3.0 mMol.) in tetrahydrofuran (20 ml) is added a solution of silver nitrate (560 mg: 3.3 mMol.) in water (3 ml), and the mixture is stirred under ice cooling for 20 minutes. The reaction mixture is diluted with water and extracted with dichloromethane. The extract is washed once with water, dried over sodium sulfate, filtered, and concentrated to give 7β-[(Z)-2-(2-t-butoxycarbonylaminothiazol-4-yl)-2-trityloxyiminoacetyl]amino-3-argentiothio-3-cephem-4-carboxylic acid diphenyl methyl ester 1β-oxide (3.37 g) as yellow brown foam.

To a solution of this silver salt in hexamethylphosphoramide (20 ml) is added a solution of 5-iodomethylthio-1,2,3-thiadiazole (1.55 g) in hexamethylphosphoramide (3 ml), and the mixture is stirred at room temperature for 3 hours. The reaction mixture is mixed with brine and extracted with ethyl acetate. After filtering off the insoluble material, the extract is washed with water, dried over sodium sulfate, filtered, and concentrated. The residue is purified by silica gel column chromatography (toluene: ethyl acetate=3:1–2:1) to give 7β-[(Z)-2-(2-t-butoxycarbonylaminothiazol-4-yl)-2-trityloxyiminoacetyl]amino-3-(1,2,3-thiadiazol-5-yl)thiomethylthio-3-cephem-4-carboxylic acid diphenylmethyl ester 1β-oxide (1.49 g) as off-white powder. Yield: 47%.

NMR δ(CDCl$_3$) ppm: 1.48(s, 9H), 3.23, 3.91(ABq, J=17.6 Hz, 2H), 3.91, 4.09(ABq, J=14.1 Hz, 2H), 4.49(d, J=4.8 Hz, 1H), 6.31 (dd, J=4.8 Hz, J=10.0 Hz, 1H), 6.98(s, 1H), 7.00(s, 1H), 7.15–7.5(m, 25H), 7.96(d, J=10.0 Hz, 1H), 8.45(brs, 1H), 8.47(s, 1H). IR ν(CHCl$_3$) cm$^{-1}$: 3400, 1804, 1718, 1690, 1543, 1510, 1493, 1446, 1369, 1226, 1154, 1031.

5) Acyl=(Z)-2-(2-t-butoxycarbonylaminothiazol-4-yl)-2-trityloxyiminoacetyl Het=1,3,4-thiadiazol-2-yl (2E1-1)

1. To a solution of 7β-[(Z)-2-(2-t-butoxycarbonylaminothiazol-4-yl)-2-trityloxyiminoacetamido]-3-mercapto-3-cephem-4-carboxylic acid diphenylmethyl ester 1-oxide (2.78 g: 3 mMol. ) in tetrahydrofuran (20 ml) is added a solution of silver nitrate (560 mg: 1.1 equivalents: 3.3 mMol.) in water (3 ml) under ice cooling. After 10 minutes, the reaction mixture is diluted with water and extracted with dichloro- methane. The extract is washed with water, dried over sodium sulfate, and concentrated to give residue (3.4 g) as brown foam. To a suspension of this silver salt in hexamethylphosphoramide (20 ml) is added 2-iodomethylthio-1,3,4-thiadiazole (1.2 g) at room temperature and the mixture is stirred for 17 hours. The reaction mixture is diluted with brine and extracted with ethyl acetate. The extract is filtered to remove solid, washed with brine, dried over sodium sulfate, and concentrated. The residue is purified by silica gel chromatography (toluene: ethyl acetate=3:1 to 2:1) to give 7β-[(Z)-2-(2-t-butoxycarbonylaminothiazol-4-yl)-2-trityloxyiminoacetamido]-3-(1,3,4-thiadiazol-2-ylthiomethylthio)-3-cephem-4-carboxylic acid diphenylmethyl ester 1β-oxide (776 mg) as pale brown foam. Yield: 25%.

NMR δ(CDCl$_3$) ppm: 1.49(s, 9H), 3.74, 3.98(ABq, J=18 Hz, 2H), 4.29, 4.84(ABq, J=14 Hz, 2H), 4.55(d, J=4.8 Hz, 1H), 6.27(dd, J=4.8 Hz, J=10 Hz, 1H), 6.98(s, 1H), 7.00(s, 1H), 7.2–7.5(m, 25H), 7.86(d, J=10 Hz, 1H), 8.45(brs, 1H), 9.00(s, 1H). IR ν(CHCl$_3$) cm$^{-1}$: 3400, 1802, 1718, 1688, 1544, 1369, 1154.

2. A solution of 7β-[(Z)-2-(2-t-butoxycarbonylaminothiazol-4-yl)-2-trityloxyiminoacetamido]-3-mercapto-3-cephem-4-carboxylic acid diphenylmethyl ester 1β-oxide silver salt (0.2 g) in hexamethylphosphoramide (2 ml) is divided into two portions, and 2-chloromethylthio-1,3,4-thiadiazole (0.05 g) is added to one and 2-bromomethylthio-1,3,4-thiadiazole (0.05 g) is added to the other. After standing at room temperature for 10 hours, thin layer chromatogram (toluene: ethyl acetate=2:1) of each portions gives the spot of Rf value the same with the product described in paragraph 1. above.(Rf=0.2).

3. 7β-[(Z)-2-(2-t-butoxycarbonylaminothiazol-4-yl)-2-trityloxyiminoacetamido]-3-mercapto-3-cephem-4-carboxylic acid diphenylmethyl ester 1β-oxide (1.85 g: 2 mMol.) is added to a solution of 2-iodomethylthio-1,3,4-thiadiazole (675 mg: 2.6 mMol.) in dimethylformamide (10 ml) at −50° C. To the mixture is added dropwise pyridine (0.21 ml: 2.6 mMol.), and the mixture is stirred at −50° C. for 1 hour. The reaction mixture is mixed with 1N-hydrochloric acid (3 ml), diluted with water, and extracted with ethyl acetate. The extract is washed with water, dried over sodium sulfate, and concentrated. The residue is purified by silica gel chromatography (toluene: ethyl acetate=3:1 to 2:1) to give 7β-[(Z)-2-(2-t-butoxycarbonylaminothiazol-4-yl)-2-trityloxyiminoacetamido]-3-(1,3,4-thiadiazol-2-ylthiomethylthio)-3-cephem-4-carboxylic acid diphenylmethyl ester 1β-oxide as pale brown foam (305 mg). Yield: 15%.

6) Acyl=(Z)-2-(2-t-butoxycarbonylaminothiazol-4-yl)-2-trityloxyiminoacetyl Het=2-methyl-1,3,4-thiadiazol-5-yl (2E1-2)

To a solution of 7β-[(Z)-2-(2-t-butoxycarbonylaminothiazol-4-yl)-2-trityloxyiminoacetamido]-3-mercapto-3-cephem-4-carboxylic acid diphenylmethyl ester 1β-oxide (1.85 g: 2 mMol.) in tetrahydrofuran (12 ml) is added a solution of silver nitrate (373 mg: 1.1 equivalents: 2.2 mMol.) in water (2 ml) under ice cooling, and the mixture is stirred for 10 minutes. The reaction mixture is diluted with water and extracted with dichloromethane. The extract is washed with water, dried over sodium sulfate, and concentrated to give the silver salt as brown foam (2.1 g). To a suspension of this salt in hexamethylphosphorotriamide (10 ml) is added 5-iodomethylthio-2-methyl-1,3,4-thiadiazole (1.05 g), and the mixture is stirred at room temperature for 4 hours. The reaction mixture is diluted with brine and extracted with ethyl acetate. The extract is filtered to remove solid, washed with brine, dried over sodium sulfate, and concentrated. The residue is purified by silica gel chromatography (toluene: ethyl acetate=3:1 to 2:1), to give 7β-[(Z)-2-(2-t-butoxycarbonylaminothiazol-4-yl)-2-trityloxyiminoacetamido]-3-(2-methyl-1,3,4-thiadiazol-5-ylthiomethylthio)-3-cephem-4-carboxylic acid diphenylmethyl ester 1β-oxide as pale yellow foam (382 mg). Yield: 18%.

NMR δ(CDCl3) ppm: 1.49(s, 9H), 2.68(s, 3H), 3.76, 3.97(ABq, J=19 Hz, 2H), 4.23, 4.75 (ABq, J=14 Hz, 2H), 4.60(d, J=4.6 Hz, 1H), 6.28(dd, J=4.6 Hz, J=10 Hz, 1H), 6.97(s, 1H), 7.00(s, 1H), 7.2–7.5(m, 25H), 7.89(d, J=10 Hz, 1H), 8.5(brs, 1H). IR ν(CHCl3) cm−1: 3400, 1802, 1718, 1686, 1543, 1369, 1218, 1154.

7) Acyl=(Z)-2-(2-t-butoxycarbonylaminothiazol-4-yl)-2-trityloxyiminoacetyl Het=1-methyl-5-tetrazolyl (3E1-1-2)

1. To a solution of 7β-[(Z)-2-(2-t-butoxycarbonylaminothiazol-4-yl)-2-trityloxyiminoacetyl]amino-3-mercapto-3-cephem-4-carboxylic acid diphenylmethyl ester 1β-oxide (purity 92%: 3.0 g: 3.0 mMol.) in tetrahydrofuran (20 ml) is added a solution of silver nitrate (560 mg: 3.3 mMol.) in water (3 ml) under ice cooling, and the mixture is stirred for 20 minutes. The reaction mixture is diluted with water, and extracted with dichloromethane. The extract is washed with water, dried over sodium sulfate, filtered, and concentrated to give 7β-[(Z)-2-(2-t-butoxycarbonylaminothiazol-4-yl)-2-trityloxyiminoacetyl]amino-3argentiothio-3-cephem-4-carboxylic acid diphenylmethyl ester 1β-oxide as yellow brown foam (3.37 g).

2. To a solution of this silver salt in hexamethylphosphoramide (20 ml) is added a solution of 5-iodomethylthio-1-methyltetrazole (1.33 g) in hexamethylphosphoramide (3 ml), and the mixture is stirred at room temperature for 16 hours. The reaction mixture is diluted with brine and extracted with ethyl acetate. After filtering off the insoluble material, the extract is washed with water, dried over sodium sulfate, filtered, and concentrated. The residue is purified by silica gel column chromatography (toluene: ethyl acetate=3:1–2:1) to give 7β-[(Z)-2-(2-t-butoxycarbonylaminothiazol-4-yl)-2-trityloxyiminoacetyl]amino-3-(1-methyl-5-tetrazolyl)thiomethylthio-3-cephem-4-carboxylic acid diphenylmethyl ester 1β-oxide as brown foam (773 mg). Yield: 24%.

NMR δ(CDCl3) ppm: 1.48(s, 9H), 3.75(s, 3H), 3.73, 3.89(ABq, J=17.6 Hz, 2H), 4.22, 4.76(ABq, J=14.2 Hz, 2H), 4.50(d, J=4.6 Hz, 1H), 6.27(dd, J=4.6 Hz, J=10.2 Hz, 1H), 6.97(s, 1H), 7.00(s, 1H), 7.10–7.50(m, 25H), 7.73(d, J=10.2 Hz, 1H), 8.48(brs, 7H). IR ν(CHCl3) cm−1: 3400, 1802, 1718, 1686, 1543, 1510, 1493, 1446, 1369, 1275, 1227, 1154, 1031.

8) Acyl=(Z)-2-(2-t-butoxycarbonylaminothiazol4-yl)-2-trityloxyiminoacetyl Het=2-methyltetrazol-5-yl (4E3-3)

To a solution of 7β-[(Z)-2-(2-t-butoxycarbonylaminothiazol-4-yl)-2-trityloxyiminoacetylamino]-3-argentiothio-3-cephem-4-carboxylic acid diphenylmethyl ester 1-oxide (3.37 g: 3 mMol.) in hexamethylphosphoramide (20 ml) is added a solution of 5-iodomethylthio-2-methyltetrazole (1.43 g) in hexamethylphosphoramide (3 ml), and the mixture is stirred at room temperature for 3 hours. The reaction mixture is diluted with saturated brine and ethyl acetate and filtered. The organic layer of the filtrate is taken, washed with brine, dried over sodium sulfate, and concentrated. The residue is purified by silica gel chromatography (toluene: ethyl acetate=4:1–3:1) to give 7β-[(Z)-2-(2-t-butoxycarbonylaminothiazol-4-yl)-2-trityloxyiminoacetylamino]-3-(2-methyltetrazol-5ylthiomethylthio)-3-cephem-4-carboxylic acid diphenylmethyl ester 1-oxide (1.43 g) as yellow foam. Yield: 45%.

NMR δ(CDCl3) ppm: 1.47(s, 9H), 3.50, 4.02(ABq, J=17.9 Hz, 2H), 4.22(s, 3H), 4.24, 4.41(ABq, J=13.9 Hz, 2H), 4.49(d, J=4.8 Hz, 1H), 6.27(dd, J=4.8 Hz, J=10.0 Hz, 1H), 6.95(s, 1H), 6.99(s, 1H), 7.2–7.5(m, 25H), 7.91(d, J=10.0 Hz, 1H), 8.45(brs, 1H). IR ν(CHCl3) cm−1: 3410, 1806, 1725, 1690, 1543, 1510, 1496, 1450, 1382, 1372, 1320, 1044.

Example 3 modifications at Het

1) Removing trityl from trityl-1,2,4-triazole ring (4E4)

To a solution of 7β-[(Z)-2-(2-t-butoxycarbonylaminothiazol-4-yl)-2-trityloxyiminoacetylamino]-3-(trityl-1,2,4-triazol-3-ylthiomethylthio)-3-cephem-4-carboxylic acid diphenylmethyl ester 1-oxide (11.3 g) in acetone (60 ml) under ice cooling is added toluene-p-sulfonic acid monohydrate (1.68 g: 8.83 mMol.), and the mixture is stirred at room temperature for 4 hours. The reaction mixture is diluted with ethyl acetate, washed with aqueous 5% sodium hydrogen carbonate and brine, dried over sodium sulfate, and concentrated. The residue is purified by silica gel chromatography (toluene: ethyl acetate=1:1–1:2) to give 7β-[(Z)-2-(2-t-butoxycarbonylaminothiazol-4-yl)-2-trityloxyiminoacetylamino]-3-(1,2,4-triazol-3-ylthiomethylthio)-3-cephem-4-carboxylic acid diphenylmethyl ester 1-oxide (2.84 g) as brown foam. Yield: 31%.

NMR δ(CDCl3-CD3OD) ppm: 1.51(s, 9H), 3.58, 4.06(ABq, J=17.8 Hz, 2H), 4.30(s, 2H), 4.62(d, J=4.7 Hz, 1H), 6.22(d, J=4.7 Hz, 1H), 6.89 (s, 1H), 7.03(s, 1H), 7.15–7.4(m, 25H), 8.01(s, 1H). IR ν(CHCl3) cm−1: 3380, 3200br, 1803, 1720, 1690, 1547, 1510, 1497, 1450, 1372, 1040.

2) methylations of 1,2,3-triazole ring at position 1, 2 and 3 (1E6)

To a solution of 7β-[(Z)-2-(2-t-butoxycarbonylaminothiazol-4-yl)-2-trityloxyiminoacetamido]-3-(1,2,3-triazol-4-yl)thiomethylthio-3-cephem-4-carboxylic acid diphenylmethyl ester (6.00 g: 5.87 mMol.) in a mixture of dichloromethane (60 ml) and tetrahydrofuran (30 ml) is added at −50° C. diisopropylethylamine (1.12 g: 6.43 mMol.). After stirring at −40°—−50° C. for 3 minutes, trifluoromethanesulfonic acid methyl ester (0.73 ml: 6.45 mMol.) is added to the mixture. After stirring at the same temperature for 30 minutes, the reaction mixture is quenched with 10% hydrochloric acid (2.4 ml), diluted with water, and extracted with ethyl acetate. The extract is washed with water and brine, dried over sodium sulfate, and concentrated under reduced pressure. The residue is purified by silica gel chromatography (toluene: ethyl acetate=3:2) to give 7β-[(Z)-2-(2-t-butoxycarbonylaminothiazol-4-yl)-2-trityloxyiminoacetamido]-3-(3-methyl-1,2,3-triazol-4-yl)thiomethylthio-3-cephem-4-carboxylic acid diphenylmethyl ester [1.84 g: Yield: 30%. NMR δ(CDCl3-CD3OD) ppm: 1.52(s, 9H), 3.43, 3.55(ABq, J=17.3 Hz, 2H), 3.87, 3.94(ABq, J=13.7 Hz, 2H), 3.95(s, 3H), 5.12 (d, J=4.8 Hz, 1H), 5.99 (d, J=4.8 Hz, 1H), 6.96 (s, 1H), 7.06(s, 1H), 7.15–7.50(m, 25H), 7.73(s, 1H). IR ν(CHCl3) cm−1: 3398, 3300, 1784, 1714, 1683, 1540, 1490, 1443, 1366, 1277, 1220, 1153, 1114, 1077, 970, 910.], 7β-[(Z)-2-(2-t-butoxycarbonylaminothiazol-4-yl)-2-trityloxyiminoacetamido]-3-(1-methyl-1,2,3-triazol-4-yl)thiomethylthio-3-cephem-4-carboxylic acid diphenylmethyl ester (2.71 g: Yield: 46%), and 7β-[(Z)-2-(2-t- butoxycarbonylamino-4-thiazolyl)-2-trityloxy-iminoacetamido]-3-(2-methyl-1,2,3-triazol-4-yl)-thiomethylthio-3-cephem-4-carboxylic acid diphenylmethyl ester (0.51 g: Yield: 8%).

3) methylations of 1,2,4-triazole ring (4E5)

To a solution of 7β-[(Z)-2-(2-t-butoxycarbonylamino-thiazol-4-yl)-2-trityloxyiminoacetylamino]-3-(1,2,4-triazol-3-ylthiomethylthio)-3-cephem-4-carboxylic acid diphenylmethyl ester 1-oxide (2.71 g: 2.63 mMol.) in tetrahydrofuran (50 ml) at −78° C. is added a solution of lithium bis(trimethylsilyl)amide in tetrahydrofuran (1M: 2.9 ml), and the mixture is stirred at −78° C. for 10 minutes, mixed with trifluoromethanesulfonic acid methyl ester (0.33 ml: 2.92 mMol.), and stirred at −78° C. for 30 minutes. The reaction mixture is mixed with 10% hydrochloric acid (2.1 ml), diluted with water, and extracted with ethyl acetate. The extract is washed with aqueous sodium hydrogen carbonate and brine, dried over sodium sulfate, and concentrated. The residue is purified by silica gel chromatography (ethyl acetate) to give 7β-[(Z)-2-(2-t-butoxycarbonylaminothiazol-4-yl)-2-trityloxyiminoacetylamino]-3-(4-methyl-1,2,4-triazol-3-ylthiomethylthio)-3-cephem-4-carboxylic acid diphenylmethyl ester 1-oxide (0.73 g) as pale brown foam. Yield: 27%. NMR δ(CDCl$_3$-CD$_3$OD) ppm: 1.51(s, 9H), 3.31(s, 3H), 3.85(s, 2H), 4.12, 4.70(ABq, J=14.6 Hz, 2H), 4.74(d, J=4.8 Hz, 1H), 6.26(d, J=4.8 Hz, 1H), 6.96(s, 1H), 7.01(s, 1H), 7.2–7.5(m, 25H), 8.11(brs, 1H). IR ν(CHCl$_3$) cm$^{-1}$: 3400, 1805, 1722, 1690, 1545, 1507, 1497, 1450, 1372, 1040.

Example 4 sulfoxide

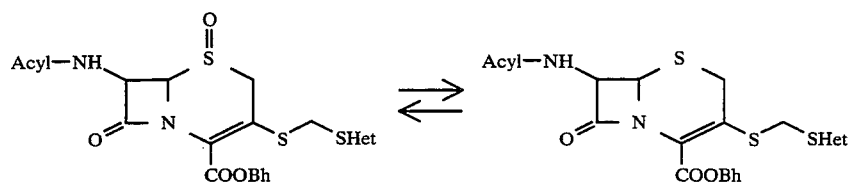

1) Reduction: Acyl=(Z)-2-(2-t-butoxycarbonylamino-thiazol-4-yl)-2-trityloxyiminoacetyl Het=1-methyl-1,2,4-triazol-3-yl (4E6-2)

To a solution of 7β-[(Z)-2-(2-t-butoxycarbonylamino-thiazol-4-yl)-2-trityloxyiminoacetylamino]-3-(1-methyl-1,2,4-triazol-3-ylthiomethylthio)-3-cephem-4-carboxylic acid diphenylmethyl ester 1-oxide (1.78 g: 1.69 mMol.) in dimethylformamide (15 ml) at −20° C. is added phosphorus trichloride (0.42 ml: 4.18 mMol.), and the mixture is stirred at the same temperature for 20 minutes. The reaction mixture is poured into two layers of cold aqueous sodium hydrogen carbonate and ethyl acetate. The organic layer is taken, washed with water and brine, dried over sodium sulfate, and concentrated. The residue is purified by silica gel chromatography (toluene: ethyl acetate=2:1) to give 7β-[(Z)-2-(2-t-butoxycarbonylaminothiazol-4-yl)-2-tritylox-yiminoacetamido]-3-(l-methyl-1,2,4-triazol-3-ylthiomethylthio)-3-cephem-4-carboxylic acid diphenylmethyl ester (1.59 g) as brown foam. Yield: 91%.

NMR δ(CDCl$_3$) ppm: 1.50(s, 9H), 3.41, 3.49(ABq, J=17.8 Hz, 2H), 3.76(s, 3H), 4.25(s, 2H), 5.05(d, J=4.6 Hz, 1H), 5.85(dd, J=4.6 Hz, J=8.2 Hz, 1H), 6.89(s, 1H), 7.00(s, 1H), 7.2–7.5(m, 25H), 7.77(d, J=8.2 Hz, 1H), 7.89(s, 1H), 9.0–9.3(brs, 1H). IR ν(CHCl$_3$) cm$^{-1}$: 3410, 1790, 1725, 1690, 1542, 1509, 1496, 1449, 1372.

2) Reduction: Acyl=(Z)-2-(2-t-butoxycarbonylamino-thiazol-4-yl)-2-trityloxyiminoacetyl Het=2-methyl-1,2,4-triazol-3-yl (4E6-1)

To a solution of 7β-[(Z)-2-(2-t-butoxycarbonylamino-thiazol-4-yl)-2-trityloxyiminoacetylamino]-3-(2-methyl-1,2,4-triazol-3-ylthiomethylthio)-3-cephem-4-carboxylic acid diphenylmethyl ester 1-oxide (1.73 g: 1.64 mMol.) in dimethylformamide (15 ml) is added at −20° C. phosphorus trichloride (0.41 ml: 4.08 mMol.), and the mixture is stirred at the same temperature for 20 minutes. The reaction mixture is poured into cold two layers of aqueous sodium hydrogen carbonate and ethyl acetate and stirred. The organic layer is taken, washed with water and brine, dried over sodium sulfate, and concentrated. The residue is purified by silica gel chromatography (toluene: ethyl acetate=2:1) to give 7β-[(Z)-2-(2-t-butoxycarbonylaminothiazol-4-yl)-2-trityloxyiminoacetamido]-3-(2-methyl-1,2,4-triazol-3-ylthiomethylthio)-3-cephem-4-carboxylic acid diphenylmethyl ester (1.60 g) as dark brown foam. Yield: 94%.

NMR δ(CDCl$_3$) ppm: 1.49(s, 9H), 3.37, 3.46(ABq, J=17.9 Hz, 2H), 3.69(s, 3H), 4.29, 4.48(ABq, J=13.4 Hz, 2H), 5.01(d, J=4.6 Hz, 1H), 5.91(dd, J=4.6 Hz, J=8.6 Hz, 1H), 6.93(s, 1H), 6.95(s, 1H), 7.2–7.5(m, 25H), 7.83(d, J=8.6 Hz, 1H), 7.84(s, 1H), 9.15–9.3(brs, 1H). IR ν(CHCl$_3$) cm$^{-1}$: 3420, 1790, 1724, 1690, 1542, 1497, 1450, 1372.

3) Reduction: Acyl=(Z)-2-(2-t-butoxycarbonylamino-thiazol-4-yl)-2-trityloxyiminoacetyl Het=4-methyl-1,2,4-triazol-3-yl (4E6-4)

To a solution of 7β-[(Z)-2-(2-t-butoxycarbonylamino-thiazol-4-yl)-2-trityloxyiminoacetylamino]-3-(4-methyl-1,2,4-triazol-3-ylthiomethylthio)-3-cephem-4-carboxylic acid diphenylmethyl ester 1-oxide (706 mg: 0.671 mMol.) in dimethylformamide (8 ml) is added phosphorus trichloride (0.17 ml: 1.69 mMol.), and the mixture is stirred at −20° C. for 30 minutes. The reaction mixture is poured into ice-cold two layers of aqueous 5% sodium hydrogen carbonate and ethyl acetate. The organic layer is taken, washed with water and brine, dried over sodium sulfate, and concentrated. The residue is purified by silica gel chromatography (ethyl acetate) to give 7β-[(Z)-2-(2-t-butoxycarbonylaminothiazol-4-yl)-2-trityloxyiminoacetylamino]-3-(4-methyl-1,2,4-triazol-3-ylthio)methylthio-3-cephem-4-carboxylic acid diphenylmethyl ester (404 mg) as pale brown foam. Yield: 58%.

NMR δ(CDCl$_3$) ppm: 1.46(s, 9H), 3.31(s, 3H), 3.43, 3.56(ABq, J=17.2 Hz, 2H), 4.34, 4.67(ABq, J=14.2 Hz, 2H), 5.04(d, J=5.0 Hz, 1H), 5.94(dd, J=5.0 Hz, J=8.5 Hz, 1H), 6.91(s, 1H), 6.95(s, 1H), 7.2–7.5(m, 25H), 8.05(s, 1H), 8.27(d, J=8.5 Hz, 1H), 9.7–10.1(brs, 1H). IR ν(CHCl$_3$) cm$^{-1}$: 3410, 1789, 1723, 1689, 1542, 1507, 1495, 1448, 1370.

4) Reduction: Acyl=(Z)-2-(2-t-butoxycarbonylamino-thiazol-4-yl)-2-trityloxyiminoacetyl Het=1,2,3-thiadiazol-5-yl (3E2-1)

To a solution of 7β-[(Z)-2-(2-t-butoxycarbonylaminothiazol-4-yl)-2-trityloxyimino acetyl]amino-3-(1,2,3-thiadiazol-5-yl)thiomethylthio-3-cephem-4-carboxylic acid diphenylmethyl ester 1β-oxide (1.46 g: 1.38 mMol.) in dimethylformamide (12 ml) cooling at −20° C. is added phosphorus trichloride (0.35 ml: 3.48 mMol.) and the mixture is stirred at −20° C. for 20 minutes. The reaction mixture is poured into 2 layers of 5% aqueous sodium hydrogen carbonate (35 ml) and ethyl acetate under ice cooling. The organic layer is taken, washed with water and brine, dried over sodium sulfate, filtered, and concentrated. The resulting residue is purified by silica gel column chromatography (toluene: ethyl acetate=5:1) to give, 7β-[(Z)-2-(2-t-butoxycarbonylaminothiazol-4-yl)-2-trityloxyiminoacetyl]amino-3-(1,2,3-thiadiazol-5-yl)thiomethylthio-3-cephem-4-carboxylic acid diphenyl methyl ester as yellow foam (1.24 g). Yield: 86%.

NMR δ(CDCl$_3$-CD$_3$OD) ppm: 1.52(s, 9H), 3.51, 3.67(ABq, J=17.6 Hz, 2H), 4.00, 4.16(ABq, J=13.7 Hz, 2H), 5.13(d, J=5.0 Hz, 1H), 6.02(d, J=5.0 Hz, 1H), 6.99(s, 1H), 7.05(s, 1H), 7.15–7.50(m, 25H), 8.51 (s, 1H). IR ν(CHCl$_3$) cm$^{-1}$: 3400, 1789, 1718, 1686, 1543, 1492, 1445, 1369, 1277, 1225, 1154.

5) Reduction: Acyl=(Z)-2-(2-t-butoxycarbonylaminothiazol-4-yl)-2-trityloxyiminoacetyl   Het=1,3,4-thiadiazol-2-yl (2E2-1)

To a solution of 7-[(Z)-2-(2-t-butoxycarbonylaminothiazol-4-yl)-2-trityloxyiminoacetamido]-3-(1,3,4-thiadiazol-2-ylthiomethylthio)-3-cephem-4-carboxylic acid diphenylmethyl ester 1β-oxide (760 mg) (0.72 mMol.) in dimethylformamide (7 ml) is added phosphorus trichloride (180 μl: 2.5 equivalents: 1.79 mMol.) at −30° C., and the mixture is stirred for 30 minutes. The reaction mixture is poured into aqueous 5% sodium hydrogen carbonate (70 ml) and extracted with ethyl acetate. The extract is washed with water, dried over sodium sulfate, and concentrated. The residue is purified by silica gel chromatography (toluene: ethyl acetate=4:1) to give 7-[(Z)-2-(2-t-butoxycarbonylaminothiazol-4-yl)-2-trityloxyiminoacetamido]-3-(1,3,4-thiadiazol-2-ylthiomethylthio)-3-cephem-4-carboxylic acid diphenylmethyl ester as pale yellow foam (544 mg). Yield: 73%.

NMR δ(CDCl$_3$) ppm: 1.50(s, 9H), 3.51, 3.67(ABq, J=17 Hz, 2H), 4.53, 4.58(ABq, J=14 Hz, 2H), 5.07(d, J=4.8 Hz, 1H), 5.98(dd, J=4.8 Hz, J=9 Hz, 1H), 6.97(s, 1H), 7.03(s, 1H), 7.2–7.5(m, 25H), 7.58(d, J=9 Hz, 1H), 8.6 (brs, 1H), 8.98(s, 1H). IR ν(CHCl$_3$) cm$^{-1}$: 3400, 1787, 1719, 1690, 1544, 1370, 1220, 1155.

6) Reduction: Acyl=(Z)-2-(2-t-butoxycarbonylaminothiazol-4-yl)-2-trityloxy-iminoacetyl   Het=2-methyl-1,3,4-thiadiazol-5-yl (2E2-2)

To a solution of 7-[(Z)-2-(2-t-butoxycarbonylaminothiazol-4-yl)-2-trityloxyiminoacetamido]-3-(2-methyl-1,3,4-thiadiazol-5-ylthiomethylthio)-3-cephem-4-carboxylic acid diphenylmethyl ester 1β-oxide (362 mg: 0.339 mMol.) in dimethylformamide (3 ml) is added phosphorus trichloride (85 μl: 2.5 equivalents: 0.85 mMol.) at −30° C., and the mixture is stirred for 30 minutes. The reaction mixture is poured into 5% sodium hydrogen carbonate (25 ml) and extracted with ethyl acetate. The extract is washed with water, dried over sodium sulfate, and concentrated. The residue is purified by silica gel chromatography (toluene: ethyl acetate=4:1) to give 7-[(Z)-2-(2-t-butoxycarbonylamino-4-thiazolyl)-2-trityloxyiminoacetamido]-3-(2-methyl-1,3,4-thiadiazol-5-ylthiomethylthio)-3-cephem-4-carboxylic acid diphenylmethyl ester as pale yellow foam (246 mg). Yield: 69%.

NMR δ(CDCl$_3$) ppm: 1.50(s, 9H), 2.69(s, 3H), 3.53, 3.68(ABq, J=18 Hz, 2H), 4.50(s, 2H), 5.07(d, J=5 Hz, 1H), 6.00(dd, J=5 Hz, J=9 Hz, 1H), 6.97 (s, 1H), 7.03(s, 1H), 7.2–7.5(m, 25H), 7.69(d, J=9 Hz, 1H), 8.85(brs, 1H). IR ν(CHCl$_3$) cm$^{-1}$: 3400, 1787, 1720, 1690, 1543, 1369, 1219, 1155.

7) Reduction Acyl=(Z)-2-(2-t-butoxycarbonylaminothiazol-4-yl)-2-trityloxyiminoacetyl   Het=1-methyl-5-tetrazolyl (3E2-2)

To a solution of 7β-[(Z)-2-(2-t-butoxycarbonylaminothiazol-4-yl)-2-trityloxyiminoacetyl]amino-3-(1-methyl-5-tetrazolyl)thiomethylthio-3-cephem-4-carboxylic acid diphenylmethyl ester 1β-oxide (745 mg: 0.708 mMol.) in dimethylformamide (7 ml) cooling at −20° C. is added phosphorus trichloride (0.18 ml: 1.79 mMol.), and the mixture is stirred at −20° C. for 20 minutes. The reaction mixture is poured into 2 layers of 5% aqueous sodium hydrogen carbonate (20 ml) and ethyl acetate under ice cooling. The organic layer is taken, washed with water and brine, dried over sodium sulfate, filtered, and concentrated. The residue is purified by silica gel column chromatography (toluene: ethyl acetate=3:1) to give 7β-[(Z)-2-(2-t-butoxycarbonylaminothiazol-4-yl)-2-trityloxyiminoacetyl]amino-3-(1-methyl-5-tetrazolyl)thiomethylthio-3-cephem-4-carboxylic acid diphenylmethyl ester as brown foam (608 mg). Yield: 83%.

NMR δ(CDCl$_3$-CD$_3$OD) ppm: 1.52(s, 9H), 3.57, 3.73(ABq, J=17.6 Hz, 2H), 3.81(s, 3H), 4.56(s, 2H), 5.09(d, J=5.0 Hz, 1H), 6.02(d, J=5.0 Hz, 1H), 6.94(s, 1H), 7.05 (s, 1H), 7.15–7.50(m, 25H). IR ν(CHCl$_3$) cm$^{-1}$: 3400, 1788, 1717, 1686, 1543, 1492, 1446, 1369, 1279, 1227, 1154.

8) Reduction: Acyl=(Z)-2-(2-t-butoxycarbonylaminothiazol-4-yl)-2-trityloxyiminoacetyl   Het=2-methyltetrazol-5-yl (4E6-3)

To a solution of 7β-[(Z)-2-(2-t-butoxycarbonylaminothiazol-4-yl)-2-trityloxyiminoacetylamino]-3-(2-methyltetrazol-5-yl thiomethylthio)-3-cephem-4-carboxylic acid diphenylmethyl ester 1-oxide (1.38 g: 1.31 mMol.) in dimethylformamide (15 ml) at −20° C. is added phosphorus trichloride (0.33 ml: 3.28 mMol.), and the mixture is stirred at the same temperature for 20 minutes. The reaction mixture is poured into cold two layers of aqueous sodium hydrogen carbonate and ethyl acetate and stirred. The organic layer is taken, washed with water and brine, dried over sodium sulfate and concentrated. The residue is purified by silica gel chromatography (toluene: ethyl acetate=5:1) to give 7β-[(Z)-2-(2-t-butoxycarbonylaminothiazol-4-yl)-2-trityloxyiminoacetylamino]-3-(2-methyltetrazol-5-ylthiomethylthio)-3-cephem-4-carboxylic acid diphenylmethyl ester (1.20 g) as yellow foam. Yield: 88%.

NMR δ(CDCl$_3$) ppm: 1.50(s, 9H), 3.40(brs, 2H), 4.25(s, 3H), 4.28(s, 2H), 5.07(d, J=4.8 Hz, 1H), 5.85(dd, J=4.8 Hz, J=8.2 Hz, 1H), 6.89(s, 1H), 6.98(s, 1H), 7.2–7.5(m, 25H), 7.57(d, J=8.2 Hz, 1H), 8.7–8.9(brs, 1H). IR ν(CHCl$_3$) cm$^{-1}$: 3420, 1792, 1725, 1690, 1542, 1497, 1450, 1392, 1372, 1323.

9) Oxidation:   Acyl=2-(2-t-butoxycarbonylaminothiazol-4-yl)-2-trityloxyiminoacetyl   Het=1,2,3-triazol-4-yl To a solution of 7β-[(Z)-2-(2-t-butoxycarbonylaminothiazol-4-yl)-2-trityloxyiminoacetamido]-3-(1,2,3-triazol-4-yl)thiomethylthio-3-cephem-4-carboxylic acid diphenylmethyl ester (511 mg: 0.5 mMol.) in a mixture of dichloromethane (10 ml) and methanol (10 ml) is added m-chloroperbenzoic acid (purity: 80%: 54 mg: 0.25 mMol.) at −30° C., and the mixture is stirred for 1 hour. The reaction mixture is diluted with aqueous 5% sodium thiosulfate and extracted with ethyl acetate. The extract solution was washed with aqueous sodium hydrogencarbonate, diluted hydrochloric acid, and brine, dried over sodium sulfate, and concentrated under reduced pressure. The residue was purified by silica gel chromatography (toluene-ethyl acetate=2:1 to 1:1) to give 7β-[(Z)-2-(2-t-butoxycarbonylaminothiazol-4-yl)-2-trityloxyiminoacetamido]-3-(1,2,3-triazol-4-yl)thiomethylthio-3-cephem-4-carboxylic acid diphenylmethyl ester 1-oxide (232 mg). Yield: 45%. A part of the starting material (236 mg: 48%) was recovered.

NMR δ(CDCl₃) ppm: 1.42(s, 9H), 3.45, 3.94 (ABq, J=18 Hz, 2H), 3.83, 4.09(ABq, J=14 Hz, 2H), 4.54(d, J=4.8 Hz, 1H), 6.18(dd, J=4.8 Hz, J=9 Hz, 1H), 6.94(s, 1H), 6.96(s, 1H), 7.2–7.6(m, 26H), 8.02(d, J=9 Hz, 1H). IR ν(CHCl₃) cm⁻¹: 3380, 3200, 1799, 1716, 1690, 1545, 1370, 1155.

Example 5 amidation

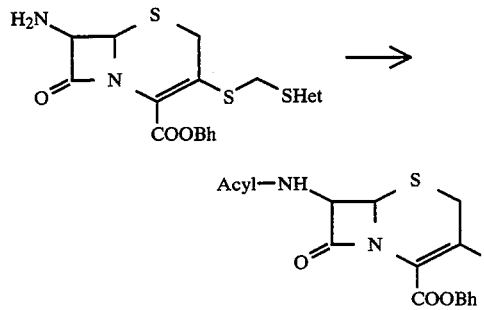

1) Acyl=difluoromethylthioacetyl Het=1,2,3-triazol-4-yl (4E1-5)

To a solution of 7β-amino-3-(1,2,3-triazol-4-ylthiomethylthio)-3-cephem-4-carboxylic acid diphenylmethyl ester (550 mg: 1.08 mMol.) and difluoromethylthioacetic acid (160 mg: 1.13 mMol.) in dichloromethane (8 ml) cooling at −30° C. are added N-methylmorpholine (0.27 ml: 2.46 mMol.) and phenyl dichlorophosphate (0.19 ml: 1.27 mMol.), and the mixture is stirred at −30° C. for 1 hour. The reaction mixture is mixed with 10% hydrochloric acid (1 ml), diluted with water, and extracted with ethyl acetate. The extract is washed with aqueous saline, dried over sodium sulfate, and concentrated. The residue is purified by silica get column chromatography (toluene: ethyl acetate=1:1) to give 7β-difluoromethylthioacetamido-3-(1,2,3-triazol-4-ylthiomethyl- thio)-3-cephem-4-carboxylic acid diphenylmethyl ester (475 mg) as pale yellow foam. Yield: 69%.

NMR δ(CDCl₃) ppm: 3.56(s, 2H), 3.59(s, 2H), 4.05(s, 2H), 4.99(d, J=4.8 Hz, 1H), 5.79(dd, J=8.7 Hz, J=4.8 Hz, 1H), 6.90(s, 1H), 6.91(t, J=56.2 Hz, 1H), 7.1–7.5(m, 10H), 7.59(s, 1H), 7.68(d, J=8.7 Hz, 1H). IR ν(CHCl₃) cm⁻¹: 3430, 3300br, 1785, 1690, 1512, 1496, 1454, 1378, 1333.

2) Acyl=N-t-butoxycarbonyl-2-phenylglycyl Het=trityl-1,2,3-triazol-4-yl (4E1-2)

To a solution of 7β-amino-3-(trityl-1,2,3-triazol-4-ylthiomethylthio)-3-cephem-4-carboxylic acid diphenylmethyl ester (914 mg: 1.21 mMol.) and D-N-t-butoxycarbonyl-2-phenylglycin (320 mg: 1.27 mMol.) in dichloromethane (9 ml) cooling at −30° C. is added N-methylmorpholine (0.31 ml: 2.82 mMol.) and phenyl dichlorophosphate (0.22 ml: 1.47 mMol.), and the mixture is stirred at the same temperature for 50 minutes. The reaction mixture is mixed with 10% hydrochloric acid (1 ml), diluted with water, and extracted with ethyl acetate. The extract is washed with brine, dried over sodium sulfate, and concentrated. The residue is purified by silica gel chromatography (toluene: ethyl acetate=10:1) to give 7β-(D-N-t-butoxycarbonyl-2-phenylglycylamino)-3-(trityl-1,2,3-triazol-4-ylthiomethylthio)-3-cephem-4-carboxylic acid diphenylmethyl ester (501 mg) as colorless foam. Yield: 42%.

NMR δ(CDCl₃) ppm: 1.42(s, 9H), 3.22, 3.44(ABq, J=17.5 Hz, 2H), 3.93, 3.98(ABq, J=13.3 Hz, 2H), 4.81(d, J=4.8 Hz, 1H), 5.20(d, J=6.0 Hz, 1H), 5.62(d, J=6.0 Hz, 1H), 5.76(dd, J=4.8 Hz, J=9.1 Hz, 1H), 6.50(d, J=9.1 Hz, 1H), 6.91(s, 1H), 7.05–7.15(m, 6H), 7.25–7.45(m, 24H), 7.59(s, 1H). IR ν(CHCl₃) cm⁻¹: 3420, 1788, 1710, 1697, 1495, 1455, 1448, 1370.

3). Acyl=D-mandeloyl Het=trityl-1,2,3-triazol-4-yl (4E1-3)

To a solution of 7β-amino-3-(trityl-1,2,3-triazol-4-ylthiomethylthio)-3-cephem-4-carboxylic acid diphenylmethyl ester (800 mg: 1.06 mMol.) and D-(−)-mandelic acid (242 mg: 1.59 mMol.) in dichloromethane (4 ml) is added dicyclohexylcarbodiimide (328 mg: 1.59 mMol.), and the mixture is stirred under ice cooling for 1 hour. The reaction mixture is concentrated, diluted with ethyl acetate, and filtered to remove solid. The filtrate is washed with brine, dried over sodium sulfate, and concentrated under reduced pressure. The residue is purified by Lobar column chromatography (toluene: ethyl acetate=2:1) to give 7β-D-mandelamido-3-(trityl-1,2,3-triazol-4-ylthiomethylthio)-3-cephem-4-carboxylic acid diphenylmethyl ester (466 mg) as yellow foam. Yield: 50%.

NMR δ(CDCl₃) ppm: 3.41(d, J=3.3 Hz, 1H), 3.57, 3.78(ABq, J=17.4 Hz, 2H), 4.06, 4.16(ABq, J=13.4 Hz, 2H), 4.91(d, J=4.8 Hz, 1H), 5.15(d, J=3.3 Hz, 1H), 5.69(dd, J=4.8 Hz, J=9.2 Hz, 1H), 6.88(s, 1H), 6.98(d, J=9.2 Hz, 1H), 7.05–7.15(m, 6H), 7.25–7.4(m, 24H), 7.45(s, 1H). IR ν(CHCl₃) cm⁻¹: 3600, 3400, 1788, 1725, 1692, 1602, 1509, 1495, 1450, 1375, 1315.

4) Acyl=(Z)-2-(2-t-butoxycarbonylaminothiazol-4-yl)acetyl Het=trityl-1,2,3-triazol-4-yl (4E1-1)

To a solution of 7β-amino-3-(trityl-1,2,3-triazol-4-ylthiomethyl-thio)-3-cephem-4-carboxylic acid diphenylmethyl ester (800 mg: 1.06 mMol.) and 2-(2-t-butoxycarbonylaminothiazol-4-yl)acetic acid (287 mg: 1.11 mMol.) in dichloromethane (8 ml) cooling at −30° C. are added N-methylmorpholine (0.27 ml: 2.46 mMol.) and phenyl dichlorophosphate (0.19 ml: 1.27 mMol.), and the mixture is stirred at −30° C. for 40 minutes. The reaction mixture is quenched with 10% hydrochloric acid (1 ml), diluted with water, and extracted with ethyl acetate. The extract is washed with brine, dried over sodium sulfate, and concentrated. The residue is purified by silica gel chromatography (toluene: ethyl acetate=3:1) to give 7β-[2-(2-t-butoxycarbonylaminothiazol-4-yl)acetamido]-3-(trityl-1,2,3-triazol-4-ylthiomethylthio)-3-cephem-4-carboxylic acid diphenylmethyl ester (812 mg) as pale yellow foam. Yield: 77%.

NMR δ(CDCl₃) ppm: 1.57(s, 9H), 3.41(s, 2H), 3.72, 3.75(ABq, J=17.8 Hz, 2H), 4.02, 4.06(ABq, J=13.6 Hz, 2H), 4.79(d, J=4.6 Hz, 1H), 5.54(dd, J=8.0 Hz, J=4.6 Hz, 1H), 6.57(s, 1H), 6.76(s, 1H), 7.05–7.15(m, 6H), 7.25–7.5 (m, 19H), 7.44 (s, 1H), 7.76(d, J=8.0 Hz, 1H).

IR ν(CHCl₃) cm⁻¹: 3420, 3340, 3170, 1780, 1718, 1672, 1604, 1545, 1497, 1450, 1372, 1328.

5) Acyl=2-(2-t-butoxycarbonylaminothiazol-4-yl)glyoxyl (4E1-4) Het=trityl-1,2,3-triazol-4-yl To a solution of 7β-amino-3-(trityl-1,2,3-triazol-4yl-thiomethylthio)-3-cephem-4-carboxylic acid diphenylmethyl ester (800 mg: 1.06 mMol.) and 2-(2-t-butoxycarbonylaminothiazol-4-yl)glyoxylic acid (303 mg: 1.11 mMol.) in dichloromethane (8 ml) cooling at −30° C. are added N-methylmorpholine (0.27 ml) (2.46 mMol.) and phenyl dichlorophosphate (0.19 ml: 1.27 mMol.), and the mixture is stirred at −30° C. for 1 hour. The reaction mixture is mixed with 10% hydrochloric acid (1 ml), diluted with water, and extracted with ethyl acetate. The extract is washed with brine, dried over sodium sulfate, and concentrated. The residue is purified by silica gel chromatography (toluene: ethyl acetate=2:1) to give 7β-[2-(2-t-butoxycarbonylaminothiazol-4-yl)-glyoxylylamino]-3-(trityl-1,2,3-triazol-4-ylthiomethylthio)-3-cephem-4-carboxylic acid diphenylmethyl ester (679 mg) as yellow foam. Yield: 64%.

NMR δ(CDCl₃) ppm: 1.55(s, 9H), 3.67, 3.85(ABq, J=17.1 Hz, 2H), 4.10, 4.21(ABq, J=13.3 Hz, 2H), 5.00(d, J=4.7 Hz, 1H), 5.70(dd, J=9.2 Hz, J=4.7 Hz, 1H), 6.91(s, 1H), 7.05–7.15(m, 6H), 7.2–7.45(m, 19H), 7.47(s, 1H), 8.19(d, J=9.2 Hz, 1H), 8.5–8.6(brs, 1H), 8.86(s, 1H). IR ν(CHCl₃) cm⁻¹: 3400, 1788, 1725, 1702, 1672, 1565, 1512, 1495, 1480, 1448, 1372.

6) Acyl=(Z)-2-(2-t-butoxycarbonylaminothiazol-4-yl)-2-trityloxyiminoacetyl Het=1,2,3-triazol-4-yl (1E01)

To a suspension of 7β-amino-3-(1,2,3-triazol-4-yl)thiomethylthio-3-cephem-4-carboxylic acid diphenylmethyl ester hydrochloride (110 mg: 0.2 mMol.) and (Z)-2-(2-t-butoxycarbonylaminothiazol-4-yl)-2-trityloxyiminoacetic acid (122 mg: 0.23 mMol.) in dichloromethane (3 ml) are added N-methylmorpholine (72 µl: 0.66 mMol.) and phenyl dichlorophosphate (33 µl: 0.22 mMol.) at −30° C. After stirring for 2 hours, the reaction mixture is diluted with 10% hydrochloric acid and extracted with ethyl acetate. The extract is washed with water, dried, purified by silica gel chromatography, and crystallized from toluene to give 7β-[(Z)-2-(2-t-butoxycarbonylaminothiazol-4-yl)-2-trityloxyiminoacetamido]-3-(1,2,3-triazol-4-yl)thiomethylthio-3-cephem-4-carboxylic acid diphenylmethyl ester (110 mg). m.p. 190°–200° C. (decomp.).

NMR δ(CDCl₃-CD₃OD) ppm: 1.53(s, 9H), 3.45, 3.63(ABq, J=17.2 Hz, 2H), 4.12, 4.15 (ABq, J=14.2 Hz, 2H), 5.08(d, J=5 Hz, 1H), 5.88(d, J=5 Hz, 1H), 6.98(s, 1H), 7.08(s, 1H), 7.2–7.5(m, 25H), 7.60(s, 1H). IR ν(KBr) cm⁻¹: 3390, 3210, 1800, 1725, 1688, 1555, 1495, 1449, 1375, 1275, 1245, 1225, 1155.

7) Acyl=(Z)-2-(2-tritylaminothiazol-4-yl) -2-(diphenylmethoxycarbonylmethoxyimino)acetyl Het=trityl-1,2,3-triazol-4-yl (4E1-6)

To a solution of 7β-amino-3-(trityl-1,2,3-triazol-4-ylthiomethyl-thio)-3-cephem-4-carboxylic acid diphenylmethyl ester (800 mg: 1.06 mMol.) and (Z)-2-(2-tritylaminothiazol-4-yl)-2-(diphenylmethoxycarbonylmethoxyimino)acetic acid (728 mg: 1.11 mMol.) in chloromethane (8 ml) cooling at −30° C. are added N-methylmorpholine (0.27 ml: 2.46 mMol.), phenyl dichlorophosphate (0.19 ml: 1.27 mMol.), and the mixture is stirred at −30° C. for 30 minutes. The reaction mixture is mixed with 10% hydrochloric acid (1 ml), diluted with water, and extracted with ethyl acetate. The extract washed with brine, dried over sodium sulfate, and concentrated. The residue is purified by silica gel chromatography (toluene: ethyl acetate=10:1) to give 7β-[(Z)-2-(2-tritylaminothiazol-4-yl)-2-(diphenylmethoxycarbonylmethoxyimino)acetamido]-3-(trityl-1,2,3-triazol-4-ylthiomethylthio)-3-cephem-4-carboxylic acid diphenylmethyl ester (1.07 g) as yellow foam. Yield: 73%.

NMR δ(CDCl₃) ppm: 3.32, 3.62(ABq, J=17.1 Hz, 2H), 4.07, 4.12(ABq, J=13.2 Hz, 2H), 4.90(d, J=5.0 Hz, 1H), 4.93, 5.03(ABq, J=17.0 Hz, 2H), 5.80 (dd, J=9.1 Hz, J=5.0 Hz, 1H), 6.81(s, 1H), 6.87(s, 1H), 6.93(s, 1H), 7.0–7.4(m, 51H), 7.45(s, 1H), 8.11(d, J=9.1 Hz, 1H). IR ν(CHCl₃) cm⁻¹: 3410, 1790, 1740, 1688, 1526, 1498, 1451, 1380.

8) Acyl=(Z)-2-(2-tritylaminothiazol-4-yl)-2-[(S)-1-diphenylmethoxycarbonylethoxyimino]acetyl Het=trityl-1,2,3-triazol-4-yl (4E1-7)

To a solution of 7β-amino-3-(trityl-1,2,3-triazol-4-ylthiomethylthio)-3-cephem-4-carboxylic acid diphenylmethyl ester (800 mg: 1.06 mMol.) and (Z)-2-(2-tritylaminothiazol-4-yl)-2-[(S)-1-diphenylmethoxy-carbonylethoxyimino]acetic acid (744 mg: 1.12 mMol.) in dichloromethane (8 ml) cooling at −30° C. are added N-methylmorpholine (0.27 ml: 2.46 mMol.) and phenyl dichlorophosphate (0.19 ml: 1.27 mMol.), and the mixture is stirred at −30° C. for 1 hour. The reaction mixture is mixed with 10% hydrochloric acid (1 ml), diluted with water, and extracted with ethyl acetate. The extract is washed with aqueous saline, dried over sodium sulfate, and concentrated. The residue is purified by silica gel chromatography (toluene: ethyl acetate=10:1) to give 7β-{(Z)-2-(2-tritylaminothiazol-4-yl)-2-[(S)-1-diphenylmethoxycarbonyl-ethoxyimino]acetamido}-3-(trityl-1,2,3-triazol-4-ylthiomethylthio)-3-cephem-4-carboxylic acid diphenylmethyl ester (1.05 g) as yellow foam. Yield: 70%.

NMR δ(CDCl₃) ppm: 1.65(d, J=7.2 Hz, 3H), 3.41, 3.66(ABq, J=16.8 Hz, 2H), 4.12, 4.16(ABq, J=13.4 Hz, 2H), 4.91(d, J=4.6 Hz, 1H), 5.20(q, J=7.2 Hz, 1H), 5.82(dd, J=8.7 Hz, J=4.6 Hz, 1H), 6.77(s, 1H), 6.85(s, 1H), 6.87 (s, 1H), 7.0–7.4(m, 51H), 7.45(s, 1H), 8.22(d, J=8.7 Hz, 1H). IR ν(CHCl₃) cm⁻¹: 3400, 1787, 1730, 1685, 1523, 1493, 1447, 1375.

9) Acyl=(Z)-2-(2-t-butoxycarbonylaminothiazol-4-yl)-2-(1-diphenylmethoxycarbonylvinyloxyimino)acetyl Het=trityl-1,2,3-triazol-4-yl (4E1-9)

To a solution of 7β-amino-3-(trityl-1,2,3-triazol-4-ylthiomethylthio)-3-cephem-4-carboxylic acid diphenylmethyl ester (800 mg: 1.06 mMol.) and (Z)-2-(2-t-butoxycarbonylaminothiazol-4-yl)-2-(]-diphenylmethoxycarbonylvinyloxyimino)acetic acid (dicyclohexylamine salt 786 mg: 1.12 mMol.) in dichloromethane (8 ml) cooling at −30° C. are added N-methylmorpholine (0.15 ml: 1.36 mMol.) and phenyl dichlorophosphate (0.19 ml: 1.27 mMol.), and the mixture is stirred at −30° C. for 40 minutes. The reaction mixture is mixed with 10% hydrochloric acid (1 ml), diluted with water, and extracted with ethyl acetate. The extract is washed with brine, dried over sodium sulfate, and concentrated. The residue is purified by silica gel column chromatography (toluene: ethyl acetate=5:1) to give 7β-[(Z)-2-(2-t-butoxycarbonylaminothiazol-4-yl)-2-(1-diphenylmethoxycarbonylvinyloxyimino)acetamido]-3-(trityl-1,2,3-triazol-4-ylthiomethylthio)-3-cephem-4-carboxylic acid diphenylmethyl ester (936 mg) as yellow foam. Yield: 70%.

NMR δ(CDCl₃) ppm: 1.53(s, 9H), 3.33, 3.51(ABq, J=18.0 Hz, 2H), 4.07(s, 2H), 4.80(d, J=4.8 Hz, 1H), 5.66(s, 1H), 5.73(dd, J=4.8 Hz, J=9.0 Hz, 1H), 5.89(s, 1H), 6.84(s, 1H), 6.93(s, 1H), 7.0–7.4(m, 36H), 7.45(s, 1H), 7.68(d, J=9.0 Hz, 1H), 8.7–9.1(brs, 1H). IR ν(CHCl₃) cm⁻¹: 3400, 1786, 1724, 1695, 1545, 1494, 1445, 1370.

10) Acyl=(Z)-2-(2-t-butoxycarbonylaminothiazol-4-yl)-2-(1-t-butoxycarbonyl-1-methylethoxyimino)acetyl Het=trityl-1,2,3-triazol-4-yl (4E1-8)

To a solution of 7β-amino-3-(trityl-1,2,3-triazol-4-ylthiomethylthio)-3-cephem-4-carboxylic acid diphenylmethyl ester (800 mg: 1.06 mMol.) and (Z)-2-(2-t-butoxycarbonylaminothiazol-4-yl)-2-(1-t-butoxycarbonyl-1-methylethoxyimino)acetic acid (479 mg: 1.12 mMol.) in dichloromethane (8 ml) cooling at −30° C. are added N-methylmorpholine (0.27 ml) (2.46 mMol.) and phenyl dichlorophosphate (0.19 ml: 1.27 mMol.), and the mixture is stirred at −30° C. for 50 minutes. The reaction mixture is mixed with 10% hydrochloric acid (1 ml), diluted with water, and extracted with ethyl acetate. The extract is washed with brine, dried over sodium sulfate, and concentrated. The residue is purified by silica gel column chromatography (toluene: ethyl acetate=10:1 to 5:1) to give 7β-[(Z)-2-(2-t-butoxycarbonylaminothiazol-4-yl)-2-(1-t-butoxycarbonyl-1-methylethoxyimino)acetamido]-3-(trityl-1,2,3-triazol-4-ylthiomethylthio)-3-cephem-4-carboxylic acid diphenylmethyl ester (855 mg) as yellow foam. Yield: 69%.

NMR δ(CDCl₃) ppm: 1.39(s, 9H), 1.53(s, 9H), 1.61(s, 3H), 1.63(s, 3H), 3.63, 3.84(ABq, J=17.3 Hz, 2H), 4.09, 4.20(ABq, J=13.4 Hz, 2H), 5.01(d, J=4.9 Hz, 1H), 5.94(dd, J=9.0 Hz, J=4.9 Hz, 1H), 6.88(s, 1H), 7.05–7.4(m, 26H), 7.46(s, 1H), 8.19(d, J=9.0 Hz, 1H), 8.1–8.4(brs, 1H). IR ν(CHCl₃) cm⁻¹: 3420, 1788, 1725, 1687, 1545, 1495, 1445, 1371.

Example 6 structural variants

1) R²=methylene (4P3) (4E2-4) (4E7-17)

1. To a suspension of sodium azide (19.0 g: 0.283 Mol.) in dimethyl-formamide (130 ml) is added trityl chloride (76.0 g: 0.273 Mol.), and the mixture is stirred at room temperature for 5 hours. The reaction mixture is diluted with water and extracted with ether. The extract is washed with brine, dried over sodium sulfate, and concentrated to give trityl azide. To a solution of this azide in acetone (300 ml) is added methyl propiolate (24 ml: 0.27 Mol.), and the mixture is heated under reflux for 6 days. The reaction mixture is cooled to the room temperature and diluted with ether. The separating crystals are collected by filtration to give 1-trityl-1,2,3-triazol-4-ylcarboxylic acid methyl ester (62.0 g) as colorless crystals.

Yield: 62%. mp. 189° to 190° C. NMR δ(CDCl₃) ppm: 3,93(s, 3H), 7.05–7.15(m, 6H), 7.3–7.4(m, 9H), 8.02(s, 1H). IR ν(CHCl₃) cm⁻¹: 1722, 1544, 1492, 1444, 1338.

2. To a suspension of lithium aluminum hydride (6.17 g: 0.163 Mol.) in tetrahydrofuran (600 ml) under ice cooling is added 1-trityl-1,2,3-triazol-4-ylcarboxylic acid methyl ester (40.0 g: 0.108 Mol.), and the mixture is stirred at room temperature for 1 hour. To the reaction mixture is added dropwise aqueous tetrahydrofuran under ice cooling. The mixture is neutralized with 10% hydrochloric acid, filtered to remove insoluble material, diluted with ethyl acetate, washed with brine, dried over sodium sulfate, and concentrated. The resulting crystals are washed with ether to give 1-trityl-1,2,3-triazol-4-yl-methanol (33.4 g) as white crystals. Yield: 91%. mp. 200° to 201° C.

NMR δ(CDCl₃) ppm: 2.4–2.9(brs, 1H), 4.76(s, 2H), 7.05–7.15(m, 6H), 7.3–7.4(m, 9H), 7.43(s, 1H). IR ν(CHCl₃) cm⁻¹: 3600, 3600–3200br, 1600, 1490, 1443.

3. To a solution of 1-trityl-1,2,3-triazol-4-ylmethanol (8.00 g: 23.5 mMol.) in a mixture of dichloromethane (150 ml) and dimethylformamide (15 ml) at −40° C. are added triethylamine (3.9 ml: 28.0 mMol.) and methanesulfonyl chloride (2.2 ml: 28.4 mMol.), and the mixture is stirred at −30° to −40° C. for 25 minutes. The reaction mixture is diluted with water and extracted with ethyl acetate. The extract is washed with brine, dried over sodium sulfate, and concentrated. To a solution of the residue in acetone (150 ml) are added potassium thiol-acetate (4.02 g: 35.2 mMol.) and sodium iodide (7.03 g: 46.9 mMol.), and the mixture is stirred at room temperature for 2 hours. The reaction mixture is diluted with water and extracted with ethyl acetate. The extract is washed with water and brine, dried over sodium sulfate, and concentrated. The resulting crystals are washed with ether to give 4-acetylthioacetylthiomethyl-1-trityl-1,2,3-triazole (8.01 g) as white crystals. Yield: 86%. mp. 172° to 173° C.

NMR δ(CDCl₃) ppm: 2.32(s, 3H), 4.19(s, 2H), 7.05–7.15(m, 6H), 7.3–7.4(m, 10H). IR ν(CHCl₃) cm⁻¹: 1685, 1491, 1444.

4. To a suspension of litium aluminum hydride (1.07 g: 28.2 mMol.) in tetrahydrofuran (100 ml) under ice cooling is added 4-acetylthiomethyl-1-trityl-1,2,3-triazole (7.50 g: 18.8 mMol.), and the mixture is stirred at room temperature for 40 minutes. To the reaction mixture is added aqueous tetrahydrofuran dropwise, and the mixture is neutralized with 10% hydrochloric acid. The solution is filtered and the filtrate is diluted with ethyl acetate, washed with brine, dried over sodium sulfate, and concentrated. The residue is crystallized from ether and washed with ether to give 1-trityl-1,2,3-triazol-4-ylmethylmercaptan (5.14 g) as white crystals. Yield: 77%. mp. 140° to 141° C.

NMR δ(CDCl₃) ppm: 1.99(t, J=7.8 Hz, 1H), 3.84(d, J=7.8 Hz, 2H), 7.1–7.2(m, 6H), 7.3–7.4(m, 10H). IR ν(CHCl₃) cm⁻¹: 1491, 1444.

5. To a solution of 1-trityl-1,2,3-triazol-4-ylmethylmercaptan (3.00 g: 8.40 mMol.) in dimethylformamide (10 ml) is added sodium hydride (60% dispersion in oil: 370 mg: 9.25 mMol.), and the mixture is stirred for 5 minutes at room temperature. The reaction mixture is added to a solution of bromochloromethane (15 ml) in dimethylformamide (15 ml) at −30° C., and the mixture is stirred at −20° C. to −30° C. for 30 minutes. The reaction mixture is diluted with water and extracted with ethyl acetate. The extract is washed with brine, dried over sodium sulfate, and concentrated. To a solution of the residue in acetone (30 ml) is added potassium thioacetate (1.92 g: 16.8 mMol.), and the mixture is stirred at room temperature for 1 hour. The reaction mixture is diluted with water and extracted with ethyl acetate. The extract is washed with water, dried over sodium sulfate, and concentrated. The residue is purified by silica chromatography (toluene: ethyl acetate=10:1) and crystallized from ether to give 4-acetylthiomethylthiomethyl-1-trityl-1,2,3-triazole (2.65 g) as colorless crystals. Yield: 71%. mp. 106° C.

NMR δ(CDCl₃) ppm: 2.32(s, 3H), 3.89(s, 2H), 4.04(s, 2H), 7.1–7.2(m, 6H), 7.3–7.4(m, 9H), 7.93(s, 1H). IR ν(CHCl₃) cm⁻¹: 1690, 1491, 1440.

6. 3-substitution with acylate: To a solution of 4-acetylthiomethylthiomethyl-1-trityl-1,2,3-triazole (756 mg: 1.70 mMol.) in a mixture of dimethylformamide (8 ml) and tetrahydrofuran (4 ml) cooling at −78° C. is added a 1.28N-solution of sodium methoxide in methanol (1.24 ml: 1.59 mMol.), and the mixture is stirred for 15 minutes at −78° C. To the reaction mixture is added a solution of 7β-[(Z)-2-(2-t-butoxycarbonylaminothiazol-4-yl)-2-trityloxyiminoacetamido]-3-methanesulfonyloxy-3-cephem-4-carboxylic acid diphenylmethyl ester (1.50 g: 1.54 mMol.) in dimethylformamide (5 ml), and the mixture is stirred at −78° C. for 50 minutes. The reaction mixture is mixed with 10% hydrochloric acid (1 ml), diluted with water, and extracted with ethyl acetate. The extract is washed with brine, dried over sodium sulfate, and concentrated. The residue is purified twice by Lobar column chromatography (toluene: ethyl acetate=3:1) and once by silica gel chromatography (toluene: ethyl acetate=10:1–5:1) to give 7β-[(Z)-2-(2-t-butoxycarbonylaminothiazol-4-yl)-2-trityloxyiminoacetamido]-3-(1-trityl-1,2,3-triazol-4-ylmethylthiomethylthio)-3-cephem-4-carboxylic acid diphenylmethyl ester (1.18 g) as color-less foam. Yield: 60%.

NMR δ(CDCl$_3$) ppm: 1.50(s, 9H), 3.35, 3.51(ABq, J=17.0 Hz, 2H), 3.77(s, 4H), 5.04(d, J=4.6 Hz, 1H), 5.89(dd, j=4.6 Hz, J=8.4 Hz, 1H), 6.89(s, 1H), 7.02(s, 1H), 7.05–7.60(m, 42H), 8.65(brs, 1H). IR ν(CHCl$_3$) cm$^{-1}$: 3400, 1784, 1717, 1686, 1542, 1492, 1445, 1369.

7.deprotection : To a solution of 7β-[(Z)-2-(2-t-butoxycarbonylaminothiazol-4-yl)-2-trityloxyiminoacetamido]-3-(1-trityl-1,2,3-triazol-4-ylmethylthiomethylthio)-3-cephem-4-carboxylic acid diphenylmethyl ester (1.13 g: 0.884 mMol.) in a mixture of anisole (3 ml) and nitromethane (12 ml) at −40° C. is added a solution of aluminum chloride (0.94 g: 7.07 mMol.) in anisole (3 ml), and the mixture is stirred at −30° to −40° C. for 1 hour. The reaction mixture is mixed with 1N-hydrochloric acid (7.5 ml) and diluted with water. The aqueous solution is washed with ethyl acetate. The aqueous layer is concentrated under reduced pressure to remove the remaining organic solvents, subjected to chromatography over styrene-divinylbenzene copolymer column (methanol : water=4:1). The resulting powder is washed with ethyl acetate to give 7β-[(Z)-2-(2-aminothiazol-4-yl)-2-hydroxyiminoacetamido]-3-(1,2,3-triazol-4-ylmethylthiomethylthio)-3-cephem-4-carboxylic acid (318 mg) as pale yellow white powder. Yield: 68%.

NMR δ(D$_2$O-NaHCO$_3$) ppm: 3.53, 3.79(ABq, J=17.4 Hz, 2H), 3.77, 3.87 (ABq, J=13.8 Hz, 2H), 4.00, 4.03(ABq, J=14.8 Hz, 2H), 5.26(d, J=4.6 Hz, 1H), 5.83(d, J=4.6 Hz, 1H), 6.99(s, 1H), 7.88(s, 1H). IR ν(KBr) cm$^{-1}$: 3100br, 1760, 1655, 1600, 1525, 1385, 1345.

This compound is a potent antibacterial against *Morgania morganii* SR9 (0.1 μg/ml) and *Enterobacter cloacae* SR233 (0.8 μg/ml) and shows a high blood level on oral administration (12.1 μg/ml: 15 minutes, mice).

2) R$^1$=methylmethylene (4P8) (4E9)

1. To a solution of 1,2,3-triazol-4-ylthiol sodium salt (2.00 g: 16.3 mMol.) in dimethylformamide (8 ml) at −30° C. is added 1-chloroethyl thiolacerate (2.40 g: 94% : 16.3 mMol.) in dimethylformamide (3 ml), and the mixture is stirred at room temperature for 1 hour. The reaction mixture is diluted with water and extracted with ethyl acetate. The extract is washed with brine, dried over sodium sulfate, and concentrated. The residue is purified by silica gel chromatography (toluene: ethyl acetate=2:1) to give 4-(1-acetylthioethylthio)-1,2,3-triazole (2.90 g) as colorless oil. Yield: 88%.

NMR δ(CDCl$_3$) ppm: 1.67(d, J=7.0 Hz, 3H), 2.30(s, 3H), 4.93(q, J=7.0 Hz, 1H), 7.85(s, 1H), 9.5–10.5(brs, 1H). IR ν(CHCl3) cm−1: 3440, 3160br, 1692, 1487, 1445, 1378, 1358.

2. To a solution of 1ξ-(1,2,3-triazol-4-ylthio)ethyl thiolacerate (127 mg: 0.626 mMol.) in dimethylformamide(4 ml) at −70° C. is added a solution of lithium methoxide in methanol (1.8N: 0.67 ml: 1.21 mMol.), and the mixture is stirred for 1 hour at −55° to −60° C. To this solution at −78° C. is added a solution of 7β-phenylacetylamino-3-trifluoromethanesulfonyloxy-3-cephem-4-carboxylic acid diphenylmethyl ester (316 mg: 0.5 mMol.) in dimethylformamide (3 ml), and the mixture is stirred at −78° C. for 10 minutes. The reaction mixture is mixed with 10% hydrochloric acid (1 ml), diluted with water, and extracted with ethyl acetate. The extract is washed with brine, dried over sodium sulfate, and concentrated. The residue is purified by silica gel chromatography (toluene: ethyl acetate=1:1) to give a mixture of 7β-phenylacetylamino-3-[ξ-(1,2,3-triazol-4-ylthio)ethyl]thio-3-cephem-4-carboxylic acid diphenylmethyl ester and its 2-cephem isomer (100 mg). By repeating chromatography, 7β-phenylacetylamino-3-[1ξ-(1,2,3-triazol-4-ylthio)ethyl]thio-3-cephem-4-carboxylic acid diphenylmethyl ester can be isolated.

NMR δ(CDCl$_3$) ppm: 1.47(d, J=6.8 Hz, 3H), 3.55, 3.80(ABq, J=17.2 Hz, 2H), 3.63(s, 2H), 4.55(q, J=6.8 Hz, 1H), 4.96(d, J=4.8 Hz, 1H), 5.78(dd, J=4.8 Hz, J=8.8 Hz, 1H), 6.95(s, 1H), 7.1–7.4(m, 16H), 7.50(s, 1H).

3) 7α-methoxy (4P11) (4E8)

1. To a solution of 7β-amino-3-(trityl-1,2,3-triazol-4-ylthiomethylthio)-3-cephem-4-carboxylic acid diphenylmethyl ester (8.02 g: 10.7 mMol.) in benzene (200 ml) is added 3,5-di-t-butyl-4-hydroxybenzaldehyde (3.00 g: 12.8 mMol.), and the mixture is heated for 1.5 hours under azeotropic distillation, and the mixture is concentrated. To a solution of the residue in a mixture of benzene (100 ml) and dichloromethane (70 ml) at −30° C. are added magnesium sulfate (5.3 g) and nickel peroxide (10.7 g), and the mixture is stirred at room temperature for 1 hour. The reaction mixture is filtered to remove solid material. To the filtrate at −40° C. is added methanol (180 ml) dried over 4A molecular sieves, and the mixture is stirred at room temperature for 1 hour and the reaction mixture is concentrated. The residue is purified by silica gel chromatography (toluene: ethyl acetate=20:1) to give 7β-(3,5-di-t-butyl-4-hydroxybenzylidene)amino-7α-methoxy-3-(trityl-1,2,3-triazol-4-ylthiomethylthio)-3-cephem-4-carboxylic acid diphenylmethyl ester (8.58 g) as yellow foam. Yield: 80%.

NMR δ(CDCl$_3$) ppm: 1.46(s, 18H), 3.57(s, 3H), 3.52, 3.70(ABq, J=16.9 Hz, 2H), 4.09, 4.11(ABq, J=13.8 Hz, 2H), 5.07(s, 1H), 5.63(s, 1H), 6.91(s, 1H), 7.05–7.5(m, 25H), 7.48(s, 1H), 7.69(s, 2H), 8.55(s, 1H). IR ν(CHCl$_3$) cm$^{-1}$: 3630, 1770, 1631, 1600, 1585, 1497, 1447, 1429, 1377.

2.To a solution of 7β-(3,5-di-t-butyl-4-hydroxybenzylidene) amino-7α-methoxy-3-(trityl-1,2,3-triazol-4-ylthiomethylthio)-3-cephem-4-carboxylic acid diphenylmethyl ester (8.39 g: 8.40 mMol.) in a mixture of tetrahydrofuran (40 ml) and methanol (160 ml) are added Girard T reagent (2.11 g: 12.6 mMol.), water (0.1 ml), and acetic acid (0.1 ml), and the mixture is stirred at room temperature for 2 hours. The reaction mixture is concentrated, diluted with ice-water, and extracted with ethyl acetate. The extract is washed with brine, dried over sodium sulfate, and concentrated. The residue is purified by silica gel chromatography (toluene: ethyl acetate=10:1 to 3:1) to give 7β-amino-7α-methoxy-3-(trityl-1,2,3-triazol-4-ylthiomethylthio)-3-cephem-4-carboxylic acid diphenylmethyl ester (5.10 g) as pale yellow foam. Yield: 78%.

NMR δ(CDCl₃) ppm: 3.50(s, 3H), 3.48, 3.66(ABq, J=15.8 Hz, 2H), 4.15(s, 2H), 4.85(s, 1H), 6.89(s, 1H), 7.05-7.5(m, 25H), 7.50(s, 1H). IR ν(CHCl₃) cm⁻¹: 1777, 1705, 1602, 1495, 1446, 1378.

3. To a solution of 7β-amino-7α-methoxy-3-(trityl-1,2,3-triazol-4-ylthiomethylthio)-3-cephem-4-carboxylic acid diphenylmethyl ester (1.50 g: 1.92 mMol.) in dichloromethane (10 ml) at −40° C. are added N-methylmorpholine (0.48 ml: 4.37 mMol.), difluoromethylthioacetic acid (299 mg: 2.11 mMol.), and then phenyl dichlorophosphate (0.34 ml: 2.27 mMol.), and the mixture is stirred at −30° to −40° C. for 1 hour. The reaction mixture is mixed with 10% hydrochloric acid (2 ml), diluted with water, and extracted with ethyl acetate. The extract is washed with dilute hydrochloric acid, aqueous 5% sodium hydrogen carbonate, and brine, dried over sodium sulfate, and-concentrated. The residue is purified by silica gel chromatography (toluene: ethyl acetate=3:1) to give 7β-difluoromethylthioacetylamino-7α-methoxy-3-(trityl-1,2,3-triazol-4-ylthiomethylthio)-3-cephem-4-carboxylic acid diphenylmethyl ester (1.55 g) as pale yellow foam. Yield: 89%.

NMR δ(CDCl₃) ppm: 3.47, 3.54(ABq, J=15.0 Hz, 2H), 3.60(s, 5H), 4.05, 4.13(ABq, J=13.6 Hz, 2H), 4.98(s, 1H), 6.84(s, 1H), 6.94(t, J=55.8 Hz, 1H), 7.05-7.4(m, 26H), 7.49(s, 1H). IR ν(CHCl₃) cm⁻¹: 3380, 1778, 1696, 1600, 1495, 1447, 1382.

4. To a solution of 7β-difluoromethylthioacetylamino-7α-methoxy-3-(trityl-1,2,3-triazol-4-ylthiomethylthio)-3-cephem-4-carboxylic acid diphenylmethyl ester (1.51g: 1.66 mMol.) in a mixture of anisole (2.4 ml) and dichloromethane (6 ml) under ice cooling is added trifluoro-acetic acid (6 ml), and the mixture is stirred under ice cooling for 50 minutes and at room temperature for 20 minutes. The reaction mixture is cooled with ice, mixed with water (2 ml) and ethyl acetate, washed with water, dried over sodium sulfate, and concentrated. The residue is dissolved in ethyl acetate and extracted with aqueous 5% sodium hydrogen carbonate. The aqueous extract is adjusted to pH 2.0 to 3.0 with 10% hydrochloric acid and extracted with ethyl acetate. The extract is dried over sodium sulfate and concentrated. The residue is pulverized with a mixture of ether and hexane to give 7β-difluoromethylthioacetylamino-7α-methoxy-3-(1,2,3-triazol-4-ylthiomethylthio-3-cephem-4-carboxylic acid (195 mg) as pale yellow foam. Yield: 24%.

NMR δ(D₂O-NaHCO₃) ppm: 3.55(s, 3H), 3.36, 3.65(ABq, J=17. Hz, 2H), 3.74(s, 2H), 4.11, 4.19(ABq, J=13.8 Hz, 2H), 5.15(s, 1H), 7.11(t, J=55.4 Hz, 1H), 7.98(s, 1H). IR ν(KBr) cm⁻¹: 3240br, 1770, 1680, 1520, 1365.

Example 7 deprotection

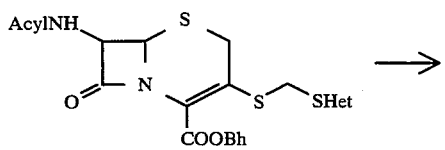
COOBh

-continued

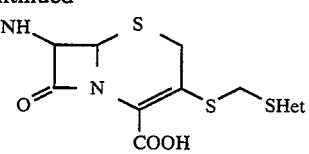
COOH

1) Acyl=difluoromethylthioacetyl Het=1,2,3-triazol-4-yl (4E7-5)

To a solution of 7β-difluoromethylthioacetamido-3-(1,2,3-triazol-4-ylthiomethylthio)-3-cephem-4-carboxylic acid diphenylmethyl ester (451 mg: 0.710 mMol.) in a mixture of dichloromethane (3 ml) and anisole (1.2 ml) under ice cooling is added trifluoroacetic acid (3 ml), and the mixture is stirred under ice cooling for 1 hour. The reaction mixture is concentrated to dryness and the residue is pulverized with ether, washed, and dried to give 7β-difluoromethylthioacetamido-3-(1,2,3- triazol-4-ylthiomethylthio)-3-cephem-4-carboxylic acid (257 mg) white powder. Yield: 77%.

NMR δ(D₂O-NaHCO₃) ppm: 3.47, 3.67(ABq, J=17.4 Hz, 2H), 3.68(s, 2H), 4.12, 4.24(ABq, J=13.4 Hz, 2H), 5.11(d, J=4.6 Hz, 1H), 5.66(d, J=4.6 Hz, 1H), 7.09(t, JHF=55.4 Hz, 1H), 8.01(s, 1H). IR ν(KBr) cm⁻¹: 3400br, 3260, 1765, 1662, 1545, 1360, 1333.

This compound is a potent antibacterial against Staphylococcus aureus Smith (0.1 μg/ml) and shows a high blood level on oral administration (28 μg/ml: 15 minutes, mice).

2) Acyl=phenylacetyl Het=1,2,3-triazol-4-yl (3E3-1)

To a suspension of 7β-phenylacetylamino-3-(1,2,3-triazol-4-yl)thiomethylthio-3-cephem-4-carboxylic acid diphenylmethyl ester (186 mg: 0.296 mMol.) in dichloromethane (3 ml) under ice cooling is added anisole (0.45 ml) and trifluoroacetic acid (0.45 ml), and the mixture is stirred for 1 hour 40 minutes. The reaction mixture is concentrated, triturated with hexane, and washed with ethyl acetate to give 7β-phenylacetylamino-3-(1,2,3-triazol-4-yl)thiomethylthio-3-cephem-4-carboxylic acid as white solid (67 mg). Yield: 49%.

NMR δ(D₂O-NaHCO₃) ppm: 3.40, 3.56(ABq, J=17 Hz, 2H), 3.66, 3.70(ABq, J=15 Hz, 2H), 4.07, 4.20(ABq, J=14 Hz, 2H), 5.03(d, J=5 Hz, 1H), 5.61(d, J=5 Hz, 1H), 7.3-7.5(m, 5H), 7.90(s, 1H). IR ν(KBr) cm⁻¹: 3440, 1775, 1705, 1660, 1540, 1353, 1238.

This compound shows a strong antibacterial activity against Staphylococcus aureus Smith (0.05 μg/ml) and 209P JC-1 (0.05 μg/ml) and shows a high blood level on oral administration (15 μg/ml: 15 minutes, mice).

3) Acyl=D-mandeloyl Het=(trityl to H)-1,2,3-triazol-4-yl (4E7-3)

To a solution of 7β-D-mandelamido-3-(trityl-1,2,3-triazol-4-ylthiomethylthio)-3-cephem-4-carboxylic acid diphenylmethyl ester (445 mg: 0.502 mMol.) in a mixture of anisole (0.8 ml) and dichloromethane (2 ml) under ice cooling is added trifluoroacetic acid (2 ml), and the mixture is stirred under ice cooling for 30 minutes and at room temperature for 20 minutes. The reaction mixture is diluted with methanol (10 ml) and concentrated. The residue is dissolved in dilute aqueous sodium hydrogen carbonate water, washed with ethyl acetate, acidified with 10% hydrochloric acid, and extracted with ethyl acetate. The extract is dried over sodium sulfate and concentrated. The residue is pulverized with ether to give 7β-D-mandelamido-3-(1,2,3- triazol-4-ylthiomethylthio)-3-cephem-4-carboxylic acid (59.2 mg) as yellowish white powder. Yield: 25%.

NMR δ(D₂O-NaHCO₃) ppm: 3.39, 3.62(ABq, J=17.4 Hz, 2H), 4.10, 4.21 (ABq, J=13.8 Hz, 2H), 5.07(d, J=4.8 Hz, 1H), 5.27(s, 1H), 5.62(d, J=4.8 Hz, 1H), 7.46(s, 5H), 8.02(s, 1H). IR ν(KBr) cm⁻¹: 3360br, 1770, 1673, 1520, 1452, 1365.

This compound shows a high blood level on oral administration (18.5 μg/ml: 15 minutes, mice).

4) Acyl=(Z)-2-[2-(t-butoxycarbonylamino to amino)-thiazol-4-yl]-2-pentenoyl Het=1,2,3-triazol-4-yl (4E7-6)

To a solution of 7β-[(Z)-2-(2-t-butoxycarbonylaminothiazol-4-yl)-2-pentenoylamino]-3-(1,2,3-triazol-4-ylthiomethylthio)-3-cephem-4-carboxylic acid diphenylmethyl ester (537 mg: 0.68 mMol.) in a mixture of anisole (2 ml) and nitromethane (8 ml) at −30° C. is added a solution of aluminum chloride (0.54 g: 4 mMol.) in anisole (2 ml), and the mixture is stirred for 1 hour. The reaction mixture is diluted with ethanol (3 ml), stirred for 5 minutes, mixed with 1N-hydrochloric acid (8 ml) and water (200 ml), washed with ethyl acetate, and concentrated under reduced pressure to remove remaining organic solvents. The resulting aqueous solution is subjected to chromatography over styrene-divinylbenzene copolymer (methanol: water=4:1) to give 7β-[(Z)-2-(2-aminothiazol-4-yl)-2-pentenoylamino]-3-(1,2,3-triazol-4-ylthiomethylthio)-3-cephem-4-carboxylic acid (156 mg) as white solid. Yield: 44%.

NMR δ(D₂-NaHCO₃) ppm: 1.07(t, J=7.8 Hz, 3H), 2.24(quin, J=7.8 Hz, 2H), 3.50, 3.72(ABq, J=17 Hz, 2H), 4.12, 4.24(ABq, J=14 Hz, 2H), 5.19(d, J=4.8 Hz, 1H), 5.79(d, J=4.8 Hz, 1H), 6.37(t, J=8 Hz, 1H), 6.50(s, 1H), 8.03(s, 1H). IR ν(KBr) cm⁻¹: 3400br, 1763, 1655, 1530, 1388, 1348.

5) Acyl=(Z)-2-(2-t-butoxycarbonylaminothiazol-4-yl)-2-trityloxyiminoacetyl Het=1,2,3-triazol-4-yl (1E08)

To a suspension of 7β-[(Z)-2-(2-t-butoxycarbonylaminothiazol-4-yl)-2-trityloxyiminoacetamido]-3-(1,2,3-triazol-4-yl) thiomethylthio-3-cephem-4-carboxylic acid diphenylmethyl ester (9.2 g: 9 mMol.) in a mixture of anisole (18 ml) and nitromethane (72 ml) is added dropwise a solution of aluminum chloride (9.6 g: 72 mMol.) in anisole (31 ml) at −30° C. After stirring for 1 hour at the same temperature, the reaction mixture is quenched with ethanol (25 ml), stirred for several minutes, diluted with 1N-hydrochloric acid (75 ml) and water (500 ml), and washed with ethyl acetate. The aqueous layer was separated, concentrated to remove the organic solvents, and passed through a column of styrene-divinylbenzene copolymer adsorbent. The product is eluted with a mixture of methanol and water (4:1) to give 7β-[(Z)-2-(2-aminothiazol-4-yl)-2-hydroxyiminoacetamido]-3-(1,2,3-triazol-4-yl)thiomethylthio-3-cephem-4-carboxylic acid as pale yellow powder (4.19 g). Yield: 90%.

NMR δ(D₂O-NaHCO₃) ppm: 3.57, 3.75(ABq, J=17.2 Hz, 2H), 4.14, 4.25(ABq, J=13.9 Hz, 2H), 5.21(d, J=4.7 Hz, 1H), 5.84(d, J=4.7 Hz, 1H), 6.99(s, 1H), 8.07(s, 1H). IR ν(KBr) cm⁻¹: 3280, 3100, 1760, 1660, 1590, 1555, 1385, 1345, 1175, 995.

This compound is a potent antibacterial against Escherichia colt 7437 (0.02 μg/ml) and *Enterobacter cloacae* SR233 (0.8 μg/ml) and shows a high blood level on oral administration (29.6 μg/ml: 15 minutes, mice).

6) Acyl=(Z)-2-[2-(t-butoxycarbonylamino to amino)-thiazol-4-yl]-2-methoxyiminoacetyl Het=1-(trityl to H)-1,2,3-triazol-4-yl (3E3-5)

To a solution of 7β-[(Z)-2-(2-t-butoxycarbonylaminothiazol-4-yl)-2-methoxyiminoacetyl]amino-3-(1-trityl-1,2,3-triazol-4-yl)thiomethylthio-3-cephem-4-carboxylic acid diphenylmethyl ester (570 mg: 0.55 mMol.) in a mixture of anisole (1.7 ml) and nitromethane (5 ml) at −30° C. is added e solution of aluminum chloride (0.51 g: 3.83 mMol.) in anisole (1.8 ml), and the mixture is stirred for 30 minutes. The reaction mixture is mixed with 1N-hydrochloric acid (4 ml) and ethyl acetate (10 ml), stirred at room temperature for 5 minutes, poured into a solution of sodium hydrogen carbonate (3.2 g) in water (100 ml), and stirred for several minutes. After filtering off the insoluble material, the reaction mixture is washed with ethyl acetate, concentrated in vacuum to remove the organic solvents. The resulting aqueous layer is purified by stylene-divinylbenzene copolymer chromatography (water: methanol=10:1) to give 7β-[(Z)-2-(2-aminothiazol-4-yl)-2-methoxyiminoacetyl]amino-3-(1,2,3-triazol-4-yl)thiomethylthio-3-cephem-4-carboxylic acid sodium salt as white foam ( 194 mg). Yield: 64%.

NMR δ(D₂O) ppm: 3.48, 3.67(ABq, J=17 Hz, 2H), 3.99(s, 3H), 4.11, 4.23 (ABq, J=14 Hz, 2H), 5.17(d, J=5 Hz, 1H), 5.80(d, J=5 Hz, 1H), 7.02 (s, 1H), 7.97(s, 1H). IR ν(KBr) cm⁻¹: 3400, 1753, 1660, 1605, 1390, 1040.

This compound shows a strong antibacterial activity against Proteus vulgaris CN329 (0.02 μg/ml) and *Morgania morganii* SR9 (0.1 μg/ml) and a high blood level (15 μg/ml: mouse 15 minutes) on oral administration. 7) Acyl=(Z)-2-[2-t-butoxycarbonylamino to amino)-thiazol-4-yl]-2-cyclopentyloxyiminoacetyl Het=1,2,3-triazol-4-yl (4E7-11)

To a suspension of 7β-[(Z)-2-(2-t-butoxycarbonylaminothiazol-4-yl)-2-cyclopentyloxyiminoacetamido]-3-(1,2,3-triazol-4-ylthiomethylthio)-3-cephem-4-carboxylic acid diphenylmethyl ester (258 mg: 0.304 mMol.) in a mixture of anisole (1 ml) and nitromethane (4 ml) at −30° C. is added a solution of aluminum chloride (0.25 g: 1.88 mMol.) in anisole (1 ml), and the mixture is stirred for 50 minutes. The reaction mixture is diluted with ethanol (2 ml), stirred at the same temperature for 5 minutes, mixed with 1N-hydrochloric acid (4 ml) and water (200 ml), and stirred at room temperature for 5 minutes. The aqueous layer is taken, washed with ethyl acetate, concentrated under reduced pressure to remove remaining organic solvents, and subjected to chromatography over styrene-divinylbenzene copolymer (methanol : water=4:1) to give 7β-[(Z)-2-(2-aminothiazol-4-yl)-2-cyclopentyloxyiminoacetamido]-3-(1,2,3-triazol-4-ylthiomethylthio)-3-cephem-4-carboxylic acid (93 mg) as white solid. Yield: 53%.

NMR δ(D₂O-NaHCO₃) ppm: 1.4–2.0(m, 8H), 3.50, 3.70(ABq, J=17 Hz, 2H), 4.13, 4.23(ABq, J=14 Hz, 2H), 5.17(d, J=4.8 Hz, 1H), 5.77 (d, J=4.8 Hz, 1H), 6.98(s, 1H), 8.03(s, 1H). IR ν(KBr) cm⁻¹: 3300br, 1765, 1665, 1526, 1385, 1343.

This compound is a potent antibacterial against *Escherichia coli* EC-14 (0.8 μg/ml) and *Pseudomonas aeruginosa* A25619 (0.8 μg/ml).

8) Acyl=(Z)-2-[2-(t-butoxycarbonylamino to amino) thiazol-4-yl]-2-(2-propenyloxyimino)acetyl Het=1,2,3-triazol-4-yl (4E7-10)

To a solution of 7β-[(Z)-2-(2-t-butoxycarbonylaminothiazol-4-yl)-2-(2-propenyloxyimino)acetamido]-3-(1,2,3-triazol-4-ylthiomethylthio)-3-cephem-4-carboxylic acid diphenylmethyl ester (376 mg: 0.46 mMol.) in a mixture of anisole (1.5 ml) and nitromethane (6 ml) at −30° C. is added a solution of aluminum chloride (0.37 g: 2.8 mMol.) in anisole (1.5 ml), and the mixture is stirred for 50 minutes. The reaction mixture is mixed with ethanol (2 ml) and stirred at the same temperature for 5 minutes and mixed with 1N-hydrochloric acid (5 ml) and water (200 ml). The aqueous layer is taken, washed with ethyl acetate, and concentrated under reduced pressure to remove remaining organic solvents. The resulting aqueous layer is subjected to chromatography over styrene- divinylbenzene copolymer (methanol: water=4:1). The eluting material is washed with ethyl acetate to give 7β-[(Z)-2-(2-aminothiazol-4-yl)-2-(2-propenyloxyimino)acetamido]-3-(1,2,3-triazol-4-ylthiomethylthio)-3-cephem-4-carboxylic acid (127 mg) as white solid. Yield: 50%.

NMR δ(D₂O-NaHCO₃) ppm: 3.48, 3.67(ABq, J=17 Hz, 2H), 4.11, 4.24(ABq, J=14 Hz, 2H), 4.72(d, J=5.6 Hz, 2H), 5.18(d, J=4.6 Hz, 1H), 5.30(dd, J=1.6 Hz, J=10.6 Hz, 1H), 5.37(dd, J=1.6 Hz, J=17.4 Hz, 1H), 5.82(d, J=4.6 Hz, 1H), 6.07(ddt, J=5.6 Hz, J=10.6 Hz, J=17.4 Hz, 1H), 7.03(s, 1H), 7.99(s, 1H). IR ν(KBr) cm⁻¹: 3450, 3270, 1753, 1653, 1618, 1545, 1532, 1384, 1357, 1021, 1000.

This compound is a potent antibacterial against *Escherichia coli* EC-14 (0.4 μg/ml) and *Enterobacter cloacae* SR233 (0.8 μg/ml).

9) Acyl=N-(t-butoxycarbonyl to H)-2-phenylglycyl Het=(trityl to H)-1,2,3-triazol-4-yl (4E7-2)

To a solution of 7β-(N-t-butoxycarbonyl-2-phenylglycylamino)-3-(trityl-1,2,3-triazol-4-ylthiomethylthio)-3-cephem-4-carboxylic acid diphenylmethyl ester (480 mg: 0.487 mMol.) in a mixture of anisole (1.2 ml) and dichloromethane (3 ml) under ice cooling is added trifluoro- acetic acid (3 ml), and the mixture is stirred under ice cooling for 30 minutes and at room temperature for 50 minutes. The reaction mixture is shaken with ice water and ethyl acetate under ice cooling. The aqueous layer is taken, concentrated to remove the remaining organic solvents under reduced pressure, and subjected to column chromatography over styrene-divinylbenzene copolymer resin (methanol: water=4:1). The residue is pulverized from ethyl acetate to give 7β-(2-phenylglycylamino)-3-(1,2,3-triazol-4-ylthiomethylthio)-3-cephem-4-carboxylic acid (157 mg) as white powder. Yield: 67%.

NMR δ(D₂O) ppm: 3.46, 3.67(ABq, J=17.1 Hz, 2H), 4.25, 4.31(ABq, J=14.2 Hz, 2H), 5.13(d, J=4.4 Hz, 1H), 5.27(s, 1H), 5.66(d, J=4.4 Hz, 1H), 7.54(s, 5H), 8.07(s, 1H). IR ν(KBr) cm⁻¹: 3400, 3060br, 1763, 1690, 1595, 1458, 1388, 1345.

10) Acyl=2-[2-(t-butoxycarbonylamino to amino) thiazol-4yl]acetyl Het=(trityl to H)-1,2,3-triazol-4-yl (4E7-1)

To a solution of 7β-[2-(2-t-butoxycarbonylaminothiazol-4-yl)acetamido]-3-(trityl-1,2,3-triazol-4-ylthiomethylthio)-3-cephem-4-carboxylic acid diphenylmethyl ester (779 mg: 0.784 mMol.) in a mixture of anisole (3 ml) and nitromethane (12 ml) at −40° C. is added a solution of aluminum chloride (0.83 g: 6.24 mMol.) in anisole (3 ml), and the mixture is stirred at −30° to −40° C. for 50 minutes. The reaction mixture is mixed with 1N-hydrochloric acid (6.3 ml), diluted with water, washed with ethyl acetate, and concentrated under reduced pressure to remove the remaining organic solvents. The residual solution is subjected to the chromatography over styrene-divinylbenzene copolymer (methanol: water=4:1) and resulting powder is washed with ethyl acetate to give 7β-[2-(2-aminothiazol-4-yl)acetamido]-3-(1,2,3-triazol-4-ylthiomethylthio)-3-cephem-4-carboxylic acid (225 mg) as white powder. Yield: 59%.

NMR δ(D₂O-CD₃OD-NaHCO₃) ppm: 3.57(s, 2H), 3.43, 3.60(ABq, J=17.4 Hz, 2H), 4.08 4.20(ABq, J=13.8 Hz, 2H), 5.06(d, J=4.7 Hz, 1H), 5.65(d, J=4.7 Hz, 1H), 6.49(s, 1H), 7.92(s, 1H). IR (KBr) cm⁻¹: 3510, 3260br, 1759, 1664, 1579, 1551, 1401, 1352, 1326.

This compound is a potent antibacterial against Staphylococcus aureus Smith (0.1 μg/ml), *Escherichia coli* EC-14 (0.8 μg/ml), and Proteus vulgaris CN-329 (0.8 μg/ml) and shows a high blood level on oral administration (17.1 μg/ml: 15 minutes, mice).

11) Acyl=2-[2-(t-butoxycarbonylamino to amino)-thiazol-4-yl]glyoxylyl Het=(trityl to H)-1,2,3-triazol-4-yl (4E7-4)

To a solution of 7β-[2-(2-t-butoxycarbonylaminothiazol-4-yl)glyoxylylamino]-3-(trityl-1,2,3-triazol-4-ylthiomethylthio)-3-cephem-4-carboxylic acid diphenylmethyl ester (649 mg: 0.644 mMol.) in a mixture of anisole (2.5 ml) and nitromethane (10 ml) at −40° C. is added a solution of aluminum chloride (0.69 g: 5.19 mMol.) in anisole (2.5 ml), and the mixture is stirred at −30° to −40° C. for 50 minutes. The reaction mixture is mixed with 1N-hydrochloric acid (5.2 ml), diluted with water, washed with ethyl acetate, and concentrated under reduced pressure to remove remaining organic solvents. The remaining aqueous solution is subjected to chromatography on analytical styrene-divinylbenzene copolymer column (methanol: water=3:2). The resulting powder is washed with ethyl acetate to give 7β-[2-(2-aminothiazol-4-yl)glyoxylylamido]-3-(1,2,3-triazol-4-ylthiomethylthio)-3-cephem-4-carboxylic acid (130 mg) as yellow powder. Yield: 40%.

NMR δ(CD₃SOCD₃) ppm: 3.83(s, 2H), 4.44(s, 2H), 5.19(d, J=4.6 Hz, 1H), 5.68(dd, J=8.2 Hz, J=4.6 Hz, 1H), 7.40(s, 2H), 7.87(s, 1H), 7.9–8.1(brs, 1H), 9.81(d, J=8.2 Hz, 1H). IR ν(KBr) cm⁻¹: 3300br, 3120, 1764, 1660, 1620, 1519, 1480, 1355.

This compound is a potent antibacterial against *Escherichia coli* EC-14 (0.4 μg/ml).

12) Acyl=(Z)-2-[2-(t-butoxycarbonylamino to amino)-thiazol-4-yl]-2-(trityl to H)oxyiminoacetyl Het=(trityl to H)-1,2,3-triazol-4-yl (1E09)

To a solution of 7β-[(Z)-2-(2-t-butoxycarbonylaminothiazol-4-yl)-2-trityloxyiminoacetamido]-3-(1-trityl-1,2,3-triazol-4-yl)thiomethylthio-3-cephem-4-carboxylic acid diphenylmethyl ester (29 g: 22.9 mMol.) in a mixture of anisole (50 ml) and nitromethane (200 ml) is added dropwise a solution of aluminum chloride (20.7 g: 156 mMol.) in anisole (50 ml) at −30° to −40° C., and the mixture is stirred for 1 hour at the same temperature. The reaction mixture is diluted with 1N-hydrochloric acid (200 ml) and water, and washed with ethyl acetate. The aqueous layer is concentrated to remove organic solvent under reduced pressure and passed through a column of styrene-divinylbenzene copolymer adsorbent. The product is eluted with aqueous methanol (4:1) to give 7β-[(Z)-2-(2-aminothiazol-4-yl)-2-hydroxyiminoacetamido]-3-(1,2,3-triazol-4-yl)thiomethylthio-3-cephem-4-carboxylic acid (8.07 g) as pale yellow powder. Yield: 68%.

NMR δ(D₂O-NaHCO₃) ppm: 3.51, 3.75(ABq, J=17.2 Hz, 2H), 4.14, 4.25 (ABq, J=13.9 Hz, 2H), 5.21(d, J=4.7 Hz, 1H), 5.84(d, J=4.7 Hz, 1H), 6.99(s, 1H), 8.07(s, 1H). IR ν(KBr) cm⁻¹: 3280, 3100, 1760, 1660, 1590, 1525, 1385, 1345, 1175, 995.

This compound is a potent antibacterial against *Escherichia coli* 7437 (0.02 μg/ml) and *Enterobacter cloacae* SR233 (0.8 μg/ml) and shows a high blood level on oral administration (29.6 μg/ml: 15 minutes, mice).

13) (isolated as disodium salt) Acyl=(Z)-2-[2-(tritylamino to amino)-thiazol-4-yl]-2-(diphenylmethoxycarbonyl to carboxy) methoxyiminoacetyl Het=(trityl to H)-1,2,3-triazol-4-yl (4E7-12)

A solution of 7β-[(Z)-2-(2-tritylaminothiazol-4-yl)-2-(diphenylmethoxycarbonylmethoxyimino)acetamido]-3-(trityl-1,2,3-triazol-4-ylthio-methylthio)-3-cephem-4-carboxylic acid diphenylmethyl ester (1.04 g: 0.749 mMol.) in a mixture of 98% formic acid (16 ml) and water (0.8 ml) is stirred at room temperature for 3 hours. The reaction mixture is concentrated. The residue is washed with ether, filtered, end dried. To a solution of this residue in a mixture of anisole (2 ml) and nitro- methane (8 ml) at −40° C. is added a solution of aluminum chloride (0.50 g: 3.76 mMol.) in anisole (2 ml), and the mixture is stirred at −30° to −40° C. for 1 hour. The reaction mixture is diluted with 1N-hydrochloric acid (3.8 ml) and water, washed with ethyl acetate, and concentrated under reduced pressure to remove organic solvents. The remaining aqueous solution is subjected to chromatography over styrene-divinylbenzene copolymer (methanol: water=4:1). The residue is washed with ethyl acetate and resulting powder is dissolved in dilute aqueous sodium hydrogen carbonate, and purified by chromatography over analytical styrene-divinylbenzene (water). The eluate is lyophilized and pulverized with ethyl acetate to give 7β-[(Z)-2-(2-aminothiazol-4-yl)-2-(sodiooxycarbonylmethoxyimino)acetamido]-3-(1,2,3-triazol-4-ylthiomethylthio)-3-cephem-4-carboxylic acid sodium salt (121 mg) as pale yellow white powder. Yield: 26%.

NMR δ(D$_2$O) ppm: 3.49, 3.70(ABq, J=17.4 Hz, 2H), 4.12, 4.24(ABq, J=13.8 Hz, 2H), 4.57(s, 2H), 5.18(d, J=4.8 Hz, 1H), 5.82(d, J=4.8 Hz, 1H), 7.04 (s, 1H), 8.02(s, 1H). IR ν(KBr) cm$^{-1}$: 3600–2400br, 1760, 1655, 1595, 1530, 1390, 1350, 1320.

This compound is a potent antibacterial against *Proteus mirabilis* PR-4 (0.006 μg/ml) and *Proteus vulgaris* CN-329 (0.006 μg/ml).

14) (isolated as disodium salt) Acyl=(Z)-2-[2-(trityl amino to amino) thiazol-4-yl]-2-[(S)-1-(diphenylmethoxycarbonyl to carboxy)ethoxyimino]acetyl Het=(trityl to H)-1,2,3-triazol-4-yl (4E7-13)

A solution of 7β-{(Z)-2-(2-tritylaminothiazol-4-yl)-2-[(S)-1-diphenylmethoxycarbonylethoxyimino]acetamido}-3-(trityl-1,2,3-triazol-4-ylthiomethylthio)-3-cephem-4-carboxylic acid diphenylmethyl ester (1.01 g: 0.720 mMol.) in a mixture of 98% formic acid (16 ml) and water (0.8 ml) is stirred at room temperature for 3 hours. The reaction mixture is concentrated and the residue is washed with ether filtered, and dried. The product is dissolved in a mixture of anisole (2 ml) and nitromethane (8 ml), cooled at −40° C., mixed with a solution of aluminum chloride (0.48 g: 3.61 mMol.) in anisole (2 ml), and stirred at −30° to −40° C. for 1.5 hours. The reaction mixture is mixed with 1N-hydrochloric acid (3.6 ml), diluted with water, washed with ethyl acetate, and concentrated under reduced pressure to remove the remaining organic solvents. The resulting aqueous solution is subjected to chromatography over styrene-divinylbenzene copolymer (methanol: water=4:1). The resulting powder is washed with ethyl acetate, dissolved in dilute aqueous sodium hydrogen carbonate, and purified by analytical styrenedivinylbenzene copolymer chromatography (water), and lyophylized. The lyophilizate is washed with ethyl acetate and pulverized to give 7β-{(Z)-2-(2-aminothiazol-4-yl)-2-[(S)-1-sodiooxycarbonylethoxyimino]acetamido}-3-(1,2,3-triazol-4-ylthiomethylthio)-3-cephem-4-carboxylic acid sodium salt (103 mg) as pale yellowish white powder. Yield: 23%.

NMR δ(D$_2$O) ppm: 1.46(d, J=7.0 Hz, 3H), 3.48, 3.67(ABq, J=17.2 Hz, 2H), 4.11, 4.23(ABq, J=13.8 Hz, 2H), 4.65(q, J=7.0 Hz, 1H), 5.18(d, J=4.8 Hz, 1H), 5.84(d, J=4.8 Hz, 1H), 7.02(s, 1H), 7.98(s, 1H). IR ν(KBr) cm$^{-1}$: 3600–2400br, 1760, 1655, 1590, 1528, 1388, 1350.

This compound is a potent antibacterial against *Proteus mirabilis* PR4 (0.01 μg/ml), *Proteus vulgaris* CN-329 (0.006 μg/ml), and *Escherichia coli* EC-14 (0.2 μg/ml).

15) Acyl=(Z)-2-[2-(t-butoxycarbonylamino to amino)-thiazol-4-yl]-2-[1-(diphenylmethoxycarbonyl to carboxy)vinyloxyimino]acetyl Het=(trityl to H)-1,2,3-triazol-4-yl (4E7-15)

To a solution of 7β-[(Z)-2-(2-t-butoxycarbonylaminothiazol-4-yl)-2-(1-diphenylmethoxycarbonylvinyloxyimino)acetamido]-3-(trityl-1,2,3-triazol-4-ylthiomethylthio)-3-cephem-4-carboxylic acid diphenylmethyl ester (910 mg: 0.723 mMol.) in a mixture of anisole (3 ml) and nitromethane (12 ml) at −40° C. is added a solution of aluminum chloride (0.77 g: 5.79 mMol.) in anisole (3 ml), and the mixture is stirred at −30° to −40° C. for 50 minutes. The reaction mixture is mixed with 1N-hydrochloric acid (5.8 ml), diluted with water, washed with ethyl acetate, and concentrated under reduced pressure to remove the remaining organic solvents. The resulting aqueous solution is subjected to chromatography over styrene divinylbenzene copolymer (methanol: water=4:1), and resulting powder is washed with ethyl acetate to give 7β-[(Z)-2-(2-aminothiazol-4-yl)-2-(1-carboxyvinyloxyimino)acetamido]-3-(1,2,3-triazol-4-ylthiomethylthio)-3-cephem-4-carboxylic acid (326 mg) as pale yellow white powder. Yield: 77%.

NMR δ(D$_2$O-NaHCO$_3$) ppm: 3.48, 3.68(ABq, J=17.4 Hz, 2H), 4.11, 4.23(ABq, J=13.9 Hz, 2H), 5.168(d, J=1.7 Hz, 1H), 5.171(d, J=4.8 Hz, 1H), 5.32(d, J=1.7 Hz, 1H), 5.87(d, J=4.8 Hz, 1H), 7.21(s, 1H), 8.00(s, 1H). IR ν(KBr) cm$^{-1}$: 3600–2400br, 1766, 1660, 1630, 1580, 1530, 1390, 1360.

This compound is potent antibacterial against *Proteus mirabilis* PR4 (<0.003 μg/ml) and *Serratia marcescens* SR1005 (0.8 μg/ml).

16) Acyl=(Z)-2-[2-(t-butoxycarbonylamino to amino)-thiazol-4-yl]-2-[(1-t-butoxycarbonyl to carboxy)-1-methylethoxyimino]acetyl Het=(trityl to H)-1,2,3-triazol-4-yl (4E7-14)

To a solution of 7β-[(Z)-2-(2-t-butoxycarbonylaminothiazol-4-yl)-2-(1-t-butoxycarbonyl-1-methylethoxyimino)acetamido]-3-(trityl-1,2,3-triazol-4-ylthiomethylthio)-3-cephem-4-carboxylic acid diphenylmethyl ester (822 mg: 0.706 mMol.) in a mixture of anisole (3 ml) and nitro- methane (12 ml) at −40° C. is added a solution of aluminum chloride (0.75 g: 5.64 mMol.) in anisole (3 ml), and the mixture is stirred at −30° to −40° C. for 1 hour. The reaction mixture is mixed with 1N-hydrochloric acid (5.7 ml), diluted with water, washed with ethyl acetate, and concentrated under reduced pressure to remove remaining organic solvents. The residual solution is subjected to chromatography over styrene-divinylbenzene copolymer (methanol: water=4:1) and resulting powder is washed with ethyl acetate to give 7β-[(Z)-2-(2-aminothiazol-4-yl)-2-(1-carboxy-1-methylethoxyimino)acetamido]-3-(1,2,3-triazol-4-ylthiomethylthio)-3-cephem-4-carboxylic acid (299 mg) as pale yellowish white powder. Yield: 71%.

NMR δ(D₂O-NaHCO₃) ppm: 1.48(s, 3H), 1.50(s, 3H), 3.50, 3.69(ABq, J=17.4 Hz, 2H), 4.12, 4.24(ABq, J=13.9 Hz, 2H), 5.19(d, J=4.9 Hz, 1H), 5.82(d, J=4.9 Hz, 1H), 6.99(s, 1H), 8.01(s, 1H). IR ν(KBr) cm⁻¹: 3600–2400br, 1768, 1670, 1635, 1580, 1535, 1385, 1360.

This compound is a potent antibacterial against *Proteus mirabilis* PR4 (0.01 μg/ml), Serratia marcescens A13880 (0.8 μg/ml), and Pseudomonas aeruginosa A25619 (1.6 μg/ml).

17) Acyl=(Z)-2-[2-(t-butoxycarbonylamino to amino)-thiazol-4-yl]-2-(trityl to H)oxyiminoacetyl Het=1-methyl-1,2,3-triazol-4-yl (1E10-1)

To a solution of 7β-[(Z)-2-(2-t-butoxycarbonylamino-thiazol-4-yl)-2-trityloxyiminoacetamido]-3-(1-methyl-1,2,3-triazol-4-yl)thiomethylthio-3-cephem-4-carboxylic acid diphenylmethyl ester (708 mg: 0.683 mMol.) in a mixture of anisole (2 ml) and nitromethane (8 ml) is added dropwise a solution of aluminum chloride (727 mg: 5.47 mMol.) in anisole (2 ml) at −40° C., and the mixture is stirred for 1 hour at −30°—−40° C. The reaction mixture is diluted with 1N-hydrochloric acid (5.5 ml) and water and washed with ethyl acetate. The aqueous layer is concentrated under reduced pressure to remove organic solvent and passed through a column of styrene-divinylbenzene copolymer adsorbent. The product is eluted with methanol-water (4:1) to give 7β-[(Z)-2-(2-aminothiazol-4-yl)-2-hydroxyiminoacetamido]-3-(1-methyl-1,2,3-triazol-4-yl)thiomethylthio-3-cephem-4carboxylic acid as pale yellow powder (96.3 mg). Yield: 27%.

NMR δ(D₂O-NaHCO₃) ppm: 3.50, 3.81 (ABq, J=17.4 Hz, 2H), 4.11(s, 3H), 4.12, 4.22 (ABq, J=14.0 Hz, 2H), 5.24(d, J=4.6 Hz, 1H), 5.83(d, J=4.6 Hz, 1H), 6.99(s, 1H), 8.09(s, 1H). IR ν(KBr) cm⁻¹: 3252, 2928, 1770, 1650, 1620, 1523, 1404, 1348, 1181, 1019.

This compound is a potent antibacterial against *Escherichia coli* 7437 (0.02 μg/ml), *Enterobacter cloacae* SR233 (0.8 μg/ml), and *Haemophilus influenzae* SR3508 (0.1 μg/ml).

18) Acyl=(Z)-2-[2-(t-butoxycarbonylamino to amino) thiazol-4-yl)-2-(trityl to H) oxyiminoacetyl Het=2-methyl-1,2,3-triazol-4-yl (1E10-2)

To a solution of 7β-[(Z)-2-(2-t-butoxycarbonylamino-thiazol-4-yl)-2-trityloxyiminoacetamido]-3-(2-methyl-1,2,3-triazol-4-yl)thiomethylthio-3-cephem-4-carboxylic acid diphenylmethyl ester (1.39 g: 1.34 mMol.) in a mixture anisole (5 ml) and nitromethane (20 ml) is added dropwise a solution of aluminum chloride (1.43 g: 10.8 mMol.) in anisole (5 ml) at −40° C. After stirring at −30° to −40° C. for 1 hour, the mixture is diluted with 1N-hydrochloric acid (11 ml) and water and washed with ethyl acetate. The aqueous layer is concentrated under reduced pressure to remove organic solvents and passed through a column of styrene-divinylbenzene copolymer adsorbent. The product is eluted with methanol-water (4:1) to give 7β-[(Z)-2-(2-aminothiazol-4-yl)-2-hydroxyiminoacetamido]-3-(2-methyl-1,2,3-triazol-4-yl)thiomethylthio-3-cephem-4-carboxylic acid as pale yellow powder (534 mg). Yield: 75%.

NMR δ(D₂O-NaHCO₃) ppm: 3.52, 3.80 (ABq, J=17.3 Hz, 2H), 4.17 (s, 3H), 4.18, 4.25 (ABq, J=13.7 Hz, 2H), 5.23(d, J=4.8 Hz, 1H), 5.82(d, J=4.8 Hz, 1H), 6.99(s, 1H), 7.84(s, 1H). IR ν(KBr) cm⁻¹: 3288, 1768, 1663, 1606, 1530, 1365, 1255, 1177, 1005.

This compound is a potent antibacterial against *Escherichia coli* 7437 (0.02 μg/ml).

19) Acyl=(Z)-2-[2-(t-butoxycarbonylamino to amino)-thiazol-4-yl]-2-(trityl to H)oxyiminoacetyl Het=3-methyl-1,2,3-triazol-4-yl (1E10-3)

To a solution of 7β-[(Z)-2-(2-t-butoxycarbonylamino-thiazol-4-yl)-2-trityloxyiminoacetamido]-3-(3-methyl-1,2,3-triazol-4-yl) thiomethylthio-3-cephem-4-carboxylic acid diphenylmethyl ester (900 mg: 0.869 mMol.) in a mixture of anisole (4 ml) and nitromethane (16 ml) is added a solution of aluminum chloride (924 mg: 6.95 mMol.) in anisole (2 ml) at −40° C., and the mixture is stirred for 1 hour at −40°—−30° C. The reaction mixture is diluted with 1N-hydrochloric acid (7 ml) and water and washed with ethyl acetate. The aqueous layer is concentrated under reduced pressure to remove organic solvent and passed through a column of styrene-divinylbenzene copolymer adsorbent. The product is eluted with methanol-water (4:1) to give 7β-[(Z)-2-(2-aminothiazol-4-yl)-2-hydroxyiminoacetamido]-3-(3-methyl-1,2,3-triazol-4-yl)thiomethylthio-3-cephem-4-carboxylic acid as pale yellow powder (366 mg). Yield: 80%.

NMR δ(D₂O-NaHCO₃) ppm: 3.53, 3.78 (ABq, J=17.4 Hz, 2H), 4.08(s, 3H), 4.14, 4.27 (ABq, J=14.1 Hz, 2H), 5.23(d, J=4.5 Hz, 1H), 5.84(d, J=4.5 Hz, 1H), 6.98(s, 1H), 7.95(s, 1H). IR ν(KBr) cm⁻¹: 3204, 2984, 1768, 1664, 1610, 1529, 1382, 1347, 1262, 1176, 1127, 996.

This compound is a potent antibacterial against *Escherichia coli* 7437 (0.02 μg/ml) and *Enterobacter cloacae* SR233 (0.4 μg/ml). IR ν(KBr) cm⁻¹: 3204, 2984, 1768, 1664, 1610, 1529, 1382, 1347, 1262, 1176, 1127, 996.

This compound is a potent antibacterial against *Escherichia coli* 7437 (0.02 μg/ml) and *Enterobacter cloacae* SR233 (0.4 μg/ml).

20) Acyl=(Z)-2-[2-(t-butoxycarbonylamino to amino) thiazol-4-yl]-2-(trityl to H) oxyiminoacetyl Het=1-(trityl to H)-1,2,4-triazol-4-yl (1E11)

To a solution of 7β-[(Z)-2-(2-t-butoxycarbonylamino-thiazol-4-yl)-2-trityloxyiminoacetamido]-3-(1-trityl-1,2,4-triazol-3-yl)thiomethylthio-3-cephem-4-carboxylic acid diphenylmethyl ester (1.89 g: 1.50 mMol.) in a mixture of anisole (7 ml) and nitromethane (28 ml) is added dropwise a solution of aluminum chloride (1.99 g: 15 mMol.) in anisole (7 ml) at −30°—−40° C., and the mixture is stirred at the same temperature for 1 hour. The reaction mixture is diluted with 1N-hydrochloric acid (15 ml) and water and washed with ethyl acetate. The aqueous layer is concentrated under reduced pressure to remove organic solvents and passed through a column of styrene-divinylbenzene copolymer adsorbent. The product is eluted with methanol-water (2:3) to give 7β-[(Z)-2-(2-aminothiazol-4-yl)-2-hydroxyiminoacetamido]-3-(1,2,4-triazol-3-yl)thiomethylthio-3-cephem-4-carboxylic acid as pale yellow powder (418 mg). Over-all yield: 34%.

NMR δ(D₂O-NaHCO₃) ppm: 3.54, 3.79(ABq, J=17.4 Hz, 2H), 4.42(s, 2H), 5.21(d, J=4.3 Hz, 1H), 5.83(d, J=4.3 Hz, 1H), 6.98(s, 1H), 8.40(s, 1H). IR ν(KBr) cm⁻¹: 3280, 3132, 1768, 1665, 1605, 1530, 1390, 1349, 1273, 1178, 1004.

This compound is a potent antibacterial against *Escherichia coli* 7437 (0.02 μg/ml), *Enterobacter cloacae* SR233 (0.8 μg/ml), and *Klebsiella pneumoniae* SR1 (0.05 μg/ml).

21) Acyl=(Z)-2-[2-(t-butoxycarbonylamino to amino) thiazol-4-yl]-2-(trityl to H) oxyiminoacetyl Het=1-methyl-1,2,4-triazol-3-yl (4E7-7)

To a solution of 7β-[(Z)-2-(2-t-butoxycarbonylaminothiazol-4-yl)-2-trityloxyiminoacetylamino]-3-(1-methyl-1,2,4-triazol-3-ylthiomethylthio)-3-cephem-4-carboxylic acid diphenylmethyl ester (1.52 g: 1.47 mMol.) in a mixture of anisole (5 ml) and nitromethane (20 ml) at −40° C. is added a solution of aluminum chloride (1.56 g: 11.7 mMol.) in anisole (5 ml), and the mixture is stirred at −30° to −40° C. for 1 hour. The reaction mixture is mixed with 1N-hydrochloric acid (12 ml), diluted with water, washed with ethyl acetate, concentrated to remove remaining organic solvents, and passed through a column of styrene-divinylbenzene copolymer adsorbent. The adsorbed product is eluted with water-methanol (1:4). The eluate is concentrated to give powder and washed with ethyl acetate to give 7β-[(Z)-2-(2-aminothiazol-4-yl)-2-hydroxyiminoacetylamino]-3-(1-methyl-1,2,4-triazol-3-ylthiomethylthio)-3-cephem-4-carboxylic acid (628 mg) as yellow powder. Yield: 81%.

NMR δ(D$_2$O-NaHCO$_3$) ppm: 3.55, 3.83(ABq, J=17.2 Hz, 2H), 3.89(s, 3H), 4.40(s, 2H), 5.24(d, J=4.7 Hz, 1H), 5.82(d, J=4.7 Hz, 1H), 6.99(s, 1H), 8.36(s, 1H). IR ν(KBr) cm$^{-1}$: 3200br, 1765, 1660, 1630, 1600, 1520, 1380, 1348.

22) Acyl=(Z)-2-[2-(t-butoxycarbonylamino to amino)-thiazol-4-yl]-2-(trityl to H)oxyiminoacetyl Het=2-methyl-1,2,4-triazol-3-yl (4E7-8)

To a solution of 7β-[(Z)-2-(2-t-butoxycarbonylaminothiazol-4-yl)-2-trityloxyiminoacetylamino]-3-(2-methyl-1,2,4-triazol-3-ylthiomethylthio)-3-cephem-4-carboxylic acid diphenylmethyl ester (1.54 g: 1.49 mMol.) in a mixture of anisole (5 ml) and nitromethane (20 ml) at −40° C. is added a solution of aluminum chloride (1.58 g: 11.9 mMol.) in anisole (5 m), and the mixture is stirred at −30° to −40° C. for 50 minutes. The reaction mixture is mixed with 1N-hydrochloric acid (12 ml), diluted with water, washed with ethyl acetate, concentrated to remove the remaining organic solvents, and passed through a styrene-divinylbenzene copolymer adsorbent column. The absorbed product is eluted with water-methanol (1:4). The eluate is concentrated to give powder which is washed with ethyl acetate to give 7β-[(Z)-2-(2-aminothiazol-4-yl)-2hydroxyiminoacetyl]-3-(2-methyl-1,2,4-triazol-3-ylthiomethylthio)-3-cephem-4-carboxylic acid (654 mg). Yield: 83%.

NMR δ(D$_2$O-NaHCO$_3$) ppm: 3.54, 3.81(ABq, J=17.4 Hz, 2H), 3.85(s, 3H), 4.44, 4.50(ABq, J=14.1 Hz, 2H), 5.21(d, J=4.8 Hz, 1H), 5.83(d, J=4.8 Hz, 1H), 6.98(s, 1H), 8.03(s, 1H). IR ν(KBr) cm$^{-1}$: 3200br, 1765, 1655, 1600, 1525, 1473, 1382, 1345.

23) Acyl=(Z)-2-[2-(t-butoxycarbonylamino to amino)-thiazol-4-yl]-2-(trityl to H)oxyiminoacetyl Het=4-methyl-1,2,4-triazol-3-yl (4E7-16)

To a solution of 7β-[(Z)-2-(2-t-butoxycarbonylaminothiazol-4-yl)-2-trityloxyiminoacetylamino]-3-(4-methyl-1,2,4-triazol-3-ylthiomethylthio-3-cephem-4-carboxylic acid diphenylmethyl ester (378 mg: 0.365 mMol.) in a mixture of anisole (1 ml) and nitromethane (4 ml) at −40° C. is added a solution of aluminum chloride (388 mg: 2.92 mMol.) in anisole (1 ml), and the mixture is stirred at −30° to −40° C. for 50 minutes. The reaction mixture is mixed with 1N-hydrochloric acid (3 ml), diluted with water, washed with ethyl acetate, concentrated under reduced pressure to remove remaining organic solvents, add purified by chromatography over styrene-divinylbenzene copolymer resin (methanol: water=4:1). The resulting powder is washed with ethyl acetate to give 7β-[(Z)-2-(2-aminothiazol-4-yl)-2hydroxyiminoacetylamino]-3-(4-methyl-1,2,4-triazol-3-ylthiomethylthio)-3-cephem-4-carboxylic acid (150 mg) as yellow powder. Yield: 78%.

NMR δ(D$_2$O-NaHCO$_3$) ppm: 3.69(s, 3H), 3.53, 3.80(ABq, J=17.5 Hz, 2H), 4.35, 4.50(ABq, 13.4 Hz, 2H), 5.19(d, J=4.9 Hz, 1H), 5.83(d, J=4.9 Hz, 1H), 7.00(s, 1H), 8.50(s, 1H). IR ν(KBr) cm$^{-1}$: 3200br, 1767, 1655, 1630, 1605, 1520, 1377, 1340.

This compound is a potent antibacterial against *Escherichia coli* EC-14 (0.05 μl/ml) and *Morgania morganii* SR9 (0.1 μl/ml).

24) Acyl=(Z)-2-[2-(t-butoxycarbonylamino to amino) thiazol-4-yl]-2-(trityl to H)oxyiminoacetyl Het=1,2,3-thiadiazol-5-yl (3E3-2)

To a solution of 7β-[(Z)-2-(2-t-butoxycarbonylaminothiazol-4-yl)-2-trityloxyiminoacetyl]amino-3-(1,2,3-thiadiazol-5-yl) thiomethylthio-3-cephem-4-carboxylic acid diphenylmethyl ester (1.21 g: 1.16 mMol.) in a mixture of anisole (4 ml) and nitromethane ( 16 ml) cooling at −30° to −40° C. is added a solution of aluminum chloride (1.23 g: 9.25 mMol.) in anisole (4 ml), and the mixture is stirred at −30° to −40° C. for 50 minutes. To the reaction mixture is added 1N-hydrochloric acid (10 ml), diluted with water, and washed with ethyl acetate. The aqueous layer is concentrated to remove the organic solvents, purified by styrene-divinylbenzene copolymer chromatography (methanol: water=4:1) and the resulting powder is washed with ethyl acetate to give 7β-[(Z)-2-(2-aminothiazol-4-yl)-2-hydroxyiminoacetyl]amino-3-(1,2,3-thiadiazol-5-yl)thiomethylthio-3-cephem-4-carboxylic acid as yellow powder (440 mg). Yield 71%.

NMR δ(D$_2$O-NaHCO$_3$) ppm: 3.58, 3.88(ABq, J=17.4 Hz, 2H), 4.37, 4.48(ABq J=14.1 Hz, 2H), 5.25(d, J=4.7 Hz, 1H), 5.83(d, J=4.7 Hz, 1H), 6.97(s, 1H), 8.76(s, 1H). IR ν(KBr) cm$^{-1}$: 3200br, 1760, 1655, 1600, 1520, 1380, 1340, 1200, 1170.

This compound shows a strong antibacterial activity against *Escherichia coli* 7437 (0.01 μg/ml), *Escherichia coli* SR377 (0.4 μg/ml), *Morgania morganii* SR9 (0.05 μg/ml), and *Enterobacter cloacae* SR233 (0.4 μg/ml).

25) Acyl=(Z)-2-[2-(t-butoxycarbonylamino to amino)thiazol-4-yl]-2-(trityl to H)oxyiminoacetyl Het=1,3,4-thiadiazol-2-yl (2E3-1)

To a solution of 7β-[(Z)-2-(2-t-butoxycarbonylaminothiazol-4-yl)-2-trityloxyiminoacetamido]-3-(1,3,4-thiadiazol-2-ylthiomethylthio)-3-cephem-4-carboxylic acid diphenylmethyl ester (535 mg: 0.51 mMol.) in a mixture of anisole (1 ml) and nitromethane (4 ml) is added a solution of aluminum chloride (0.61 g: 4.6 mMol.) in anisole (2 ml) at −30° C. and the mixture is stirred for 40 minutes. The reaction mixture is mixed with ethanol (2 ml), stirred for 5 minutes at the same temperature, diluted with 1N-hydrochloric acid (6 ml) and water (200 ml), and washed with ethyl acetate. The aqueous layer is concentrated under reduced pressure to remove the organic solvents and passed through a styrene-divinylbenzene copolymer column. The adsorbed material is eluted with a methanol-water (4:1) mixture. The eluate is concentrated to give 7β-[(Z)-2-(2-aminothiazol-4-yl)-2-hydroxyiminoacetamido]-3-(1,3,4-thiadiazol-2-ylthiomethylthio)-3-cephem-4-carboxylic acid as pale yellow solid (201 mg). Yield: 74%.

NMR δ(D$_2$O-NaHCO$_3$) ppm: 3.60, 3.89(ABq, J=17 Hz, 2H), 4.57, 4.64(ABq, J=14 Hz, 2H), 5.24(d, J=5

Hz, 1H), 5.83(d, J=5 Hz, 1H), 6.98(s, 1H), 9.41(s, 1H). IR ν(KBr) cm$^{-1}$: 3300, 1765, 1665, 1600, 1370.

This compound is a potent antibacterial against *Escherichia coli* SR377 (0.4 μg/ml), *Enterobacter cloacae* SR233 (0.4 μg/ml), and *Morgania morganii* SR9 (0.1 μg/ml).

26) Acyl=(Z)-2-[2-(t-butoxycarbonylamino to amino)-thiazol-4-yl]-2-(trityl to H)oxyiminoacetyl Het=2-methyl-1,3,4-thiadiazol-5-yl (2E3-2)

To a solution of 7β-[(Z)-2-(2-t-butoxycarbonylaminothiazol-4-yl)-2-trityloxyiminoacetamido]-3-(2-methyl-1,3,4-thiadiazol-5-ylthiomethylthio)-3-cephem-4-carboxylic acid diphenylmethyl ester (388 mg: 0.368 mMol.) in a mixture of anisole (1 ml) and nitromethane (4 ml) at −30° C. is added a solution of aluminum chloride (0.45 g: 9.2 equivalents: 3.4 mMol.) in anisole (1.5 ml), and the mixture is stirred for 40 minutes. The reaction mixture is mixed with ethanol (2 ml), stirred for 5 minutes at the same temperature, and diluted with 1N-hydrochloric acid (6 ml) and water (200 ml). The aqueous layer is taken, washed with ethyl acetate, concentrated under reduced pressure to remove the organic solvents, and passed through a column of styrene-divinylbenzene copolymer. The column is eluted with methanol-water(4:1). The eluate is concentrated to give 7β-[(Z)-2-(2-aminothiazol-4-yl)-2-hydroxyiminoacetamido]-3-(2-methyl-1,3,4-thiadiazol-5-ylthiomethylthio)-3-cephem-4-carboxylic acid (149 mg). Yield: 75%.

NMR δ(D$_2$O-NaHCO$_3$) ppm: 2.72(s, 3H), 3.58, 3.87(ABq, J=17 Hz, 2H), 4.51, 4.57(ABq, J=14 Hz, 2H), 5.23(d, J=5 Hz, 1H), 5.83(d, J=5 Hz, 1H), 6.97(s, 1H). IR ν(KBr) cm$^{-1}$: 3200, 1772, 1668, 1605, 1515, 1390, 1340.

This compound is a potent antibacterial against *Escherichia coli* 7437 (0.02 μg/ml), *Enterobacter cloacae* SR233 (0.8 μg/ml), *Escherichia coli* SR377 (0.8 μg/ml), and *Morgania morganii* SR9 (0.05 μg/ml).

27) Acyl=(Z)-2-[2-(t-butoxycarbonylamino to amino)thiazol-4-yl]-2-(trityl to H)oxyiminoacetyl Het=tetrazol-5-yl (3E3-3)

To a solution of 7β-[(Z)-2-(2-t-butoxycarbonylaminothiazol-4-yl)-2-trityloxyiminoacetyl]amino-3-(5-tetrazolyl)thiomethylthio-3-cephem-4-carboxylic acid diphenylmethyl ester (942 mg: containing ca. 10% of byproduct) in a mixture of anisole (3 ml) and nitromethane (12 ml) cooling at −30° to −40° C. is added a solution of aluminum chloride (980 mg: 7.37 mMol.) in anisole (3 ml), and the mixture is stirred at −30° to −40° C. for 1 hour. The reaction mixture is diluted with 1N-hydrochloric acid (7.5 ml) and water, washed with ethyl acetate, concentrated under reduced pressure to remove the organic solvents, and subjected to styrene-divinylbenzene copolymer chromatography (methanol:water=2:3). The resulting powder is washed with ethyl acetate to give 7β-[(Z)-2-(2-aminothiazol-4-yl)-2-hydroxyiminoacetyl]amino-3-(tetrazol-5-yl)thiomethylthio-3-cephem-4-carboxylic acid as pale yellow powder (289 mg). Yield: 28% (from 7β-[(Z)-2-(2-t-butoxycarbonylaminothiazol-4-yl)-2-trityloxyiminoacetyl]amino-3-methanesulfonyloxy-3-cephem-4-carboxylic acid diphenylmethyl ester).

NMR δ(D$_2$O-NaHCO$_3$) ppm: 3.47, 3.65(ABq, J=17.4 Hz, 2H), 4.38, 4.43 (ABq, J=13.7 Hz, 2H), 5.18(d, J=4.6 Hz, 1H), 5.83(d, J=4.6 Hz, 1H), 6.99(s, 1H). IR ν(KBr) cm$^{-1}$: 3200br, 1765, 1650, 1600, 1525, 1385, 1345, 1175.

This compound shows a strong antibacterial activity against *Escherichia coli* 7437 (0.01 μg/ml).

28) Acyl=(Z)-2-[2-(t-butoxycarbonylamino to amino)-thiazol-4-yl]-2-(trityl to H)oxyiminoacetyl Het=1-methyl-5-tetrazolyl (3E3-4)

To a solution of 7β-[(Z)-2-(2-t-butoxycarbonylaminothiazol-4-yl)-2-trityloxyiminoacetyl]amino-3-(1-methyl-5-tetrazolyl)thiomethylthio-3-cephem-4-carboxylic acid diphenylmethyl ester (576 mg: 0.555 mMol.) in a mixture of anisole (2 ml) and nitromethane (8 ml) cooling at −30° to −40° C. is added a solution of aluminum chloride (591 mg: 4.44 mMol.) in anisole (2 ml), and the mixture is stirred at −30° to −40° C. for 1 hour. The reaction mixture is diluted with 1N-hydrochloric acid (5 ml) and water and washed with ethyl acetate. The aqueous layer is concentrated under reduced pressure to remove the organic solvents, and purified by styrene-divinylbenzene copolymer chromatography (methanol:water=4:1). The resulting powder is washed with ethyl acetate to give 7β-[(Z)-2-(2-aminothiazol-4-yl)-2-hydroxyiminoacetyl]amino-3-(1-methyl-5-tetrazolyl)-thiomethylthio-3-cephem-4-carboxylic acid as yellow powder (200 mg). Yield: 68%.

NMR δ(D$_2$O-NaHCO$_3$) ppm: 3.59, 3.90(ABq, J=17.4 Hz, 2H), 4.00(s, 3H), 4.58, 4.63(ABq, J=13.8 Hz, 2H), 5.24(d, J=4.9 Hz, 1H), 5.83(d, J=4.9 Hz, 1H), 6.98(s, 1H). IR ν(KBr) cm$^{-1}$: 3300br, 1765, 1660, 1605, 1525, 1385, 1345, 1170.

This compound shows a strong antibacterial activity against *Escherichia coli* 7437 (0.02 μg/ml), *Escherichia coli* SR377 (0.4 μg/ml), *Morgania morganii* SR9 (0.1 μg/ml), and *Enterobacter cloacae* SR233 (0.8 μg/ml).

29) Acyl=(Z)-2-[2-(t-butoxycarbonylamino to amino)-thiazol-4-yl]-2-(trityl to H)oxyiminoacetyl Het=2-methyltetrazol-5-yl (4E7-09)

To a solution of 7β-[(Z)-2-(2-t-butoxycarbonylaminothiazol-4-yl)-2-trityloxyiminoacetylamino]-3-(2-methyltetrazol-5-ylthiomethylthio)-3-cephem-4-carboxylic acid diphenylmethyl ester (1.16 g: 1.12 mMol.) in a mixture of anisole (4 ml) and nitromethane (16 ml) at −40° C. is added a solution of aluminum chloride (1.19 g: 8.95 mMol.) in anisole (4 ml), and the mixture is stirred at −30° to −40° C. for 1 hour. The reaction mixture is mixed with 1N-hydrochloric acid (9 ml), diluted with water, washed with ethyl acetate, concentrated to remove the remaining organic solvents, and passed through a column of styrene-divinylbenzene copolymer adsorbent. The adsorbed material is eluted with water-methanol (1:4) and concentrated to give powder which is washed with ethyl acetate to give 7β-[(Z)-2-(2-aminothiazol-4-yl)-2-hydroxyiminoacetamido]-3-(2-methyltetrazol-5-ylthiomethylthio)-3-cephem-4-carboxylic acid (466 mg) as yellow powder. Yield: 79%.

NMR δ(D$_2$O-NaHCO$_3$) ppm: 3.58, 3.88(ABq, J=17.3 Hz, 2H), 4.36(s, 3H), 4.50 (s, 2H), 5.26(d, J=4.7 Hz, 1H), 5.82(d, J=4.7 Hz, 1H), 6.98(s, 1H). IR ν(KBr) cm$^{-1}$: 3300br, 1767, 1660, 1630, 1600, 1528, 1387, 1340, 1321.

30) Acyl=(Z)-2-[2-(t-butoxycarbonylamino to amino) thiazol-4-yl]-2-(trityl to H)oxyiminoacetyl Het=2-pyridyl (2E3-3)

To a solution of 7β-[(Z)-2-(2-t-butoxycarbonylaminothiazol-4-yl)-2-trityloxyiminoacetamido]-3-(2-pyridylthiomethylthio)-3-cephem-4-carboxylic acid diphenylmethyl ester (722 mg: 0.70 mMol.) in a mixture of anisole (2 ml) and nitromethane (8 ml) cooling at −40° C. is added a solution of aluminum chloride (744 mg; 5.59 mMol.) in anisole (2 ml), and the mixture is stirred at −30° to −40° C. for 1 hour. The reaction mixture is diluted with 1N-hydrochloric acid (6 ml) and water, washed with ethyl acetate, concentrated under reduced pressure to remove the organic solvents, and passed through a styrene-divinylbenzene copolymer column. The adsorbed material is eluted with methanol-water (4:1). The eluate is concentrated. The residue is washed with ethyl acetate and dried to give 7β-[(Z)-2-(2-amino-thiazol-4-yl)-2-hydroxyiminoacetylamino]-3-(2-pyridyl-thiomethylthio)-3-cephem-4-carboxylic acid (289 mg). Yield: 79%.

NMR δ($D_2O$-$NaHCO_3$) ppm: 3.55, 3.78(ABq, J=17.2 Hz, 2H), 4.43, 4.49 (ABq, J=14.0 Hz, 2H), 5.16(d, J=4.6 Hz, 1H), 6.96(s, 1H), 7.23(ddd, J=7.5 Hz, J=4.9 Hz, J=0.8 Hz, 1H), 7.46(brd, J=8.0 Hz, 1H), 7.74(ddd, J=8.0 Hz, J=7.5 Hz, J=1.6 Hz, 1H), 8.39(brd, J=4.9 Hz, 1H). IR ν(KBr) cm$^{-1}$: 3320, 2976, 1764, 1665, 1619, 1575, 1530, 1415, 1353, 1120.

This compound is a potent antibacterial against *Escherichia coli* 7437 (0.01 μg/ml) and shows a high blood level on oral administration (18.7 μg/ml: 15 minutes, mice).

The assay of each compound was done as follows:

Antibacterial activity in vitro

A solution of the test compound in 0.01N-aqueous sodium hydrogen carbonate was applied to an agar plate by two-fold dilution method and the minimal inhibitory concentrations against Gram-negative and Gram-positive bacteria were measured according to the standard method of the Japan Society of Chemotherapy.

Blood level at 15 minutes after oral administration

A test compound (40 mg/kg) in a 5% suspension of arabic gum was administered to a mouse (weighing ca. 25 g) through an enteral tube. After 15 minutes, the blood in the heart cavity was taken and the concentration of the test compound was measured by the band culture method using *Escherichia coli* 7437.

Example 8 Medical formulations.

1) Granules

| | |
|---|---|
| 7β-[(Z)-2-(2-aminothiazol-4-yl)-2-hydroxyiminoacetylamino]-3-(1,2,3-triazol-4-ylthiomethylthio)-3-cephem-4-carboxylic acid | 100 mg |
| lactose | 600 mg |
| corn starch | 290 mg |
| hydroxypropylcellulose | 10 mg |

Above materials are granulated in a conventional wet method and 1 g each is packaged as granule formulation and given thrice in a day to a patient suffering from infection caused by sensitive bacteria.

2) Tablets

| | |
|---|---|
| 7β-[(Z)-2-(2-aminothiazol-4-yl)-2-methoxyiminoacetylamino]-3-(1,2,3-triazol-4-ylthiomethylthio)-3-cephem-4-carboxylic acid | 100 mg |
| lactose | 65 mg |
| corn starch | 32 mg |
| hydroxypropylcellulose | 2 mg |
| magnesium stearate | 1 mg |

Above materials are granulated in a conventional wet method and formulated with tabletting machine to give tablets of diameter 7.5 mm and given twice in a day to a patient suffering from infection caused by sensitive bacteria.

3) Hard capsules

| | |
|---|---|
| 7β-[(Z)-2-(2-aminothiazol-4-yl)-2-methoxyiminoacetylamino]-3-(1,2,4-triazol-3-ylthiomethylthio)-3-cephem-4-carboxylic acid | 100 mg |
| corn starch | 47 mg |
| magnesium stearate | 1.5 mg |
| talcum powder | 1.5 mg |

Above materials are granulated in a conventional wet method and filled in a hard gelatine capsules of size No. 4 and given thrice in a day to a patient suffering from infection caused by sensitive bacteria.

What we claim is:

1. A compound selected from the group consisting of: AcSR$^2$SR$^1$Het and HalR$^2$SR$^1$Het wherein Ac is $C_1$-$C_{12}$ acyl; Hal is halogen; R$^1$ is a single bond or $C_1$-$C_4$ alkylene; and R$^2$ is a straight or branched $C_1$-$C_4$ alkylene; Het is 1, 2, 3-triazol-4-yl, or a derivative which is optionally protected at a nitrogen atom by one or more protecting groups selected from C1-C8 alkyl; C7-C19 aralkyl; C1-C8 alkylthio; C6-C12 arylthio; C5-C8 cycloalkylidene; C2-C12 alkoxycarbonyl the alkyl of which is cyclic or acyclic, substituted or unsubstituted and is selected from the group consisting of methyl, ethyl, propyl, cyclopropylmethyl, cyclopropylethyl, isopropyl, butyl, isobutyl, pentyl, hexyl, trichloroethyl, pyridylmethyl, cyclopentyl or cyclohexyl; C8-C19 aralkoxycarbonyl the aralkyl of which is benzyl, benzhydryl or nitrobenzyl, C7-C15 aroyl; C3-C9 trialkylsilyl; C3-C9 alkoxydialkylsilyl; and an acid capable of forming acid addition salt.

2. The compound as claimed in claim 1 where R$^1$ is a single bond.

3. The compound as claimed in claim 1 wherein R$^2$ is methylene.

4. The compound as claimed in claim 1 wherein R$^2$ is ethylidene.

5. The compound as claimed in claim 1 wherein Ac is acetyl.

6. The compound as claimed in claim 1 wherein Ac is benzoyl.

7. The compound as claimed in claim 1 wherein Hal is chloro.

* * * * *